US011957723B2

(12) United States Patent
Govindan et al.

(10) Patent No.: US 11,957,723 B2
(45) Date of Patent: Apr. 16, 2024

(54) METHODS AND USES OF MICROBIOME COMPOSITIONS, COMPONENTS, OR METABOLITES FOR TREATING NEURODEGENERATIVE DISEASES

(71) Applicant: MarvelBiome, Inc., Woburn, MA (US)

(72) Inventors: Jothi Amaranath Govindan, Malden, MA (US); Elamparithi Jayamani, Melrose, MA (US); Priti H. Chatter, Concord, MA (US); Mukesh Chatter, Concord, MA (US)

(73) Assignee: MarvelBiome, Inc., Woburn, MA (US)

( * ) Notice: Subject to any disclaimer, the term of this patent is extended or adjusted under 35 U.S.C. 154(b) by 0 days.

(21) Appl. No.: 17/947,083

(22) Filed: Sep. 16, 2022

(65) Prior Publication Data

US 2023/0087305 A1 Mar. 23, 2023

Related U.S. Application Data

(60) Provisional application No. 63/330,148, filed on Apr. 12, 2022, provisional application No. 63/245,648, filed on Sep. 17, 2021.

(51) Int. Cl.
| | |
|---|---|
| *A61K 35/747* | (2015.01) |
| *A61K 31/132* | (2006.01) |
| *A61K 31/19* | (2006.01) |
| *A61K 31/194* | (2006.01) |
| *A61K 31/198* | (2006.01) |
| *A61K 31/205* | (2006.01) |
| *A61K 31/405* | (2006.01) |

(Continued)

(52) U.S. Cl.
CPC .......... *A61K 35/747* (2013.01); *A61K 31/132* (2013.01); *A61K 31/19* (2013.01); *A61K 31/194* (2013.01); *A61K 31/198* (2013.01); *A61K 31/205* (2013.01); *A61K 31/405* (2013.01); *A61K 31/4172* (2013.01); *A61K 31/4402* (2013.01); *A61K 31/455* (2013.01); *A61K 31/522* (2013.01); *A61K 31/575* (2013.01); *A61K 35/741* (2013.01); *A61K 35/742* (2013.01); *A61K 35/745* (2013.01); *A61P 25/28* (2018.01)

(58) Field of Classification Search
CPC ....................................................... A61P 25/28
See application file for complete search history.

(56) References Cited

U.S. PATENT DOCUMENTS

2018/0148801 A1 5/2018 Jo et al.

FOREIGN PATENT DOCUMENTS

| WO | WO-2019/075456 A2 | 4/2019 |
| WO | WO-2023/044076 A1 | 3/2023 |

OTHER PUBLICATIONS

Boddy et al. "The gut microbiome: a key player in the complexity of amyotrophic lateral sclerosis (ALS)", Jan. 20, 2021, BMC Medicine, 19:13, p. 1-14. (Year: 2021).*

(Continued)

*Primary Examiner* — Gary B Nickol
*Assistant Examiner* — Amelia Nicole Dickens
(74) *Attorney, Agent, or Firm* — Choate, Hall & Stewart LLP; Stephanie L. Schonewald; Sowmya Subramanian

(57) ABSTRACT

Methods and uses of compositions (e.g. comprising one or more microbial strains, one or more components, one or more metabolites, or a combination thereof) for treating neurodegenerative diseases, disorders, and conditions are disclosed.

13 Claims, 36 Drawing Sheets

(51) Int. Cl.

| | |
|---|---|
| A61K 31/4172 | (2006.01) |
| A61K 31/4402 | (2006.01) |
| A61K 31/455 | (2006.01) |
| A61K 31/522 | (2006.01) |
| A61K 31/575 | (2006.01) |
| A61K 35/741 | (2015.01) |
| A61K 35/742 | (2015.01) |
| A61K 35/745 | (2015.01) |
| A61P 25/28 | (2006.01) |

(56) References Cited

OTHER PUBLICATIONS

Cogliati et al. "Bacillus Subtilis Delays Neurodegeneration and Behavioral Impairment in the Alzheimer's Disease Model Caenorhabditis Elegans", 2020, Journal of Alzheimer's Disease, vol. 73, p. 1035-1052. (Year: 2020).*
Kaur et al. "Effects of Probiotic Supplementation on Short Chain Fatty Acids in the AppNL-G-FMouse Model of Alzheimer's Disease", 2020, Journal of Alzheimer's Disease, vol. 76, p. 1083-1102. (Year: 2020).*
Naomi et al. "Probiotics for Alzheimer's Disease: A Systematic Review", Dec. 22, 2021, Nutrients, vol. 14, p. 1-24. (Year: 2021).*
Sun et al. "Effect of Clostridium butyricum against Microglia-Mediated Neuroinflammation in Alzheimer's Disease via Regulating Gut Microbiota and Metabolites Butyrate", Dec. 23, 2019, Molecular Nutrition & Food Research, vol. 64, Article 1900636, p. 1-11. (Year: 2019).*
Westfall et al. "Microbiome, probiotics and neurodegenerative diseases: deciphering the gut brain axis", Jun. 22, 2017, Cellular and Molecular Life Sciences, vol. 74, p. 3769-3787. (Year: 2017).*
International Search Report for PCT/US2022/43904, 4 pages, dated Jan. 31, 2023.
Written Opinion for PCT/US2022/43904, 12 pages, dated Jan. 31, 2023.
Ackerman, H.D. and Gerhard, G. S., Bile Acids in Neurodegenerative Disorders, Frontiers in Aging Neuroscience, 8:263 (2016).
Bensimon, G. et al., A study of riluzole in the treatment of advanced stage or elderly patients with amyotrophic lateral sclerosis, J. Neurol., 249:609-615 (2002).
Braak, H. et al., Idiopathic Parkinson's disease: possible routes by which vulnerable neuronal types may be subject to neuroinvasion by an unknown pathogen, Journal of Neuortransmission, 110:517-536 (2003).
Cersosimon, MG, and Benarroch, EE, Pathological correlates of gastrointestinal dysfunction in Parkinson's disease, Neurobiology of Disease, 46:559-564 (2012).
Cheignon, C. et al., Oxidative stress and the amyloid beta peptide in Alzheimer's disease, Redox Biol., 14:450-464 (2018).
Collier, TJ. et al., Ageing as a primary risk factor for Parkinson's disease: evidence from studies of non-human primates, Nature Reviews, Neuroscience, 12(6):359-366 (2011).
Dias, V. et al., The role of oxidative stress in Parkinson's disease, Journal of Parkinson's Disease, 3(4):461-491 (2013).
Donia, M. S. and Fischbach, M. A., Human Microbiota. Small molecules from the human microbiota, Science, 349:1254766-1254766 (2015).
Fijan, S., Microorganisms with claimed probiotic properties: an overview of recent literature, Int J Environ Res Public Health, 11(5): 4745-4767 (2014).
Floor, E. and Wetzel, MG., Increased protein oxidation in human substantia nigra pars compacta in comparison with basal ganglia and prefrontal cortex measured with an improved dinitrophenylhydrazine assay, J Neurochem, 70:268-275 (2002).
GBD 2013 Mortality and Causes of Death Collaborators, Global, regional, and national age-sex specific all-cause and cause-specific mortality for 240 causes of death, 1990-2013: a systematic analysis for the Global Burden of Disease Study 2013, Lancet, 385(9963):117-171 (2015).
GBD 2015 Mortality and Causes of Death Collaborators, Global, regional, and national incidence, prevalence, and years lived with disability for 310 diseases and injuries, 1990-2015: a systematic analysis for the Global Burden of Disease Study 2015, Lancet, 388(10053):1545-1602 (2016).
Glickman and Ciechanover, The ubiquitin-proteasome proteolytic pathway: destruction for the sake of construction, Physiol Rev, 82:373-42, (2002).
Halliwell, B., J., Oxidative stress and neurodegeneration: where are we now?, Neurochem, 97:1634-1658 (2006).
Hawkes, CH. et al., Parkinson's Disease The Dual Hit Theory Revisited, International Symposium of Olfaction and Taste, 1170:615-622 (2009).
Hawkes, CH. et al., Parkinson's disease: a dual-hit hypothesis, Neuropathology and Applied Neurobiology, 33:599-614 (2007).
Hill, J. M., et al., The gastrointestinal tract microbiome and potential link to Alzheimer's disease, Front Neurol., 5:43 (2014).
Hutkins et al, Prebiotics: why definitions matter, Curr. Opin. Biotechnol., 37:1-7 (2016).
Kabashi, et al., Proteasomes remain intact, but show early focal alteration in their composition in a mouse model of amyotrophic lateral sclerosis, J Neurochem, 105:2353-2366 (2008).
Kuo, YM. et al., Extensive enteric nervous system abnormalities in mice transgenic for artificial chromosomes containing Parkinson disease-associated alpha-synuclein gene mutations precede central nervous system changes, Human Molecular Genetics, 19(1):1633-1650 (2010).
Liu, X. et al., Formation of dopamine adducts derived from brain polyunsaturated fatty acids: mechanism for Parkinson disease, Journal of Biological Chemistry, 283(50):34887-34895 (2008).
Loeffler, et al., Neurofilament-Light Chain as Biomarker of Neurodegenerative and Rare Diseases With High Translational Value, Front Neurosci 14:579 (2020).
Migheli, et al., Ubiquitinated filamentous inclusions in spinal cord of patients with motor neuron disease, Neurosci Lett 114:5-10, (1990).
Moore, DJ. et al., Molecular pathophysiology of Parkinson's disease, Annu. Rev. Neurosci. 28:57-87 (2005).
Moreira, P. I. et al., Mitochondrial dysfunction is a trigger of Alzheimer's disease pathophysiology, Biochim. Biophys. Acta 1802:2-10 (2010).
Mukherjee, A. et al., Gut dysfunction in Parkinson's disease, Journal of Gastroenterology, 22(25):5742-5752 (2016).
Nelson, P. T., et al., Correlation of Alzheimer disease neuropathologic changes with cognitive status: a review of the literature, J. Neuropathol. Exp. Neurol. 71:362-381 (2012).
Noyce, AJ. et al., Meta-analysis of early nonmotor features and risk factors for Parkinson disease, Anals of Neurology, 72:893-901 (2012).
Pellegrini, C. et al., Intestinal dysfunction in Parkinson's disease: Lessons learned from translational studies and experimental models, Neurogastroenterology & Motility, 28(12):1781-1791 (2016).
Pires, A. O. et al., Old and new challenges in Parkinson's disease therapeutics, Therapeautics, Prog. Neurobiol. (2017); doi: 10.1016/j.pneurobio.2017.04.006.
Puttaparthi, K., et al., Aggregate formation in the spinal cord of mutant SOD1 transgenic mice is reversible and mediated by proteasomes, J Neurochem, 87:851-860 (2003).
Root, R. et al., Lysosome dysfunction as a cause of neurodegenerative diseases: Lessons from frontotemporal dementia and amyotrophic lateral sclerosis, Neuorobiology of Disease, 154:105360 (2021).
Rubinsztein, D. C., The roles of intracellular protein-degradation pathways in neurodegeneration, Nature, 443:780-786 (2006).
Shannon, KM. et al., Is alpha-synuclein in the colon a biomarker for premotor Parkinson's disease? Evidence from 3 cases, Mov. Disord. 27:716-719 (2012).
Sharon, G. et al., The Central Nervous System and the Gut Microbiome, Cell, 167:915-932 (2016).

(56) References Cited

OTHER PUBLICATIONS

Tieu, K., A guide to neurotoxic animal models of Parkinson's disease, Cold Spring Harb Perspect Med 1, a009316-a009316 (2011).

Vilchez, et al., RPN-6 determines C. elegans longevity under proteotoxic stress conditions, Nature, 489:263-268 (2012).

Yoriyaka, A. et al., Immunohistochemical detection of 4-hydroxynonenal protein adducts in Parkinson disease, Proceedings of the National Academy of Sciences, 93:2696-2701 (1996).

Zhang, J. et al., Parkinson's disease is associated with oxidative damage to cytoplasmic DNA and RNA in substantia nigra neurons, Am. J. Pathol. 154:1423-1429 (1999).

* cited by examiner

G1: Wildtype Male, Mock-treated
G2: SOD1 Male, Mock-treated
G3: SOD1 Male, CT6-treated
G4: SOD1 Male, CT6m-treated

| | % Change in CT6_Male | % Change in CT6_Female |
|---|---|---|
| Taurodeoxycholic acid | 135 | 738 |
| Tauroursodeoxycholic acid | 2 | 521 |
| Sulfolithocholylglycine | 47 | 417 |
| Glycocholic acid | 189 | 367 |
| Deoxycholic acid | 293 | 11 |
| Taurocholic acid | -19 | 620 |
| Taurochenodeoxycholic acid | -2 | 541 |
| Glycodeoxycholic acid | Detected only in CT6-treated | 100 |
| Glycochenodeoxycholic acid | -50 | 100 |
| Cholic acid | 367 | -26 |
| Hyodeoxycholic acid | 254 | -63 |
| Lithocholic acid | 128 | -6 |
| Taurolithocholic acid | 180 | 544 |
| Ursodeoxycholic acid | 109 | -63 |
| 3-oxocholic acid | 340 | -90 |
| Chenodeoxycholic acid | 207 | -72 |

FIG. 18B

METHODS AND USES OF MICROBIOME COMPOSITIONS, COMPONENTS, OR METABOLITES FOR TREATING NEURODEGENERATIVE DISEASES

CROSS REFERENCE TO RELATED APPLICATIONS

The present application claims priority to United States Provisional Patent Application Nos. 63/245,648 filed Sep. 17, 2021, and 63/330,148 filed Apr. 12, 2022, the entire contents of all of which are hereby incorporated by reference in their entirety.

BACKGROUND

Many neurodegenerative diseases, disorders, or conditions including, but not limited to, Amyotrophic lateral sclerosis (ALS), Alzheimer's Disease (AD), Huntington's Disease (HD), and Parkinson's Disease (PD), can cause degeneration of nerve cells and impact physical and/or mental functions. Currently, there are no effective treatments for such diseases, including for ALS, PD, or AD, and finding new drugs or treatment methods is a priority.

SUMMARY

The present disclosure provides an insight that compositions (e.g. microbiome compositions) as described herein may be used to treat diseases, disorders, or conditions (e.g. of the nervous system (e.g. a neurodegenerative disease, disorder, or condition (e.g. ALS, AD, PD, HD, etc.))) in a subject (e.g. a mammal (e.g. human, mice, etc.)). Among other things, the present disclosure describes technologies that can be used to treat, prevent, and/or reduce the risk of a disease, disorder, or condition (e.g. of the nervous system). In some embodiments, the present disclosure describes compositions and methods to evaluate the effects of administering such compositions (e.g. microbiome compositions as described herein) to a subject and/or to identify or characterize effects and/or modulation of levels of metabolites or a metabolome in a subject upon administration of such compositions. In some embodiments, the metabolites that may be modulated may be associated with certain diseases, disorders, or conditions. In some embodiments, such technologies can be useful to discern metabolite-level differences in a particular subject (e.g., patient) or population (e.g. before and after administration of disclosed compositions). Accordingly, the present disclosure also provides technologies that can be useful to identify and/or assess the nature and effect of disclosed compositions in specific subjects (e.g., patients) and/or populations and thus provide subject-specific information on how to treat a disease, disorder, or condition (e.g. of the nervous system) in an individual subject or individual population. For example, in some embodiments, technologies provided herein can be useful to identify subject-specific compositions, based on the metabolome in subject-specific samples, and treat and/or prevent a disease, disorder, or condition (e.g. of the nervous system) by administering disclosed compositions (e.g. subject-specific compositions) (e.g. to modulate subject's metabolome). Thus, technologies described herein may be useful as therapeutics and tools for reducing the risk of certain diseases, disorders, or conditions (e.g. of the nervous system), and for treating and/or preventing such diseases, disorders, or conditions.

Among other things, the present disclosure provides a method of treating or preventing a neurodegenerative disease, disorder, or condition. In some embodiments, a method comprises administering to a subject in need thereof a composition comprising one or more microbial strains, components (e.g. microbial components) thereof, or metabolites (e.g. microbial metabolites (e.g. derived from sources other than microbial strains (e.g. synthetically derived), derived from microbial strains) thereof. In some embodiments, a method comprises administering to a subject a composition comprising one or more metabolites. In some embodiments, a method comprises administering to a subject a composition comprising one or more microbial metabolites. In some embodiments, a neurodegenerative disease, disorder, or condition is Amyotrophic lateral sclerosis (ALS), Alzheimer's Disease (AD), Parkinson's Disease (PD), or Huntington's Disease (HD). In some embodiments, a neurodegenerative disease, disorder, or condition is ALS.

In some embodiments, a subject is animal. In some embodiments, a subject is a mammal, e.g., a mammal that experiences or is susceptible to a disease, disorder, or condition as described herein. In some embodiments, an animal is a vertebrate, e.g., a mammal, such as a non-human primate, (particularly a higher primate), a sheep, a dog, a rodent (e.g. a mouse or rat), a guinea pig, a goat, a pig, a cat, a rabbit, or a cow. In some embodiments, an animal is a non-mammal animal, such as a chicken, an amphibian, a reptile, or an invertebrate. In some embodiments, a subject is a human.

In some embodiments, a subject is suffering from or susceptible to one or more neurodegenerative diseases, disorders, or conditions as described herein. In some embodiments, a subject displays one or more symptoms of one or more neurodegenerative diseases, disorders, or conditions. In some embodiments, a subject has been diagnosed with one or more neurodegenerative diseases, disorders, or conditions as described herein. In some embodiments, the subject is receiving or has received certain therapy to diagnose and/or to treat one or more neurodegenerative diseases, disorders, or conditions.

In some embodiments, one or more microbial strains are from an animal microbiome. In some embodiments, one or more microbial strains are from a mammalian microbiome. In some embodiments, one or more microbial strains are from a human microbiome. In some embodiments, a human microbiome is a microbiome of a subject. In some embodiments, a human microbiome is administered to maintain or modulate the microbiome of a subject.

In some embodiments, one or more components or metabolites (e.g. of one or more microbial strains, microbial metabolites, (e.g. derived from sources other than microbial strains (e.g. synthetically derived), derived from microbial strains) are selected from Appendix 1, Appendix 3, or Appendix 4. In some embodiments, metabolites can be from one or more microbial strains. In some embodiments, metabolites can be from a source that is not a microbial strain, e.g., synthetically generated. In some embodiments, one or more metabolites (e.g. microbial metabolites of one or more microbial strains, (e.g. derived from sources other than microbial strains (e.g. synthetically derived), derived from microbial strains) is or comprises a bile acid. In some embodiments, one or more metabolites (e.g. microbial metabolities of one or more microbial strains, (e.g. derived from sources other than microbial strains (e.g. synthetically derived), derived from microbial strains) is or comprises Tauroursodeoxycholic acid. In some embodiments, one or more components or metabolites is Butyrylcarnitine, Theobromine, p-Hydroxyphenylpyruvic acid, Propionic acid, Picolinic acid, 2-Hydroxy-4methylvaleric acid, N6-Acetylysine, Urocanic acid, N5-Ethylglutamine, Trigonelline, Stachydrine, Ectoine, 5-Hydroxylysine, Arginine (arg), Cholic acid, 2-(4-Hydroxyphenyl)propionic acid, N-Acetyltryptophan, Hydroxyproline, Argininosuccinic acid, Glutamic acid (Glu), Sarcosine, 5-Methoxyindoleacetic acid, Indole-3-lactic acid, Isovalerylalanine, N-Acetylleucine, 1-Methylhistidine, N-Acetylephenylalanine, Proline (Pro), or any combination thereof. In some embodiments, one or more components or metabolites is 4-Hydroxyphenylpyruvic, Ectoine, Gramine, N-Acetyl-L-phenylalanine, Nepsilon-Acetyl-L-lysine, Stachydrine, Trigonelline, 3-Ureidopropionic acid, Theobromine, Hippuric acid, Imidazolepropionic acid, NG-Methyl-L-arginine, trans-Urocanic Acid, N-Acetyl-L-leucine, Sarcosine, Isobutyrylcarnitine, b-Hydroxyisovaleric acid, L-Theanine/N5-Ethylglutamine, 5-Hydroxylysine, Phenaceturic acid, betaine, hydroxyproline, Picolinic acid, 2-Aminoadipic acid, Glycerophosphocholine, carnitine, Glycerol 3-phosphate, Argininosuccinic acid, creatine, Terephthalic acid, Homocitrulline, Mucic acid, Homocysteinesulfinic acid, Trimethyllysine, Spermidine, Glyoxylic acid, XA0013 C6H604S, 3-Indoxylsulfuric acid, Nicotinamide, N-Formylglycine, Ureidoglycolate, N-Methylproline, Glucaric acid, Butyrylcarnitine, Methionine sulfoxide, Carboxymethyllysine, Glycolic acid, Phenaceturic acid, Diethanolamine, Phosphorylcholine, Guanidinosuccinic acid, N-Acetylhistidine, Glyceric acid, S-Methylmethionine, Cysteine glutathione disulfide, Kynurenine, N-Acetylphenylalanine, Threonic acid, Malic acid, 7,8-Dihydrobiopterin, Homovanillic acid, Taurocholic acid, 5-Methoxyindoleacetic acid, butyrate, b-Hydroxyisovaleric acid, 2-Oxoglutaric acid, N-Acetyltryptophan, Thiaproline, Hypotaurine, Cholic acid, Acetoacetic acid, Ethanolamine, Guanidoacetic acid, S-Sulfocysteine, Myristic acid C14:0 XA0027, or any combination thereof.

In some embodiments, one or more microbial strains are or comprise *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp., or a combination thereof. In some embodiments, one or more microbial strains are or comprise *Gluconacetobacter hanseni, Terrisporobacter glycolicus, Coprococcus* sp., *Lactobacillus plantarum, Veillonella* sp., *Bifidobacterium* sp., or a combination thereof. In some embodiments, one or more microbial strains are or comprise *Gluconacetobacter hanseni, Terrisporobacter glycolicus, Coprococcus catus, Lactobacillus plantarum, Veillonella atypica, Bifidobacterium breve*, or a combination thereof. In some embodiments, one or more microbial strains is or comprises *Bacillus subtilis*.

In some embodiments, a composition comprises two or more microbial strains. In some embodiments, a composition comprises five or more microbial strains. In some embodiments, a composition comprises ten or more microbial strains.

In some embodiments, a composition is administered topically, orally, subcutaneously, intravenously, intramuscularly, intracerebrally, intrathecally, rectally, opthalmically, intravitreally, or suprachoroidally. In some embodiments, a composition is administered orally. In some embodiments, a composition is administered intracerebrally.

In some embodiments, a composition is formulated as a syrup, a liquid, a tablet, a troche, a gummy, a capsule, a powder, a gel, a film, an injection, or an eye drop.

In some embodiments, each microbial strain of one or more microbial strains is present in a composition at a concentration from $10^1$ to $10^{15}$ CFU. In some embodiments, each microbial strain of one or more microbial strains is present in a composition at a concentration of at least $10^6$ CFU. In some embodiments, each microbial strain of one or more microbial strains in a composition comprises $10^1$ colony forming units (CFUs) to $10^{20}$ CFU. In some embodiments, each microbial strain of one or more microbial strains in a composition comprises $10^1$ colony forming units (CFUs) to $10^{15}$ CFU. In some embodiments, each microbial strain of one or more microbial strains in a composition comprises $10^6$ CFU to $10^{15}$ CFUs. In some embodiments, each microbial strain of one or more microbial strains in a composition comprises about $10^1$ CFU to $10^{15}$ CFU, or about $10^2$ CFU to $10^{14}$ CFU, or about $10^3$ CFU to $10^{13}$ CFU, or about $10^4$ CFU to $10^{13}$ CFU, or about $10^5$ CFU to $10^{12}$ CFU, or about $10^6$ CFU to $10^{11}$ CFU, or about $10^2$ CFU to $10^{10}$ CFU, or about $10^8$ CFU to $10^9$ CFU, or about $10^5$ CFU to $10^{10}$ CFU, or about $10^8$ CFU to $10^{12}$ CFU. In some embodiments, each microbial strain of one or more microbial strains in a composition comprises at least about $10^1$, $5 \times 10^1$, $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $10^9$, $5 \times 10^9$, $10^{10}$, $5 \times 10^{10}$, $10^{11}$, $5 \times 10^{11}$, $10^{12}$, or more CFUs. In some embodiments, each of one or more microbial strains in a composition comprises at most about $10^{15}$, $5 \times 10^{14}$, $10^{14}$, $5 \times 10^{13}$, $10^{13}$, $5 \times 10^{12}$, $10^{12}$, $5 \times 10^{11}$, $10^{11}$, $5 \times 10^{10}$, $10^{10}$, $5 \times 10^9$, $10^9$, $5 \times 10^8$, $10^8$, or less CFUs. In some embodiments, each microbial strain of one or more microbial strains in a composition comprises same number of CFUs. In some embodiments, some microbial strains of one or more microbial strains in a composition comprises a different number of CFUs.

The present disclosure provides, among other things, a composition for treating or a composition for use in treating a neurodegenerative disease, disorder, or condition comprising one or more microbial strains, components thereof, or metabolites thereof. In some embodiments, a composition, as described herein, comprises one or more metabolites (e.g. derived from sources other than microbial strains (e.g. synthetically derived), metabolites derived from microbial strains, etc.), wherein the composition is for treating a neurodegenerative disease, disorder, or condition.

The present disclosure provides a composition comprising one or more microbial strains selected from *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp., or a combination thereof. In some embodiments, a composition comprises one or more microbial strains selected from *Gluconacetobacter hanseni, Terrisporobacter glycolicus, Coprococcus* sp., *Lactobacillus plantarum, Veillonella atypica, Bifidobacterium* sp., or a combination thereof. In some embodiments, a composition comprises a microbial strain. In some embodiments, a microbial strain is *Bacillus subtilis*. In some embodiments, a composition comprises at least two microbial strains selected from a group consisting of *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp., or a combination thereof. In some embodiments, a composition comprises at least two microbial strains selected from a group consisting of *Gluconacetobacter hanseni, Terrisporobacter glycolicus, Coprococcus* sp., *Lactobacillus plantarum, Veillonella atypica, Bifidobacterium* sp., or a combination thereof. In some embodiments, a composition comprises at least five microbial strains selected from a group consisting of *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp., or a combination thereof. In some embodiments, a composition comprises at least five microbial strains selected from a group consisting of *Gluconacetobacter hanseni, Terrisporobacter glycolicus, Coprococcus* sp., *Lactobacillus plantarum, Veillonella atypica, Bifidobacterium* sp., or a combination thereof. In some embodiments, a composition comprises or consists of *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp. In some embodiments, a composition comprises or consists of *Gluconacetobacter hanseni, Terrisporobacter glycolicus, Coprococcus* sp., *Lactobacillus plantarum, Veillonella atypica, Bifidobacterium* sp.

In some embodiments, a composition, as described herein, comprises one or more metabolites (e.g. derived from sources other than microbial strains (e.g. synthetically derived), metabolities derived from microbial strains, etc.), wherein the composition is for treating a neurodegenerative disease, disorder, or condition.

In some embodiments, a composition is for topical, oral, subcutaneous, intravenous, intramuscular, intracerebral, intrathecal, rectal, opthalmical, intravitreal, or suprachoroidal administration. In some embodiments, a composition is for oral administration. In some embodiments, a composition is for intracerebral administration.

The present disclosure provides that a composition as described herein is for use in modulating one or more metabolites (e.g. microbial metabolites, (e.g. derived from sources other than microbial strains (e.g. synthetically derived), derived from microbial strains)) in a subject.

The present disclosure provides that a composition as described herein is for use in modulating one or more features in a subject. In some embodiments, one or more features is or comprises: (i) level of cell viability; (ii) level or activity of a nucleic acid or protein, or form thereof; (iii) microgliosis; (iv) astrocytosis; (v) ATP levels; (vi) Proteasomal function; (vii) Lysosomal function; (viii) oxidative stress; or (ix) inflammation.

The present disclosure provides that a composition as described herein is for use in characterizing an ability of one more microbial strains to modulate one or more metabolites (e.g. microbial metabolites, (e.g. derived from sources other than microbial strains (e.g. synthetically derived), derived from microbial strains)) in a subject.

The present disclosure provides that a use of a composition as described herein is for treating or ameliorating a neurodegenerative disease, disorder, or condition in a subject, wherein a disease, disorder, or condition is associated with one or more metabolites (e.g. microbial metabolites, (e.g. derived from sources other than microbial strains (e.g. synthetically derived), derived from microbial strains)). The present disclosure further provides that a composition as described herein is for use in treating or preventing or ameliorating a neurodegenerative disease, disorder, or condition, comprising one or more components or metabolites, which can be selected from Appendix 1, Appendix 3, or Appendix 4. In some embodiments, a use of a composition as described herein is for treating or ameliorating a disease, disorder, or condition. In some embodiments, a use of a composition as described herein is for treating or ameliorating a disease, disorder, or condition selected from ALS, AD, PD, or HD. In some embodiments, a use of a composition as described herein is for treating or ameliorating ALS.

The present disclosure provides a method of screening a microbial strain, comprising contacting a microbial strain to a culture comprising nerve cells or neuronal cell lines that model a neurodegenerative disease, disorder, or condition, and determining whether a microbial strain altered a feature of a culture, wherein a feature is associated with a neurodegenerative disease, disorder, or condition.

In some embodiments, a step of determining comprises comparing a feature before and after performance of the step of contacting. In some embodiments, a step of determining comprises comparing a feature after the step of contacting with a comparable reference.

In some embodiments, a comparable reference is a historical reference. In some embodiments, a comparable reference is a negative control reference. In some embodiments, a comparable reference is a positive control reference.

In some embodiments, a feature is a level of cell viability. In some embodiments, a feature is level or activity of a nucleic acid or protein, or form thereof. In some embodiments, a feature is or comprises microgliosis. In some embodiments, a feature is or comprises astrocytosis. In some embodiments, a feature is or comprises ATP levels. In some embodiments, a feature is or comprises Proteasomal function. In some embodiments, a feature is or comprises Lysosomal function. In some embodiments, a feature is or comprises oxidative stress.

In some embodiments, a microbial strain or a metabolite altered one or more features of a culture. In some embodiments, one or more features is associated with a neurodegenerative disease, disorder, or condition as described herein. In some embodiments, one or more features is or comprises (i) level of cell viability; (ii) level or activity of a nucleic acid or protein, or form thereof; (iii) microgliosis; (iv) astrocytosis; (v) ATP levels; (vi) Proteasomal function; (vii) Lysosomal function; (viii) oxidative stress; or (ix) inflammation.

The present disclosure provides a method comprising administering to a subject in need thereof a composition comprising one or more microbial strains, components thereof, or metabolites thereof. In some embodiments, the present disclosure provides a method comprising administering to a subject in need thereof a composition comprising one or more components or metabolites. In some embodiments, metabolites can be from one or more microbial strains. In some embodiments, metabolites can be from a source that is not a microbial strain, e.g., synthetically generated.

In some embodiments, a microbial strain may alter a feature of the subject. In some embodiments, a feature is a level of cell viability. In some embodiments, a feature is level or activity of a nucleic acid or protein, or form thereof. In some embodiments, a feature is or comprises microgliosis. In some embodiments, a feature is or comprises astrocytosis. In some embodiments, a feature is or comprises ATP levels. In some embodiments, a feature is or comprises Proteasomal function. In some embodiments, a feature is or comprises Lysosomal function. In some embodiments, a feature is or comprises oxidative stress.

In some embodiments, a microbial strain may alter one or more features of a subject. In some embodiments, one or more features is or comprises (i) level of cell viability; (ii) level or activity of a nucleic acid or protein, or form thereof;

(iii) microgliosis; (iv) astrocytosis; (v) ATP levels; (vi) Proteasomal function; (vii) Lysosomal function; (viii) oxidative stress; or (ix) inflammation.

In some embodiments, a feature is associated with a neurodegenerative disease, disorder, or condition.

The present disclosure provides a method of characterizing a microbial strain, comprising adding a microbial strain to a culture comprising nerve cells or neuronal cell lines that model a neurodegenerative disease, disorder, or condition, and determining whether a microbial strain affects levels of one or more features of nerve cells or neuronal cell lines, wherein one or more features are associated with a neurodegenerative disease, disorder, or condition.

The present disclosure provides a method of manufacturing a pharmaceutical treatment comprising characterizing one or more microbial strains, components, or metabolites thereof comprising the steps of adding one or more microbial strains to a culture comprising nerve cells or neuronal cell lines that model a neurodegenerative disease, disorder, or condition, and determining whether one or more microbial strains affect levels of one or more features of the nerve cells or neuronal cell lines, wherein one or more features are associated with a neurodegenerative disease, disorder, or condition.

The present disclosure provides a method of manufacturing a pharmaceutical treatment comprising adding one or more microbial strains, components, or metabolites (e.g. metabolites derived from different sources (e.g. from microbial strains, synthetically etc.)) thereof, to a syrup, a liquid, a tablet, a troche, a gummy, a capsule, a powder, a gel, a film, an injection, or an eye drop.

The present disclosure provides a method of assessing a microbial strain for an ability to affect one or more features of a culture, comprising adding a microbial strain to a culture comprising nerve cells or neuronal cell lines that model a neurodegenerative disease, disorder, or condition, and determining whether a microbial strain affects levels of one or more features of nerve cells or neuronal cell lines, wherein one or more features are associated with a neurodegenerative disease, disorder, or condition.

In some embodiments, a method further comprises before adding a microbial strain to the culture, determining levels of one or more features of nerve cells or neuronal cell lines in a culture; after adding a microbial strain to a culture, determining levels of the same one or more features of nerve cells or neuronal cell lines in a culture; and comparing levels of one or more features determined before adding a microbial strain with levels of one or more features determined after adding a microbial strain.

In some embodiments, a one or more features includes (i) viability of cells; (ii) level or activity of a nucleic acid or protein, or form thereof; (iii) microgliosis; (iv) ATP levels; (v) inflammation; (vi) astrocytosis; (vii) Proteasomal Function; (viii) Lysosomal Function; (ix) Oxidative Stress; or (x) a combination thereof.

The present disclosure provides that a composition as described herein is for use in treating or preventing a neurodegenerative disease, disorder, or condition, comprising one or more microbial strains, components thereof, or metabolites thereof. In some embodiments, a composition, as described herein, is for use in treating or preventing a neurodegenerative disease, disorder, or condition, comprising one or more metabolites (e.g. derived from sources other than microbial strains (e.g. synthetically derived), metabolites derived from microbial strains).

The present disclosure provides that a composition as described herein is for use in treating or preventing a neurodegenerative disease, disorder, or condition, comprising one or more microbial strains, components thereof, or metabolites thereof, wherein a one or more components or metabolites of a one or more microbial strains are selected from Appendix 1, Appendix 3, or Appendix 4. The present disclosure further provides that a composition as described herein is for use in treating or preventing a neurodegenerative disease, disorder, or condition, comprising one or more components or metabolites, which can be selected from Appendix 1, Appendix 3, or Appendix 4.

In some embodiments, metabolites can be from one or more microbial strains. In some embodiments, metabolites can be from a source that is not a microbial strain, e.g., synthetically generated. In some embodiments, a one or more components or metabolites (e.g. of one or more microbial strains) is a bile acid. In some embodiments, a one or more components or metabolites (e.g. of one or more microbial strains) is Tauroursodeoxycholic acid. In some embodiments, one or more components or metabolites is Butyrylcarnitine, Theobromine, p-Hydroxyphenylpyruvic acid, Propionic acid, Picolinic acid, 2-Hydroxy-4methylvaleric acid, N6-Acetyllysine, Urocanic acid, N5-Ethylglutamine, Trigonelline, Stachydrine, Ectoine, 5-Hydroxylysine, Arginine (arg), Cholic acid, 2-(4-Hydroxyphenyl)propionic acid, N-Acetyltryptophan, Hydroxyproline, Argininosuccinic acid, Glutamic acid (Glu), Sarcosine, 5-Methoxyindoleacetic acid, Indole-3-lactic acid, Isovalerylalanine, N-Acetylleucine, 1-Methylhistidine, N-Acetylphenylalanine, Proline (Pro), or any combination thereof. In some embodiments, one or more components or metabolites is 4-Hydroxyphenylpyruvic, Ectoine, Gramine, N-Acetyl-L-phenylalanine, Nepsilon-Acetyl-L-lysine, Stachydrine, Trigonelline, 3-Ureidopropionic acid, Theobromine, Hippuric acid, Imidazolepropionic acid, NG-Methyl-L-arginine, trans-Urocanic Acid, N-Acetyl-L-leucine, Sarcosine, Isobutyrylcarnitine, b-Hydroxyisovaleric acid, L-Theanine/N5-Ethylglutamine, 5-Hydroxylysine, Phenaceturic acid, betaine, hydroxyproline, Picolinic acid, 2-Aminoadipic acid, Glycerophosphocholine, carnitine, Glycerol 3-phosphate, Argininosuccinic acid, creatine, Terephthalic acid, Homocitrulline, Mucic acid, Homocysteinesulfinic acid, Trimethyllysine, Spermidine, Glyoxylic acid, XA0013 C6H604S, 3-Indoxylsulfuric acid, Nicotinamide, N-Formylglycine, Ureidoglycolate, N-Methylproline, Glucaric acid, Butyrylcarnitine, Methionine sulfoxide, Carboxymethyllysine, Glycolic acid, Phenaceturic acid, Diethanolamine, Phosphorylcholine, Guanidinosuccinic acid, N-Acetylhistidine, Glyceric acid, S-Methylmethionine, Cysteine glutathione disulfide, Kynurenine, N-Acetylphenylalanine, Threonic acid, Malic acid, 7,8-Dihydrobiopterin, Homovanillic acid, Taurocholic acid, 5-Methoxyindoleacetic acid, butyrate, b-Hydroxyisovaleric acid, 2-Oxoglutaric acid, N-Acetyltryptophan, Thiaproline, Hypotaurine, Cholic acid, Acetoacetic acid, Ethanolamine, Guanidoacetic acid, S-Sulfocysteine, Myristic acid C14:0 XA0027, or any combination thereof.

In some embodiments, a composition as described herein is for use in treating or preventing a neurodegenerative disease, disorder, or condition, comprising one or more microbial strains, components thereof, or metabolites thereof.

In some embodiments, a composition comprises one or more microbial strains selected from *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp., or a combination thereof. In some embodiments, a composition as described herein is for use as described herein and comprises one or more microbial strains selected from *Gluconacetobacter hanseni, Terrisporobacter glycolicus, Coprococcus* sp., *Lactobacillus plantarum, Veillonella atypica, Bifidobacterium* sp., or a combination thereof. In some embodiments, a composition as described herein is for use as described herein and comprises a microbial strain. In some embodiments, a composition as described herein is for use as described herein and comprises a microbial strain is *Bacillus subtilis*. In some embodiments, a composition as described herein is for use as described herein and comprises at least two microbial strains selected from a group consisting of *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp., or a combination thereof. In some embodiments, a composition as described herein is for use as described herein and comprises at least two microbial strains selected from a group consisting of *Gluconacetobacter hanseni, Terrisporobacter glycolicus, Coprococcus* sp., *Lactobacillus plantarum, Veillonella atypica, Bifidobacterium* sp., or a combination thereof. In some embodiments, a composition as described herein is for use as described herein and comprises at least five microbial strains selected from a group consisting of *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp., or a combination thereof. In some embodiments, a composition as described herein is for use as described herein and comprises at least five microbial strains selected from a group consisting of *Gluconacetobacter hanseni, Terrisporobacter glycolicus, Coprococcus* sp., *Lactobacillus plantarum, Veillonella atypica, Bifidobacterium* sp., or a combination thereof. In some embodiments, a composition as described herein is for use as described herein and comprises or consists of *Gluconacetobacter hansenii, Terrisporobacter glycolicus, Coprococcus* sp., *Lactobacillus plantarum, Clostridium butyricum, Paenibacillus* sp., *Veillonella* sp., *Bifidobacterium* sp., *Bacillus subtilis*, Acidaminococcus sp. In some embodiments, a composition as described herein is for use as described herein and comprises or consists of *Gluconacetobacter hanseni, Terrisporobacter glycolicus, Coprococcus* sp., *Lactobacillus plantarum, Veillonella atypica, Bifidobacterium*.

The present disclosure provides an injection comprising a composition as described herein.

The present disclosure provides a food supplement comprising a composition as described herein.

The present disclosure provides a kit comprising a composition as described herein for use in treating or preventing a neurodegenerative disease, disorder, or condition.

The present disclosure provides, among other things, a method of treating amyloid plaques or reducing plaque burden, plaque number, or plaque size in a subject diagnosed with a neurodegenerative disease, disorder, or condition. In some embodiments, a method, as described herein comprises administering to a subject in need thereof a composition comprising one or more microbial strains or microbial components thereof. In some embodiments, a method, as described herein comprises administering to a subject in need thereof a composition comprising one or more microbial metabolites. In some embodiments, a neurodegenerative disease, disorder, or condition is Amyotrophic lateral sclerosis (ALS), Alzheimer's Disease (AD), Parkinson's Disease (PD), or Huntington's Disease (HD). In some embodiments, a neurodegenerative disease, disorder, or condition is AD.

In some embodiments, amyloid plaques are located in the brain of a subject. In some embodiments, amyloid plaques are located in the cortex of the brain of a subject. In some embodiments, amyloid plaques are located in the hippocampus of the brain of a subject. In some embodiments, amyloid plaques are located in the cortex and hippocampus of the brain of a subject.

In some embodiments, after the step of administering a composition as described herein, microglia in the brain of a subject is reduced. In some embodiments, after the step of administering a composition as described herein, microglia located within the amyloid plaques in the brain of a subject is reduced.

In some embodiments, plaque burden is reduced by at least 10%, at least 20%, at least 30%, at least 40%, at least 50%, at least 60%, at least 70%, at least 80%, at least 90%, or 100%. In some embodiments, plaque number is reduced by at least 10%, at least 20%, at least 30%, at least 40%, at least 50%, at least 60%, at least 70%, at least 80%, at least 90%, or 100%. In some embodiments, plaque size is reduced by at least 10%, at least 20%, at least 30%, at least 40%, at least 50%, at least 60%, at least 70%, at least 80%, at least 90%, or 100%.

In some embodiments, after the step of administering, a subject shows stabilization or improvement in one or more symptoms associated with a neurodegenerative disease, disorder, or condition. In some embodiments, one or more symptoms associated with a neurodegenerative disease, disorder, or condition is or comprises cognition, memory, logical thinking, mood swings, personality changes, anxiety, aggression, hallucinations, delusions, paranoia, restlessness, agitation, muscle twitches, or attention span.

These, and other aspects encompassed by the present disclosure, are described in more detail below and in the claims.

Definitions

The scope of the present invention is defined by the claims appended hereto and is not limited by certain embodiments described herein. Those skilled in the art, reading the present specification, will be aware of various modifications that may be equivalent to such described embodiments, or otherwise within the scope of the claims. In general, terms used herein are in accordance with their understood meaning in the art, unless clearly indicated otherwise. Explicit definitions of certain terms are provided below; meanings of these and other terms in particular instances throughout this specification will be clear to those skilled in the art from context.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an," as used herein, should be understood to include the plural referents unless clearly indicated to the contrary. Claims or descriptions that include "or" between one or more members of a group are considered satisfied if one, more than one, or all of the group members are present in, employed in, or otherwise relevant to a given product or process unless indicated to the contrary or otherwise evident from the context. In some embodiments, exactly one member of a group is present in, employed in, or otherwise relevant to a given product or process. In some embodiments, more than one, or all group members are present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists (e.g., in Markush group or similar format), it is to be understood that each subgroup of the elements is also disclosed, and any element(s) can be removed from the group. It should be understood that, in general, where embodiments or aspects are referred to as "comprising" particular elements, features, etc., certain embodiments or aspects "consist," or "consist essentially of," such elements, features, etc. For purposes of simplicity, those embodiments have not in every case been specifically set forth in so many words herein. It should also be understood that any embodiment or aspect can be explicitly excluded from the claims, regardless of whether the specific exclusion is recited in the specification.

Administration: As used herein, the term "administration" typically refers to the administration of a composition to a subject or system to achieve delivery of an agent to the subject or system. In some embodiments, the agent is, or is included in, the composition; in some embodiments, the agent is generated through metabolism of the composition or one or more components thereof. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In many embodiments provided by the present disclosure, administration is oral administration. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time. Administration of cells can be by any appropriate route that results in delivery to a desired location in a subject where at least a portion of the delivered cells or components of the cells remain viable. A period of viability of cells after administration to a subject can be as short as a few hours, e.g., twenty-four hours, to a few days, to as long as several years, i.e., long-term engraftment. In some embodiments, administration comprises delivery of a bacterial extract or preparation comprising one or more bacterial metabolites and/or byproducts but lacking fully viable bacterial cells.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Approximately: As applied to one or more values of interest, includes to a value that is similar to a stated reference value. In certain embodiments, the term "approximately" or "about" refers to a range of values that fall within ±10% (greater than or less than) of the stated reference value unless otherwise stated or otherwise evident from the context (except where such number would exceed 100% of a possible value).

Comparable: As used herein, the term "comparable" refers to two or more agents, entities, situations, sets of conditions, subjects, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Conservative: As used herein, refers to instances when describing a conservative amino acid substitution, including a substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T);

amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, which is incorporated herein by reference in its entirety. In some embodiments, a substitution is a moderately conservative substitution wherein the substitution has a nonnegative value in the PAM250 log-likelihood matrix.

ing, assaying and analyzing are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

Dosage form: Those skilled in the art will appreciate that the term "dosage form" may be used to refer to a physically discrete unit of an agent (e.g., a therapeutic agent) for administration to a subject. Typically, each such unit contains a predetermined quantity of agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate

CONSERVATIVE AMINO ACID SUBSTITUTIONS

| For Amino Acid | Code | Replace With |
|---|---|---|
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Control: As used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" also includes a "control animal." A "control animal" may have a modification as described herein, a modification that is different as described herein, or no modification (i.e., a wild-type animal). In one experiment, a "test" (i.e., a variable being tested) is applied. In a second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Determining, measuring, evaluating, assessing, assaying and analyzing: Determining, measuring, evaluating, assess-that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population.

Engineered: In general, the term "engineered" refers to the aspect of having been manipulated by the hand of man. For example, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Excipient: As used herein, refers to an inactive (e.g., non-therapeutic) agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Gene: As used herein, refers to a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity, we note that, as used in the present disclosure, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

Improve, increase, enhance, inhibit or reduce: As used herein, the terms "improve," "increase," "enhance," "inhibit," "reduce," or grammatical equivalents thereof, indicate values that are relative to a baseline or other reference measurement. In some embodiments, a value is statistically significantly difference that a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment. In some embodiments, an appropriate reference is a negative reference; in some embodiments, an appropriate reference is a positive reference.

Isolated: As used herein, refers to a substance and/or entity that has been (1) separated from at least some of the components with which it was associated when initially produced (whether in nature and/or in an experimental setting), and/or (2) designed, produced, prepared, and/or manufactured by the hand of man. In some embodiments, an isolated substance or entity may be enriched; in some embodiments, an isolated substance or entity may be pure. In some embodiments, isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "enriched", "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. Those skilled in the art are aware of a variety of technologies for isolating (e.g., enriching or purifying) substances or agents (e.g., using one or more of fractionation, extraction, precipitation, or other separation).

Level: As used herein, the term "level" refers to a scale of amount or quantity of a substance (e.g., a metabolite). In some embodiments, a level can be simply the presence or absence of a substance. A level of a substance may be represented in multiple ways or formats. For example, in some embodiments, a level may be represented as a percentage (%), a measure of weight (e.g., mg, μg, ng, etc.), a measure of concentration (e.g., mg/mL, μg/mL, ng/mL, etc.), a measure of volume (e.g., mL, μL, nL, etc.), in % change, etc.

Metabolite: As used herein, the term "metabolite" refers to a substance (e.g., a small molecule, macromolecule, organic compound, or inorganic compound) made or used during metabolism. Metabolism is generally understood as a process by which a substance (e.g., food, drug, chemical, cell, or tissue) is chemically broken down. In some embodiments, a metabolite is an end product. In some embodiments, a metabolite is an intermediate. Exemplary metabolites are provided herein, e.g., in Appendix 1-1, 1-3, and 3. Exemplary metabolic pathways are provided herein, e.g., in Appendix 1-2. In some embodiments, a metabolite may be produced or made by an organism. In some embodiments, a metabolite may be produced or made by a microorganism (e.g. microbial strain). In some embodiments, a microbial metabolite produced or made by a microbial strain. In some embodiments, a metabolite may be produced or made naturally (e.g. by an organism (e.g. microorganism (e.g. microbial strain))). In some embodiments, a metabolite may be produced or made synthetically (e.g. from a source that is not a microbial strain (e.g., synthetically generated)).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: ophthalmic administration, intravitreal administration, suprachoroidal administration, oral administration, subcutaneous administration, intravenous administration, intramuscular administration, intracerebral administration, intrathecal administration, for example, drenches (aqueous or non-aqueous solutions or suspensions), tablets, e.g., those targeted for buccal, sublingual, and systemic absorption, boluses, powders, granules, pastes for application to the tongue, capsules, powders, etc. In some embodiments, an active agent may be or comprise a cell or population of cells (e.g., a culture, for example of an Ellagitannin-Enzyme-Synthesizing (EES) microbe); in some embodiments, an active agent may be or comprise an extract or component of a cell or population (e.g., culture) of cells. In some embodiments, an active agent may be or comprise an isolated, purified, or pure compound. In some embodiments, an active agent may have been synthesized in vitro (e.g., via chemical and/or enzymatic synthesis). In some embodiments, an active agent may be or comprise a natural product (whether isolated from its natural source or synthesized in vitro).

Pharmaceutically acceptable: As used herein, the term "pharmaceutically acceptable" which, for example, may be used in reference to a carrier, diluent, or excipient used to formulate a pharmaceutical composition as disclosed herein, means that the carrier, diluent, or excipient is compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be is "acceptable" in the sense of being compatible with the other ingredients of the formulation and not injurious to the subject (e.g., patient). Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prebiotic: As used herein, a "prebiotic" refers to an ingredient that allows or promotes specific changes, both in the composition and/or activity in the gastrointestinal microbiota that may (or may not) confer benefits upon the host. In some embodiments, a prebiotic can include one or more of the following: the prebiotic comprises a pome extract, berry extract and walnut extract.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. In some embodiments, prevention may be considered complete, for example, when onset of a disease, disorder or condition has been delayed fora predefined period of time.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Risk: As will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90, or up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, plasma, mucous, digestive fluid, stool, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Small molecule: As used herein, the term "small molecule" refers to small organic or inorganic molecules of molecular weight below about 3,000 Daltons. In general, small molecules may have a molecular weight of less than 3,000 Daltons (Da). Small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

Subject: As used herein, the term "subject" refers to an individual to which a provided treatment is administered. In some embodiments, a subject is animal. In some embodiments, a subject is a mammal, e.g., a mammal that experiences or is susceptible to a disease, disorder, or condition as described herein. In some embodiments, an animal is a vertebrate, e.g., a mammal, such as a non-human primate, (particularly a higher primate), a sheep, a dog, a rodent (e.g. a mouse or rat), a guinea pig, a goat, a pig, a cat, a rabbit, or a cow. In some embodiments, an animal is a non-mammal animal, such as a chicken, an amphibian, a reptile, or an invertebrate model *C. elegans*. In some embodiments, a subject is a human. In some embodiments, a subject is suffering from or susceptible to one or more diseases, disorders or conditions as described herein. In some embodiments, a subject displays one or more symptoms of a one or more diseases, disorders or conditions as described herein. In some embodiments, a subject has been diagnosed with one or more diseases, disorders or conditions as described herein. In some embodiments, the subject is receiving or has received certain therapy to diagnose and/or to treat a disease, disorder, or condition. In another embodiment, the subject is an experimental animal or animal substitute as a disease model.

Substantially: As used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to subjects (e.g., patients) in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

of mice. (A) Plot shows fluorescence intensity of microgliosis observed in each group relative to vehicle-treated wild-type mice (i.e. mock treated wild-type mice of group G1). (B) Representative micrographs show fluorescently stained cells of the spinal cord for each of the four groups. As used herein, the terms "CT6" and "CT6m" refer to compositions defined in Tables 2 and 3 below, respectively.

Figure 1A:
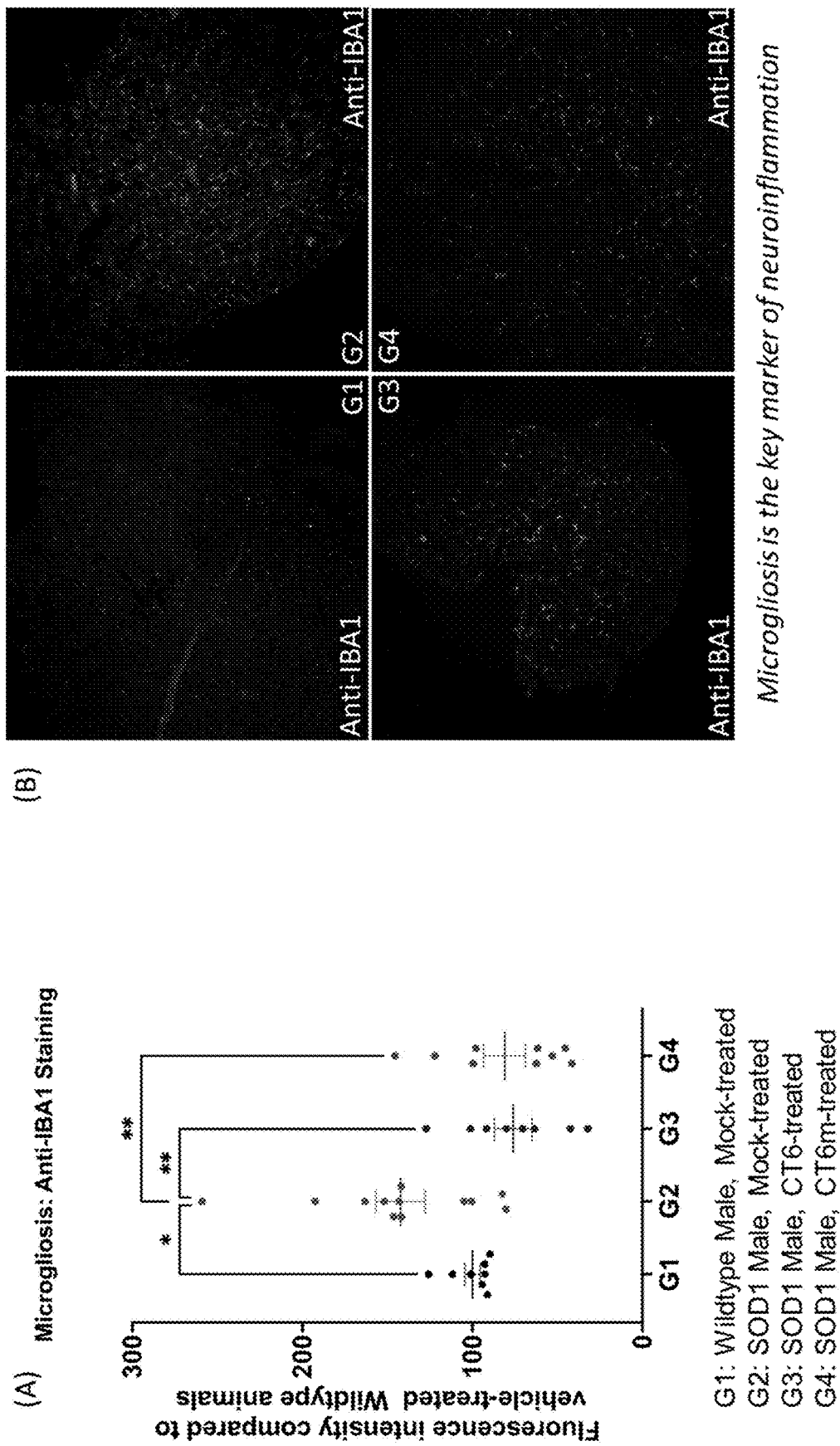
FIG. 1A shows fluorescence data representative of microgliosis in each of the four study groups (G1, G2, G3, and G4)
Figure 1B:
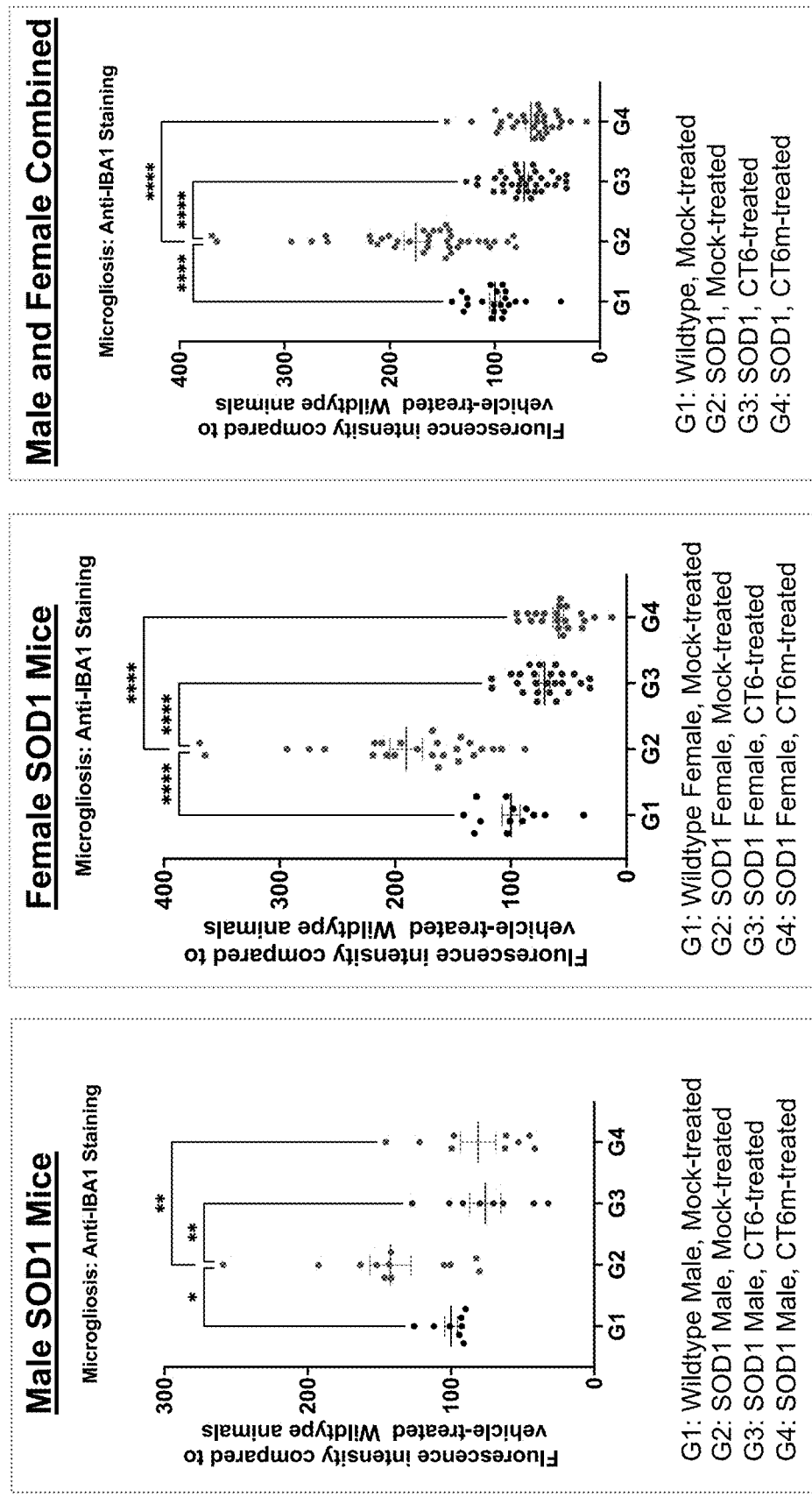

FIG. 1B shows fluorescence data representative of microgliosis in each of the four study groups (G1, G2, G3, and G4) of male, female, and male and female mice. Image quantification was performed using ImageJ analysis software. Average of fluorescence values from G1 group was calculated and the % change in the fluorescence compared to that of the G1 group average were plotted. Scatter dot blots were prepared in GraphPad Prism. The scatter dot blot shows Mean±SEM values. Each dot represents % fluorescence of a single image compared to that of G1 group. Statistical analyses were performed in GraphPad Prism. Data sets were analyzed by one-way ANOVA followed by Dunnett's test. A level of $p<0.05$ was considered statistically significant. Compared to the male G2 group, male G3 or male G4 respectively had significantly different levels (*$p=0.04$ and $p=0.001$). Compared to the female G2 group, female G3 or female G4 respectively had significantly different levels (**$p<0.0001$).

Figure 2A:
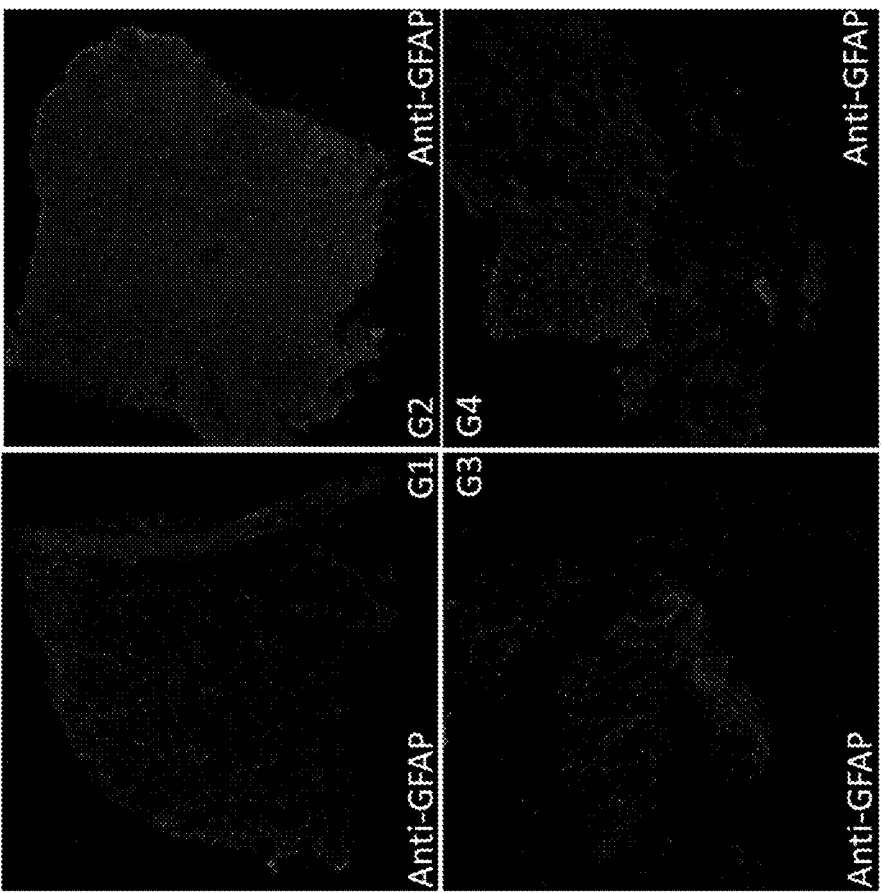
Figure 2A:
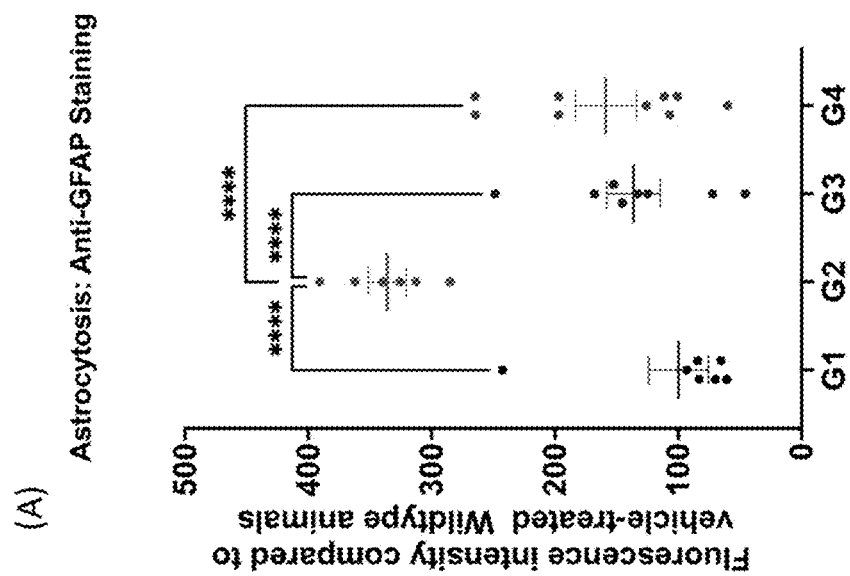

FIG. 2A shows fluorescence data representative of astrocytosis in each of the four study groups (G1, G2, G3, and G4) of mice. (A) Plot shows fluorescence intensity of astrocytosis observed in each group relative to vehicle-treated wild-type mice (i.e., mock treated wild-type mice of group G1). (B) Representative micrographs shows fluorescently stained cells of the spinal cord for each of the four groups.

Figure 2B:
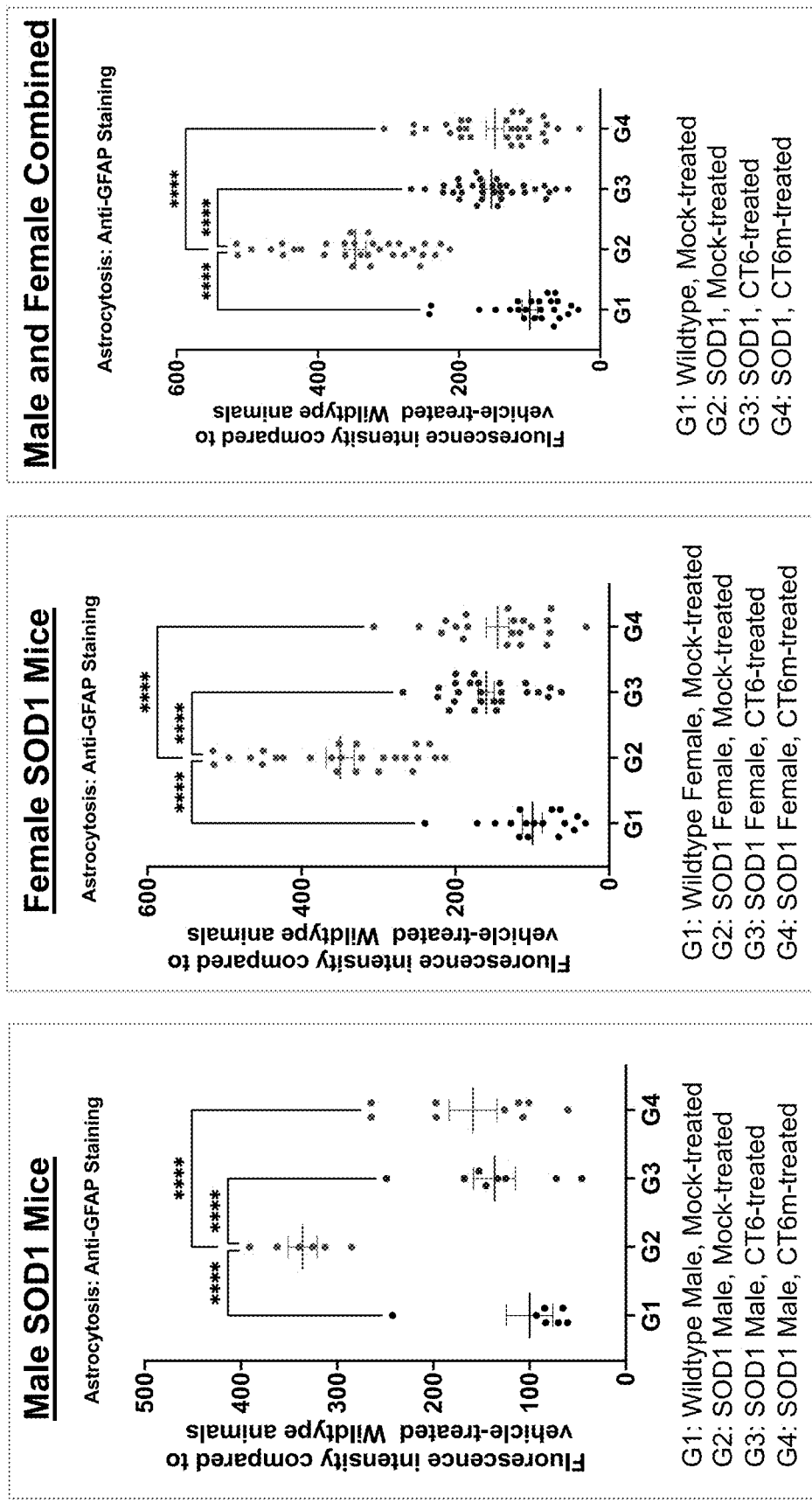

FIG. 2B shows fluorescence data representative of astrocytosis in each of the four study groups (G1, G2, G3, and G4) of male, female, and male and female mice. Image quantification was performed using ImageJ analysis software. Average of fluorescence values from G1 group was calculated and the % change in the fluorescence compared to that of the G1 group average were plotted. Scatter dot blots were prepared in GraphPad Prism. The scatter dot blot shows Mean±SEM values. Each dot represents % fluorescence of a single image compared to that of G1 group. Statistical analyses were performed in GraphPad Prism. Data sets were analyzed by one-way ANOVA followed by Dunnett's test. A level of $p<0.05$ was considered statistically significant. Compared to the male or female G2 group, male or female G3 and male or female G4 respectively had significantly different GFAP levels (****$p<0.0001$).

Figure 3:
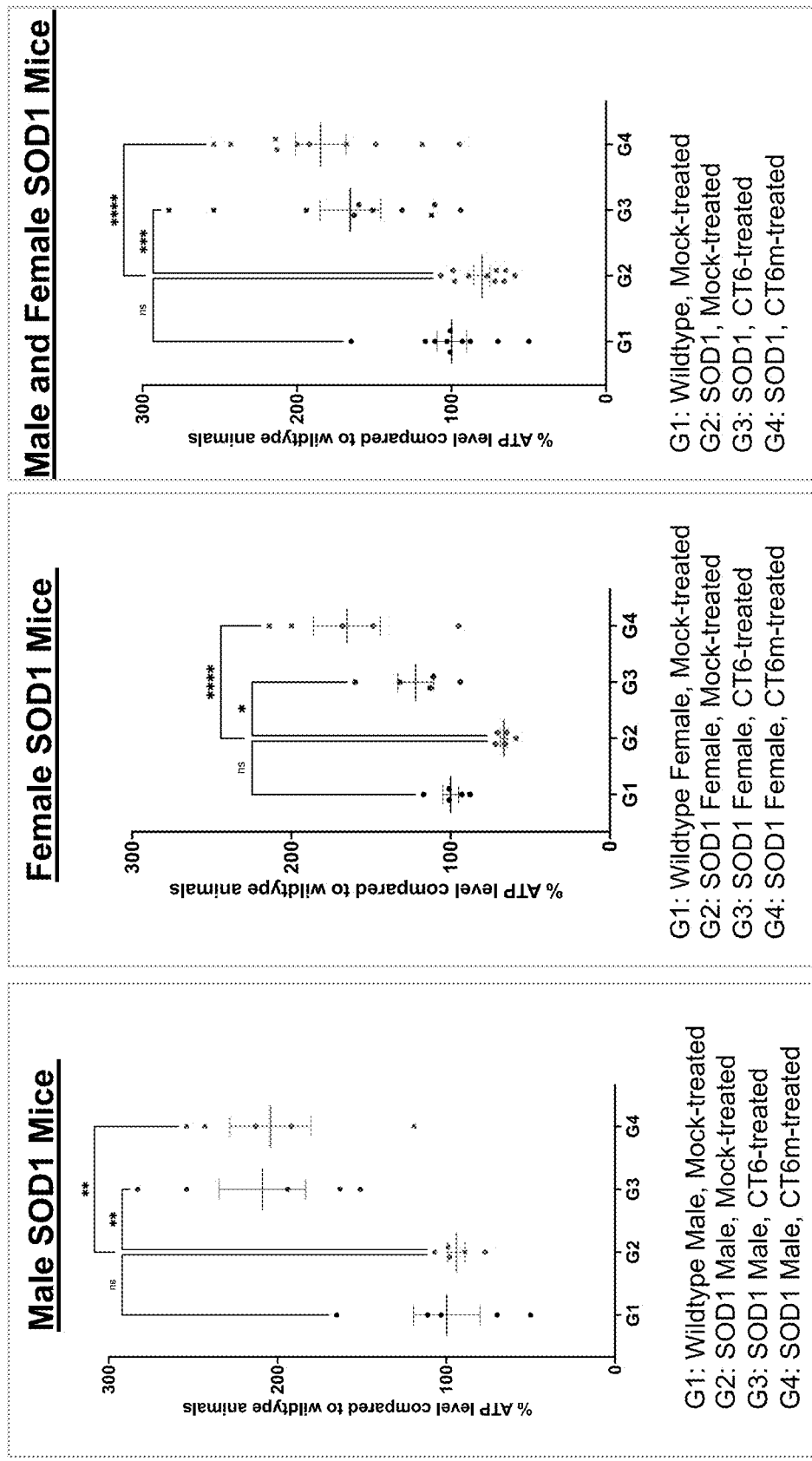

FIG. 3 shows % ATP level of each group relative to wild-type vehicle-treated wild-type male, female, and male and female mice (i.e. mock treated wild-type mice of group G1). ATP measurements were conducted on apical spinal cord protein homogenate using Promega CellTiter-Glo. Scatter dot blots were prepared in GraphPad Prism. Each dot represents one spinal cord sample described in Table 3. Data represented as Mean±SEM. The % ATP level was calculated by comparing the luminescence value to the average of G1 group. Statistical analyses were performed in GraphPad Prism. Data sets were analyzed by one-way ANOVA followed by Dunnett's test. A level of $p<0.05$ was considered statistically significant. Compared to the G1 group, G3 and G4 had significantly different ATP levels (*$p=0.03$ $p=0.0029$, *$p=0.0003$, and ****$p<0.0001$). ns denotes no statistically significant difference between G1 and G2 groups.

Figure 4:
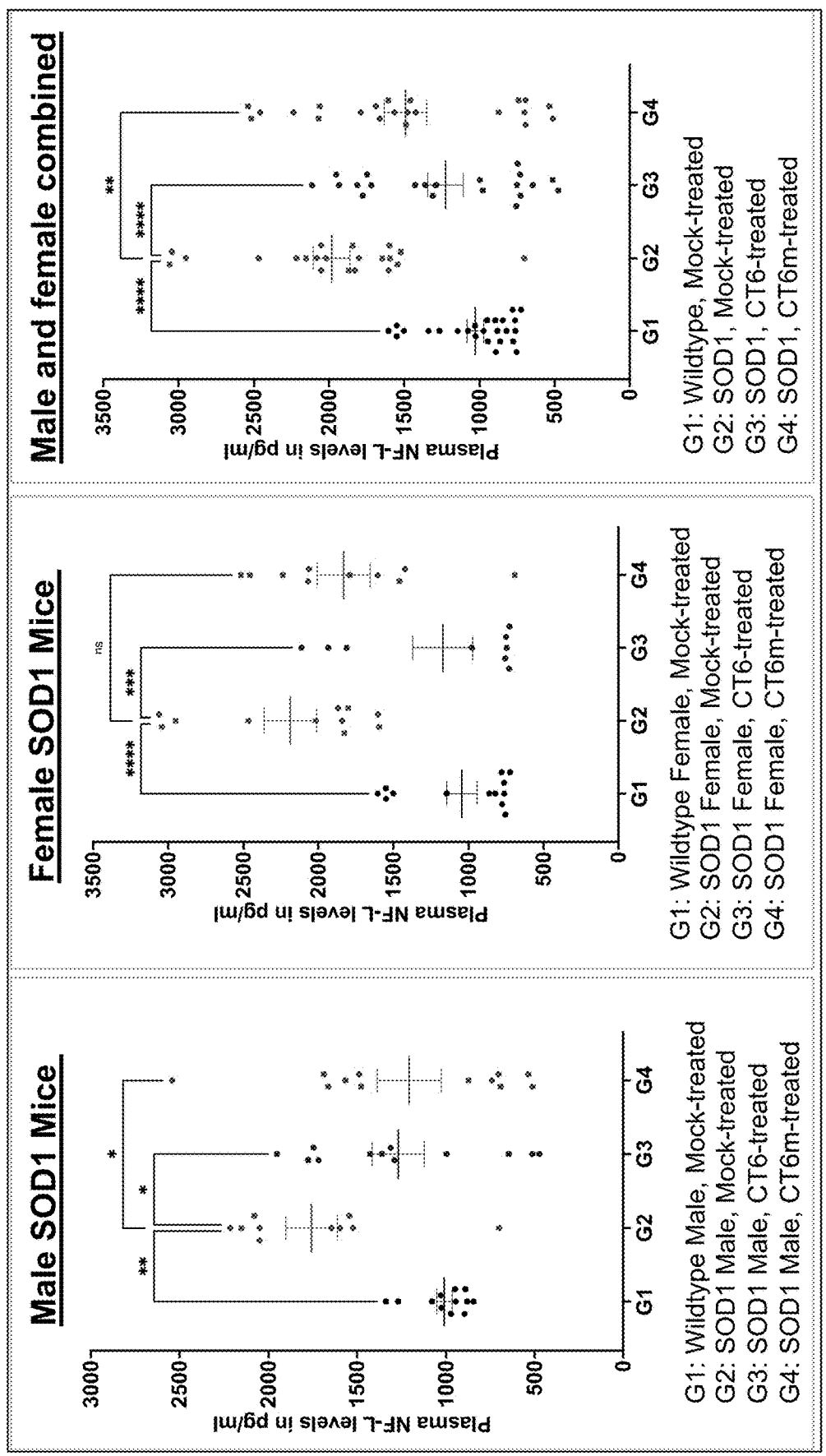

FIG. 4 shows plasma NF-L levels of each group relative to wild-type vehicle-treated wild-type male, female, and male and female mice (i.e. mock treated wild-type mice of group G1). Plasma NF-L levels from the animals were determined using the NF-L ELISA kit. Scatter dot blots were prepared in GraphPad Prism. Each dot represents plasma sample from individual animal. Data represented as Mean±SEM. Statistical analyses were performed in GraphPad Prism. Data sets were analyzed by one-way ANOVA followed by Dunnett's test. A level of $p<0.05$ was considered statistically significant. Compared to the G2 group, G3 and G4 had significantly different NF-L levels (*$p=0.02$ $p=0.0074$, *$p=0.0003$, and ****$p<0.0001$). ns denotes no statistically significant difference between female G2 and G4 groups.

Figure 5:
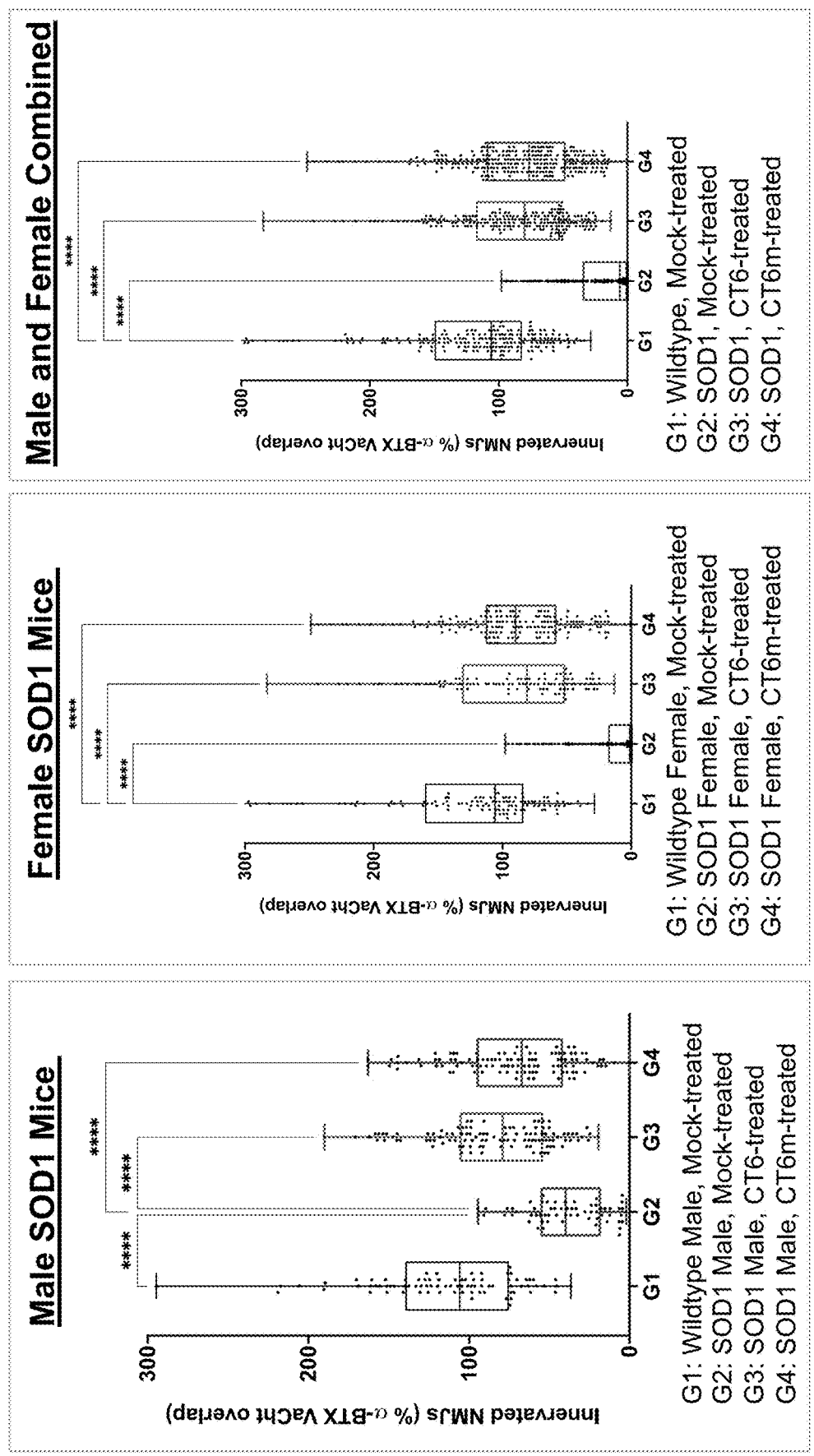

FIG. 5 shows innervated Neuromuscular (NMJ) integrity of each group relative to wild-type vehicle-treated wild-type male, female, and male and female mice (i.e. mock treated wild-type mice of group G1). Each dot in the plot represents NMJ from at least 4 animals. NMJ integrity was measured by determining the overlap between presynaptic (vesicular acetylcholine transporter; VAChT) and postsynaptic (a-bungarotoxin; a-BTX, which binds to the nicotinic acetylcholine transporter). Box and whisker plot were prepared in GraphPad Prism. The middle line in the Box and whisker plot represents the % mean value. SEM was plotted for each group. Each dot represents a single NMJ where the % overlap between VAChT and a-BTX was determined. Statistical analyses were performed in GraphPad Prism. Data sets were analyzed by one-way ANOVA followed by Dunnett's test. A level of $p<0.05$ was considered statistically significant. The innervated NMJs observed in male or female G2 group were significantly different compared to male G1 or female G2 group respectively (**$p<0.0001$). By contrast, the innervated NMJs of male G3 or male G4 or female G3 or female G4 were significantly different from male G2 or female G2 group respectively (**$p<0.0001$).

Figure 6A:
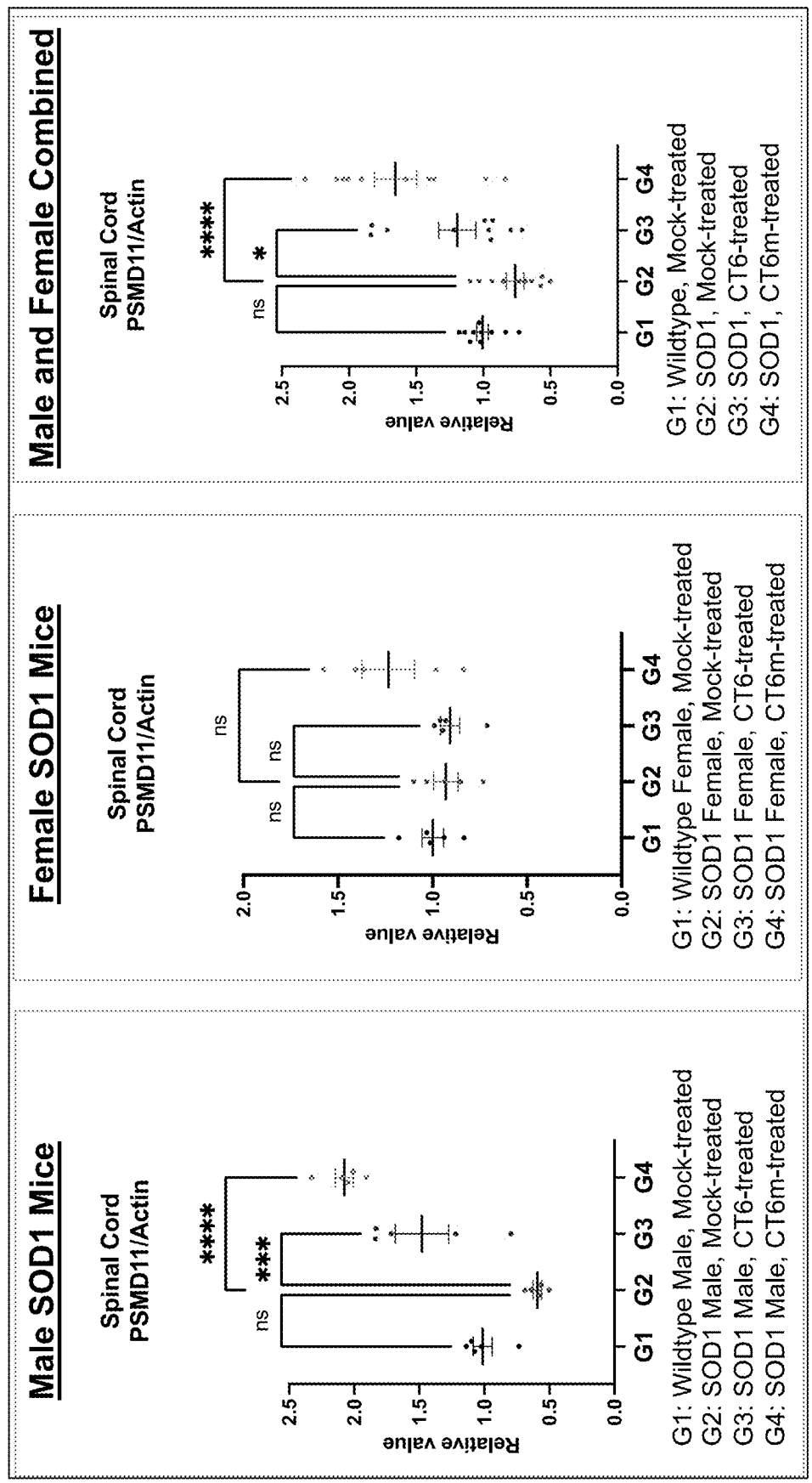

FIG. 6A shows data representative of proteasomal function in each of the four study groups (G1, G2, G3, and G4) of male, female, and male and female mice. Plot shows value of PSMD11 protein levels normalized using their respective b-actin loading controls observed in each group relative to vehicle-treated wild-type male, female, and male and female mice (i.e. mock treated wild-type mice of group G1). Protein bands detected by western blots were normalized using their respective b-actin loading controls. Scatter dot blots were prepared in GraphPad Prism. The scatter dot blot shows Mean±SEM values. Each dot in the figure represents the relative value compared to the G1 group average of a single spinal cord lysate described in Table 3 of Appendix 5. Statistical analyses were performed in GraphPad Prism. Data sets were analyzed by one-way ANOVA followed by Dunnett's test. A level of $p<0.05$ was considered statistically significant. Compared to the male G2 group, the PSMD 11 levels in male G3 or G4 were significantly different (*$p=0.0002$ and **$p<0.0001$). PSMD11 protein levels were not statistically significant between female G1 and G2 or G2 and G3 or G2 and G4 groups. ns denotes no statistical significance. However, when the male and female data were combined, significant differences were found between G2 and G3, and G2 and G4 groups (*$p=0.02$ and ****$p<0.0001$).

Figure 6B:
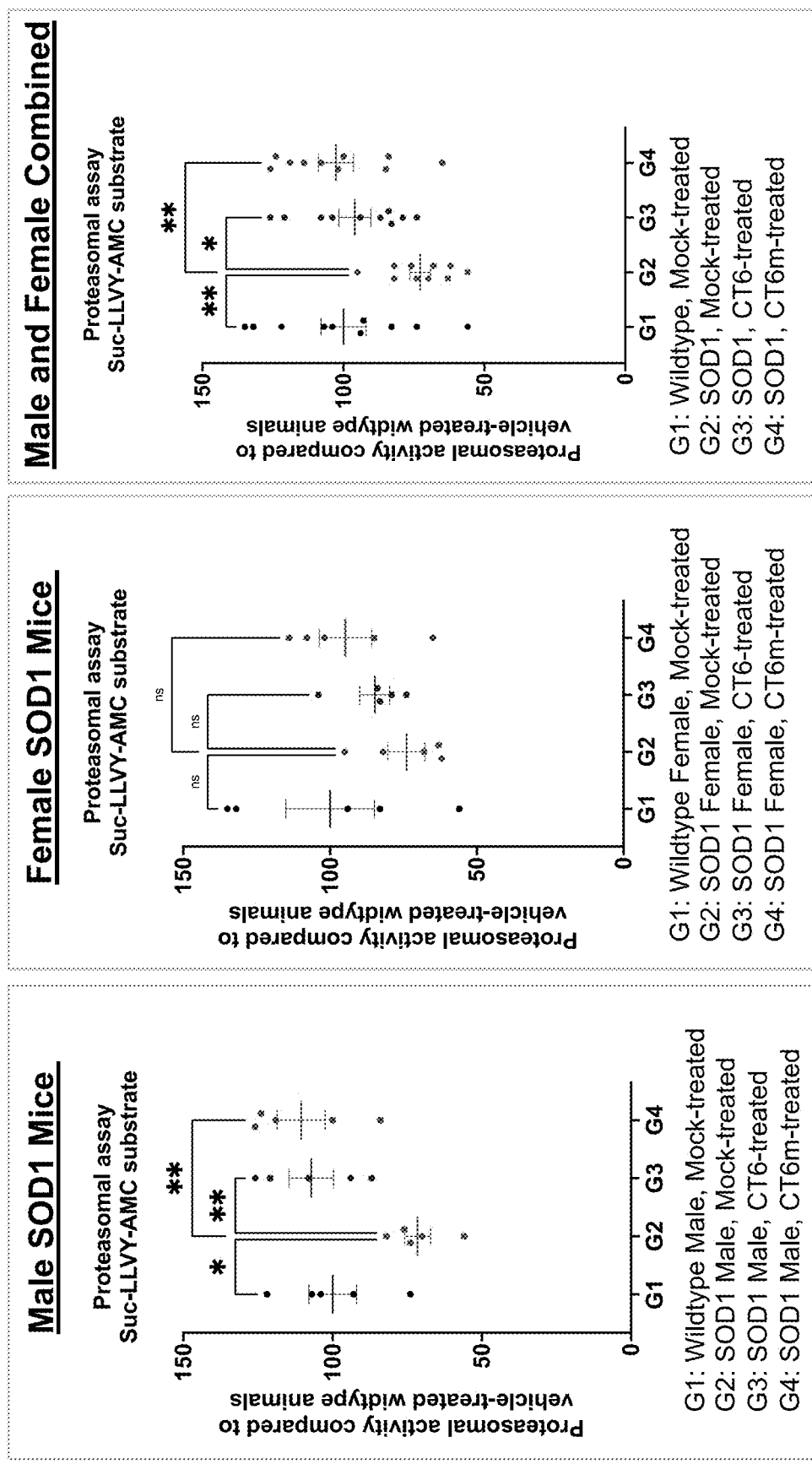

FIG. 6B shows data representative of proteasomal function in each of the four study groups (G1, G2, G3, and G4) of male, female, and male and female mice. Plot shows value of proteasomal activity observed in each group relative to vehicle-treated wild-type male, female, and male and female mice (i.e. mock treated wild-type mice of group G1). Suc-LLVY-AMC substrate was used to measure proteasomal activity. Average of fluorescence values from G1 group was calculated and the % change in the fluorescence compared to that of the G1 group average were plotted. Scatter dot blots were prepared in GraphPad Prism. The scatter dot blot shows Mean±SEM values. Statistical analyses were performed in GraphPad Prism. Data sets were analyzed by one-way ANOVA followed by Dunnett's test. A level of p<0.05 was considered statistically significant. Compared to the G1 group, the G2 group had significantly different levels (*p=0.0377). By contrast, G3 and G4 had significantly different levels of proteasomal activity compared the G2 group (**p<0.01). Proteasomal activity were not significantly different between female G1 and G2 or G2 and G3 or G2 and G4 groups. ns denotes no statistical significance. However, when the male and female data were combined, significant differences were found between G1 and G2 or G2 and G3 or G2 and G4 groups (*p=0.02 and **p=0.009).

Figure 7:
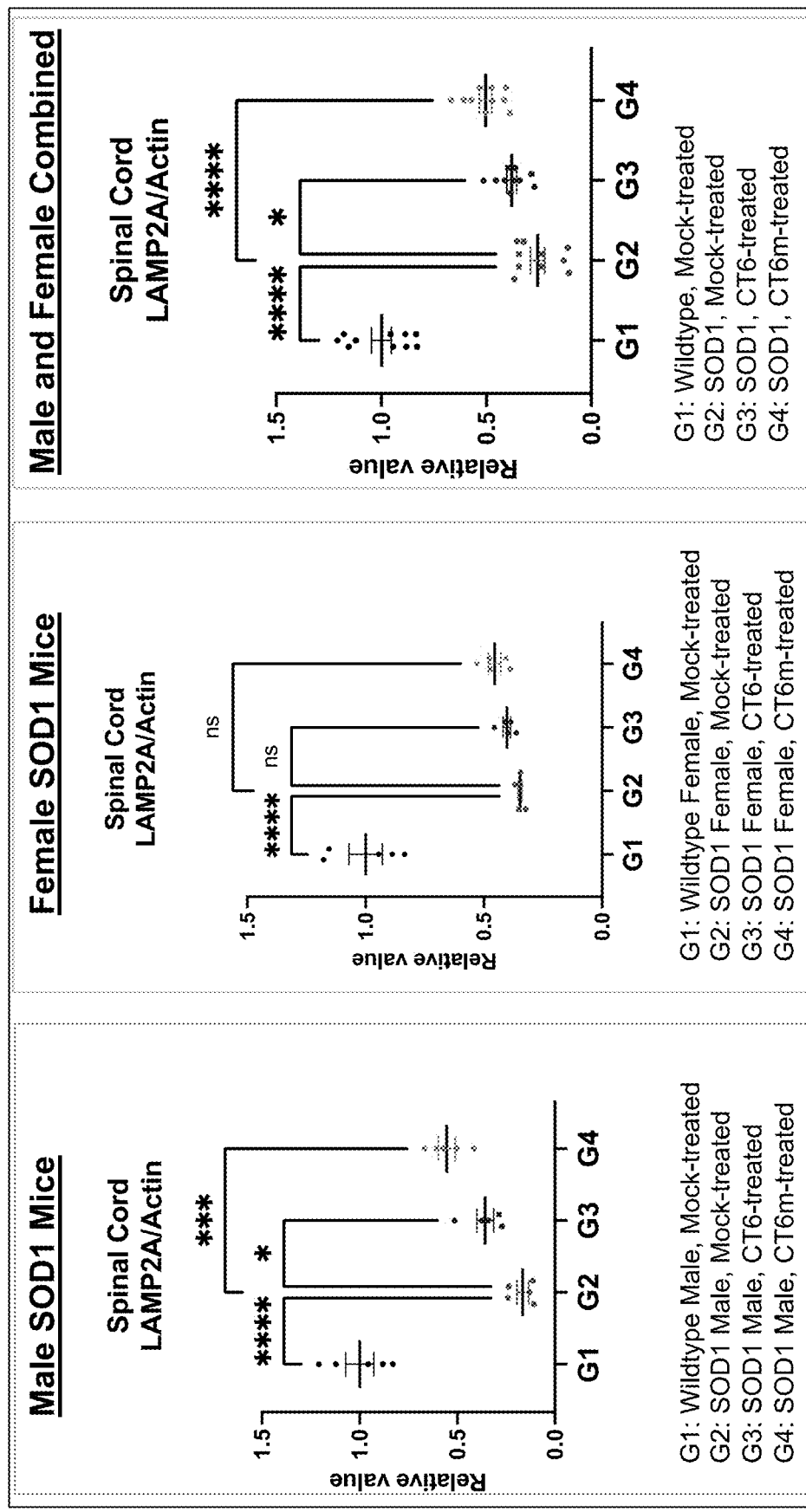

FIG. 7 shows data representative of lysosomal function in each of the four study groups (G1, G2, G3, and G4) of mice. (A) Plot shows value of LAMP2A protein levels normalized using their respective b-actin loading controls observed in each group relative to vehicle-treated wild-type mice (i.e. mock treated wild-type mice of group G1). Protein bands detected by western blots were normalized using their respective b-actin loading controls. Raw data was organized and sorted in Excel. Please see Appendix 5 for raw data. Scatter dot blots were prepared in GraphPad Prism. Each dot in the figure represents a single spinal cord lysate described in Table 3 of Appendix 5. Data represented as Mean±SEM. Statistical analyses were performed in GraphPad Prism. Data sets were analyzed by one-way ANOVA followed by Dunnett's test. A level of p<0.05 was considered statistically significant. Compared to the male G2 group, male G3 and G4 had significantly different levels of LAMP2A (*p=0.03, *p=0.0002 and **p<0.0001). While the LAMP2A protein levels were statistically significant between female G1 and G2, there was no significant difference between female G2 and G3 or female G2 and G4 groups. ns denotes no statistical significance. However, when the male and female data were combined, significant differences were found between G1 and G2, G2 and G3, and G2 and G4 groups (*p=0.04 and ****p<0.0001).

Figure 8:
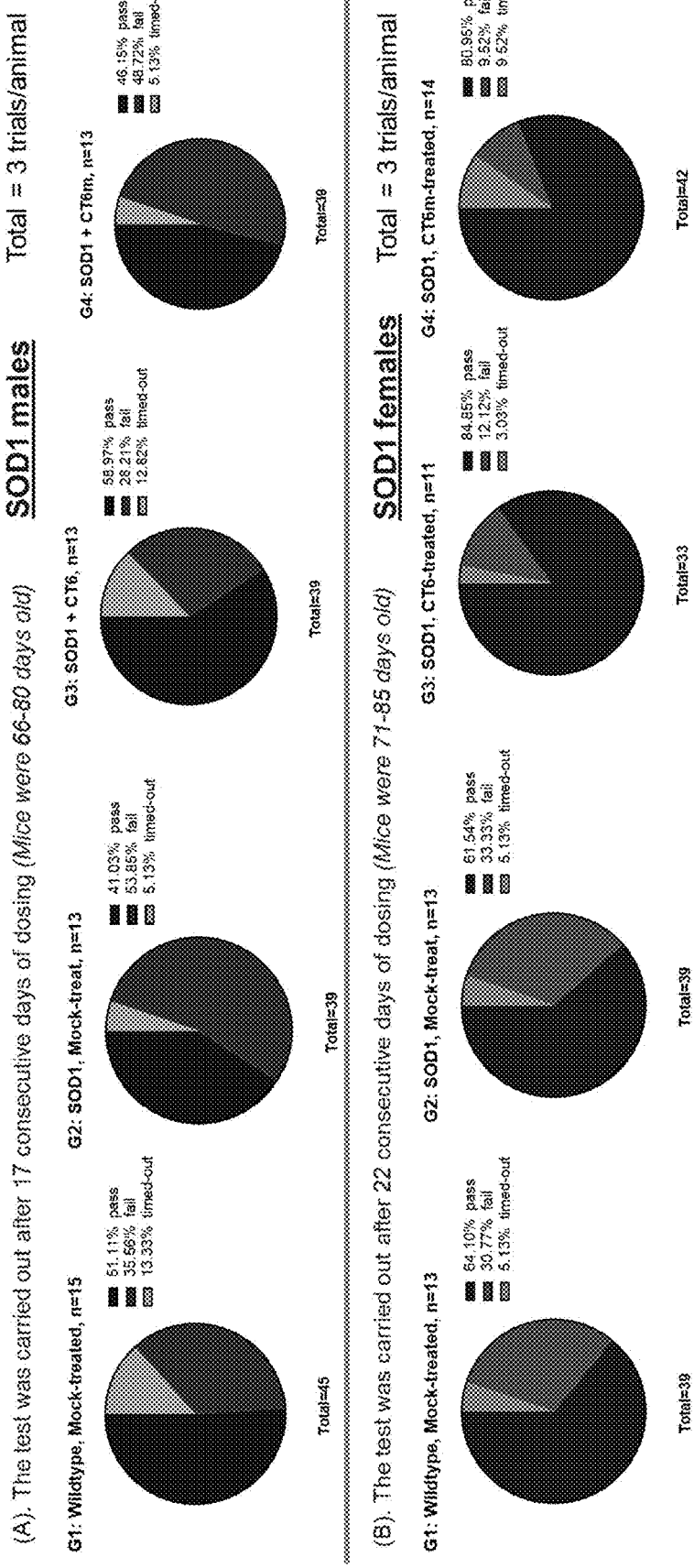

FIG. 8 shows data from Beam Walk tests. (A) Plots show Beam Walk test results for each of the four study groups (G1, G2, G3, and G4) for test performed SOD1 male mice. (B) Plots show Beam Walk test results for each of the four study groups (G1, G2, G3, and G4) for test performed in SOD1 female mice.

Figure 9:
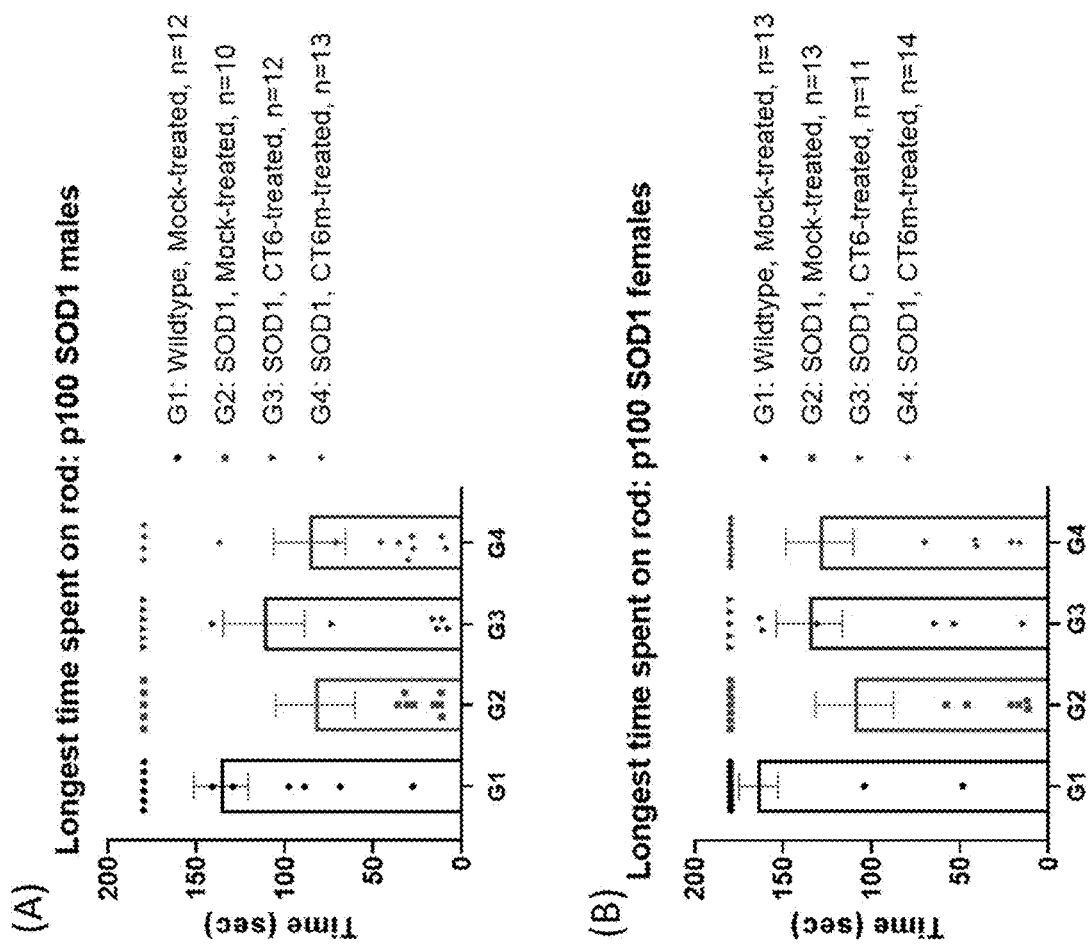

FIG. 9 shows data from P100 Rotarod tests. (A) Plots show P100 Rotarod test results for each of the four study groups (G1, G2, G3, and G4) for test performed in SOD1 male mice. (B) Plots show P100 Rotarod test results for each of the four study groups (G1, G2, G3, and G4) for test performed in SOD1 female mice.

Figure 10:
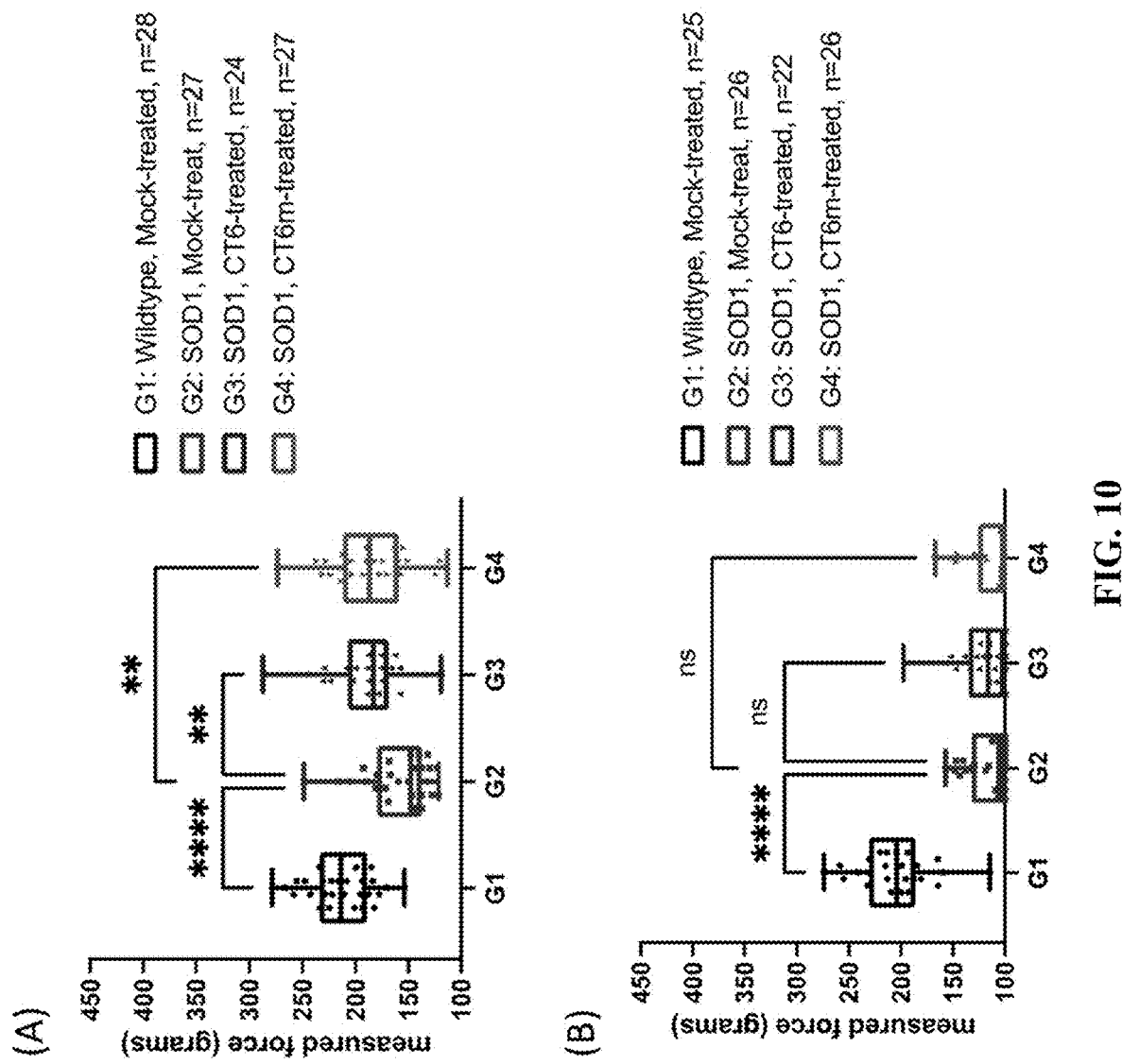

FIG. 10. shows data from Grip Strength tests. (A) Plots show Grip Strength test results (as measured in force in grams) for each of the four study groups (G1, G2, G3, and G4) for test performed in SOD1 male mice. (B) Plots show Grip Strength test results (as measured in force in grams) for each of the four study groups (G1, G2, G3, and G4) for test performed in SOD1 female mice.

Figure 11:
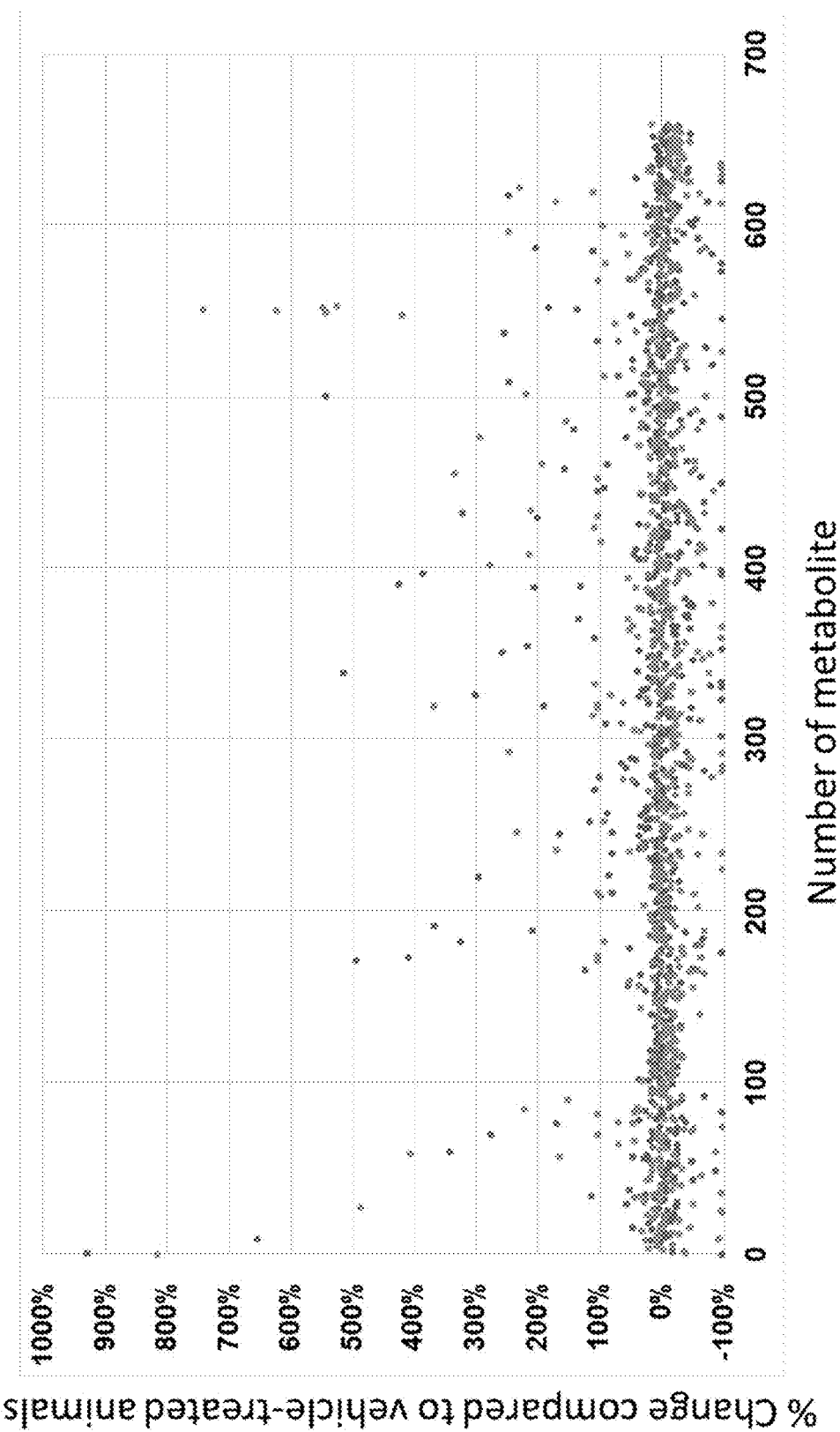

FIG. 11 shows metabolomics analysis of CT6-treated wild-type male and female mice. Plot shows % change of metabolite levels relative to vehicle-treated mice for 660 metabolites identified in mouse plasma (blue: male mice; orange: female mice).

Figure 12:
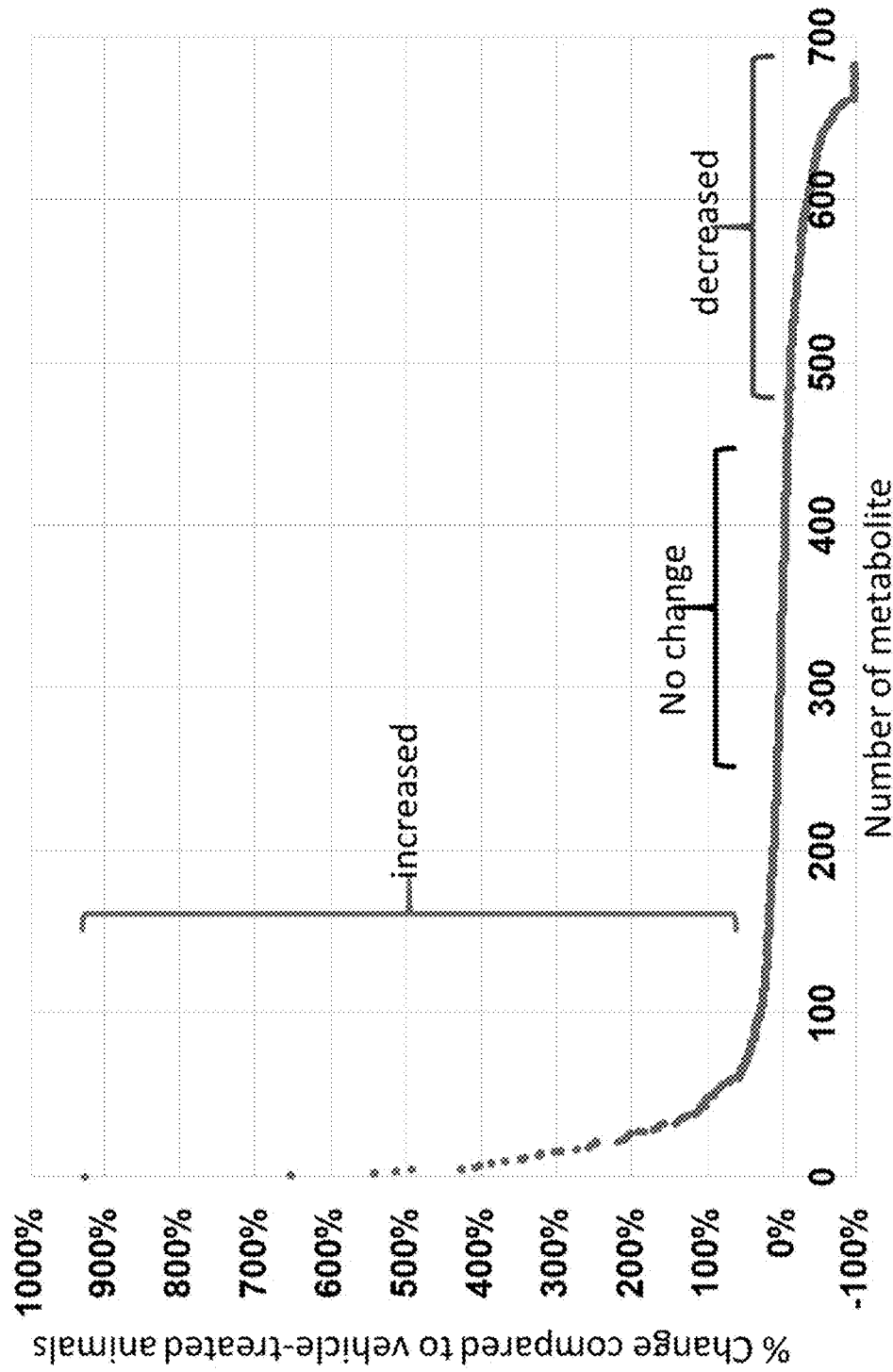

FIG. 12 shows metabolomics analysis of CT6-treated wild-type male mice. Plot shows % change of metabolite levels relative to vehicle-treated male mice for about 660 to about 700 metabolites identified in mouse plasma.

Figure 13:
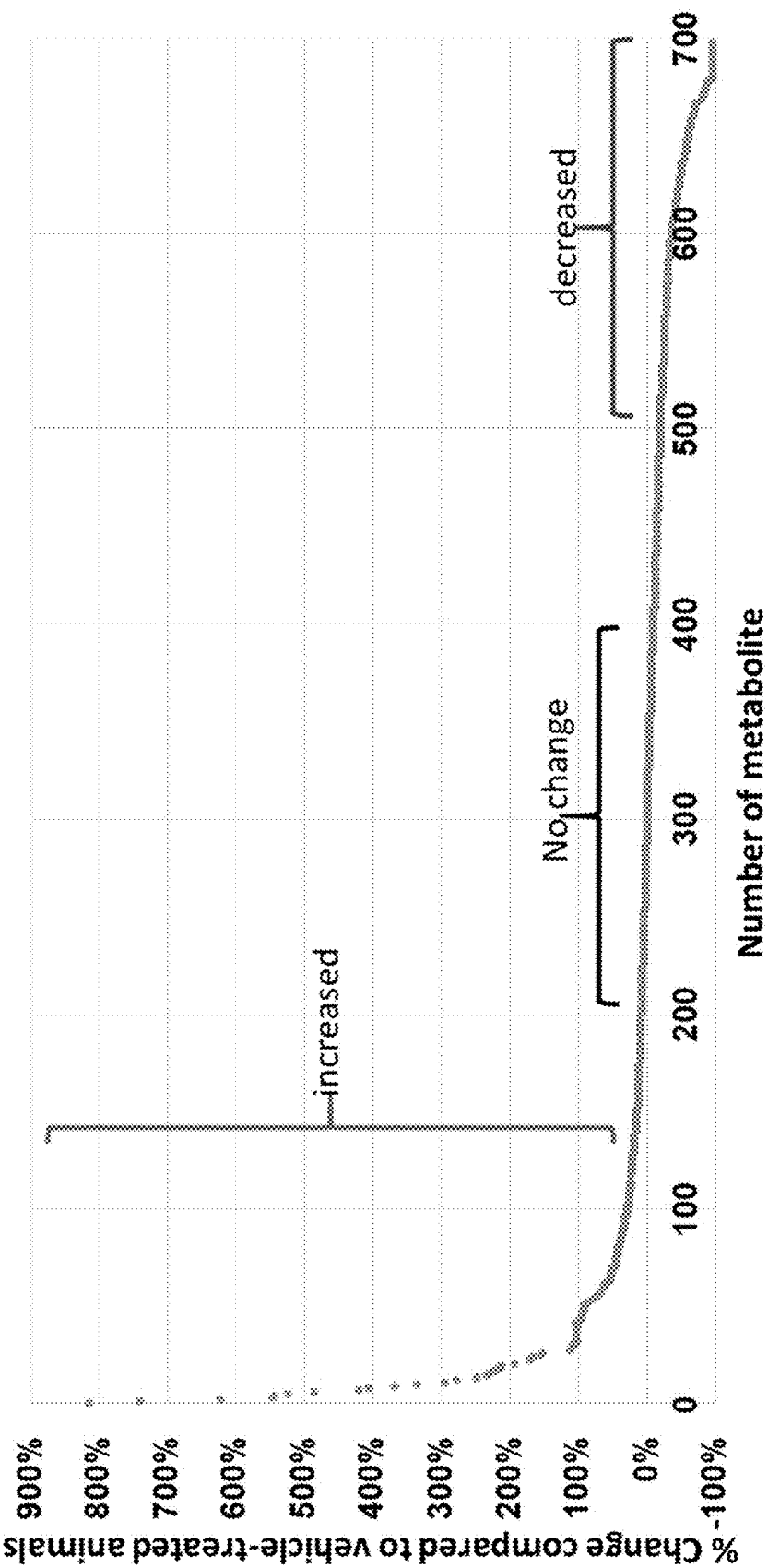

FIG. 13 shows metabolomics analysis of CT6-treated wild-type female mice. Plot shows % change of metabolite levels relative to vehicle-treated female mice for about 660 to about 700 metabolites identified in mouse plasma.

Figure 14:
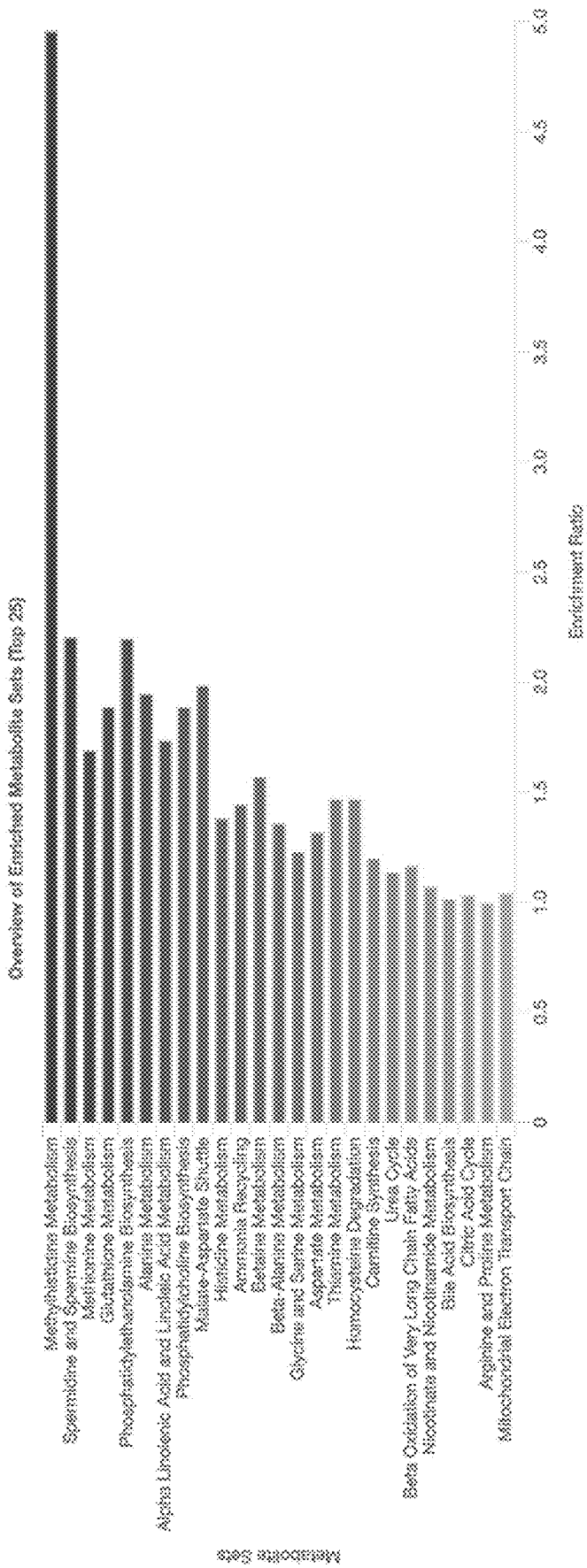

FIG. 14 shows top 25 metabolite sets in descending order of their enrichment ratios that increased in CT6-treated wild-type male mice.

Figure 15:
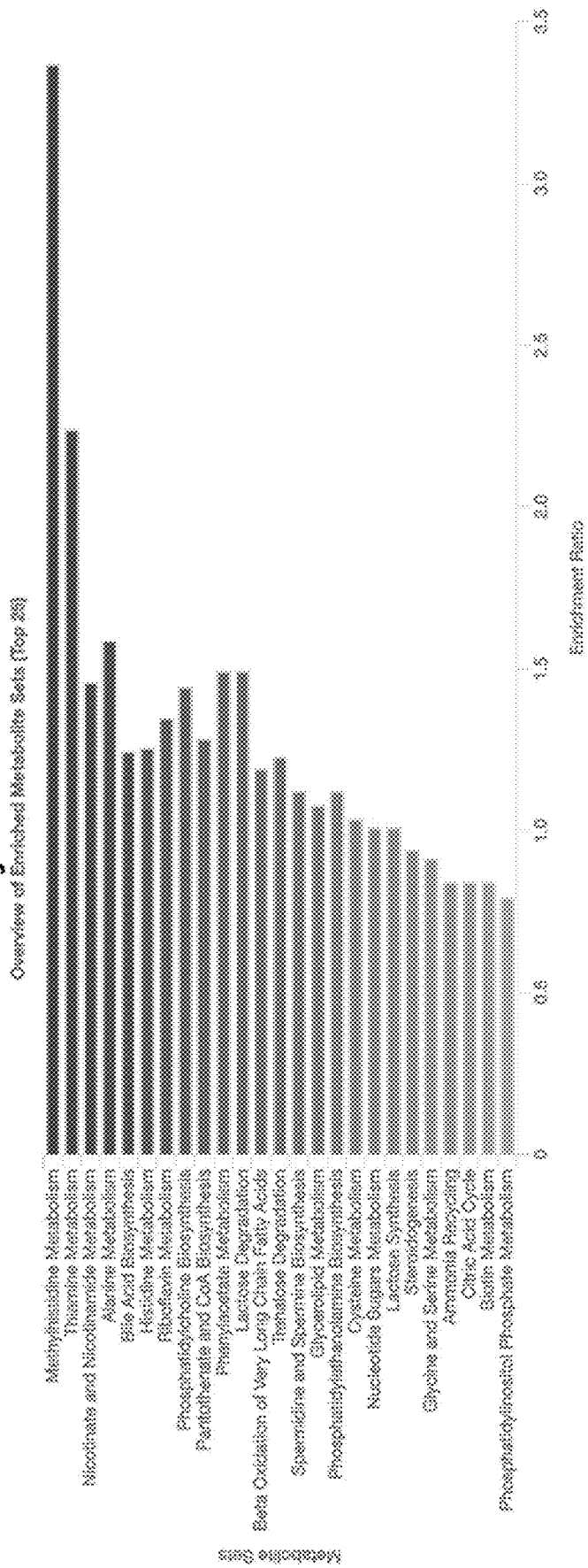

FIG. 15 shows top 25 metabolite sets in descending order of their enrichment ratios that increased in CT6-treated wild-type female mice.

Figure 16:
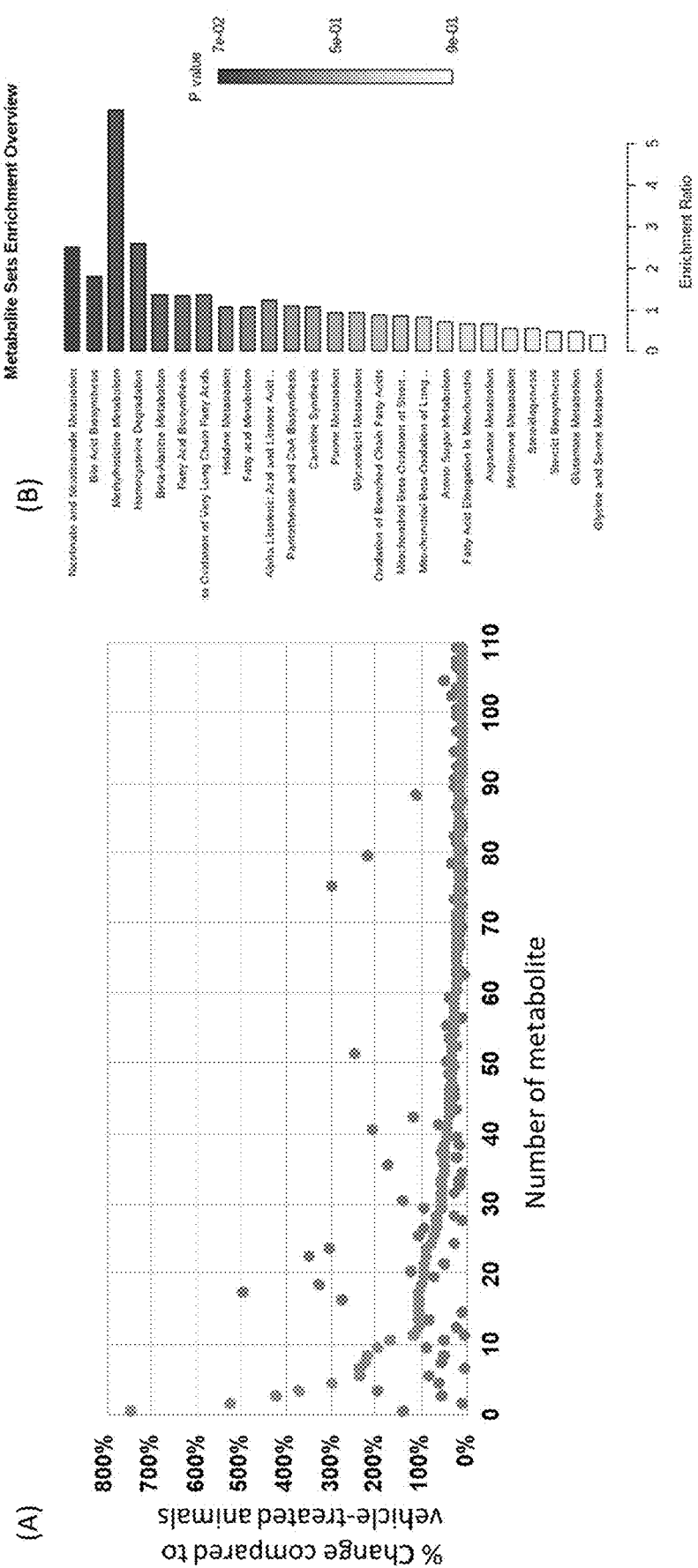

FIG. 16 shows metabolites that increased in CT6-treated wild-type male and female mice. (A) Plot shows % change of metabolite levels relative to vehicle-treated mice for metabolites that increased in CT6-treated wild-type male and female mice. (B) Plot shows top 25 metabolite sets and their enrichment ratios for metabolites that increased in CT6-treated wild-type male and female mice.

Figure 17:
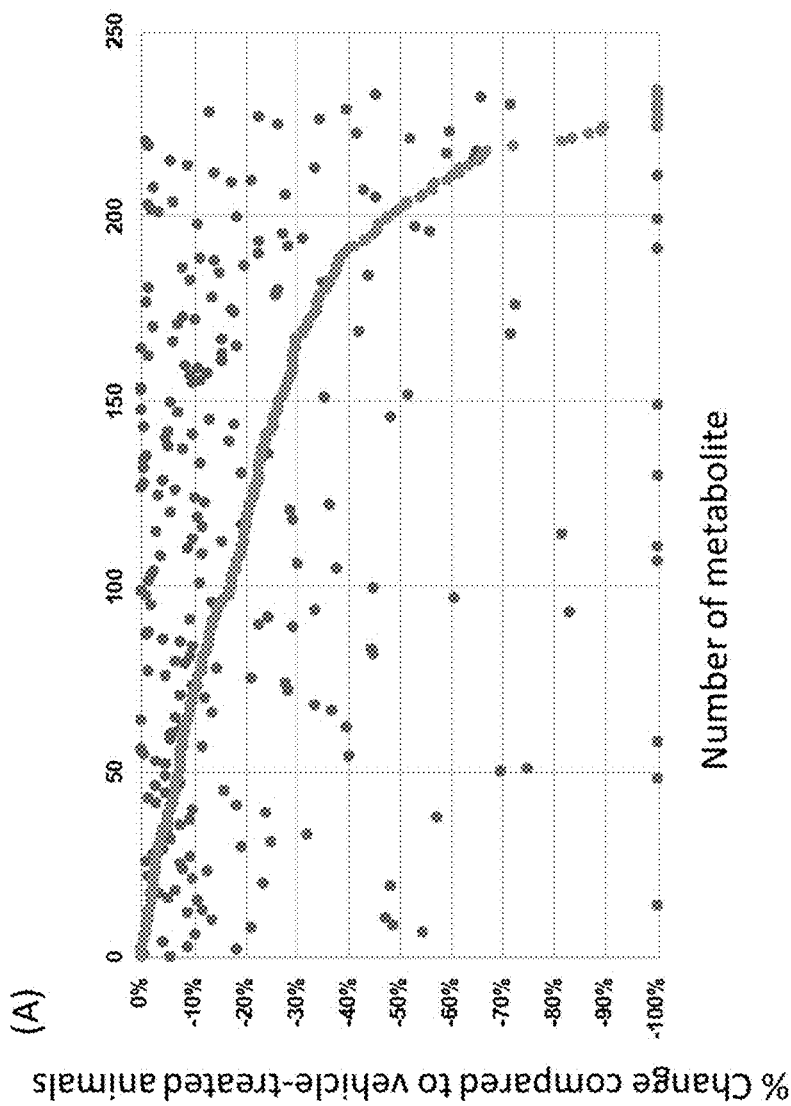
Figure 17:
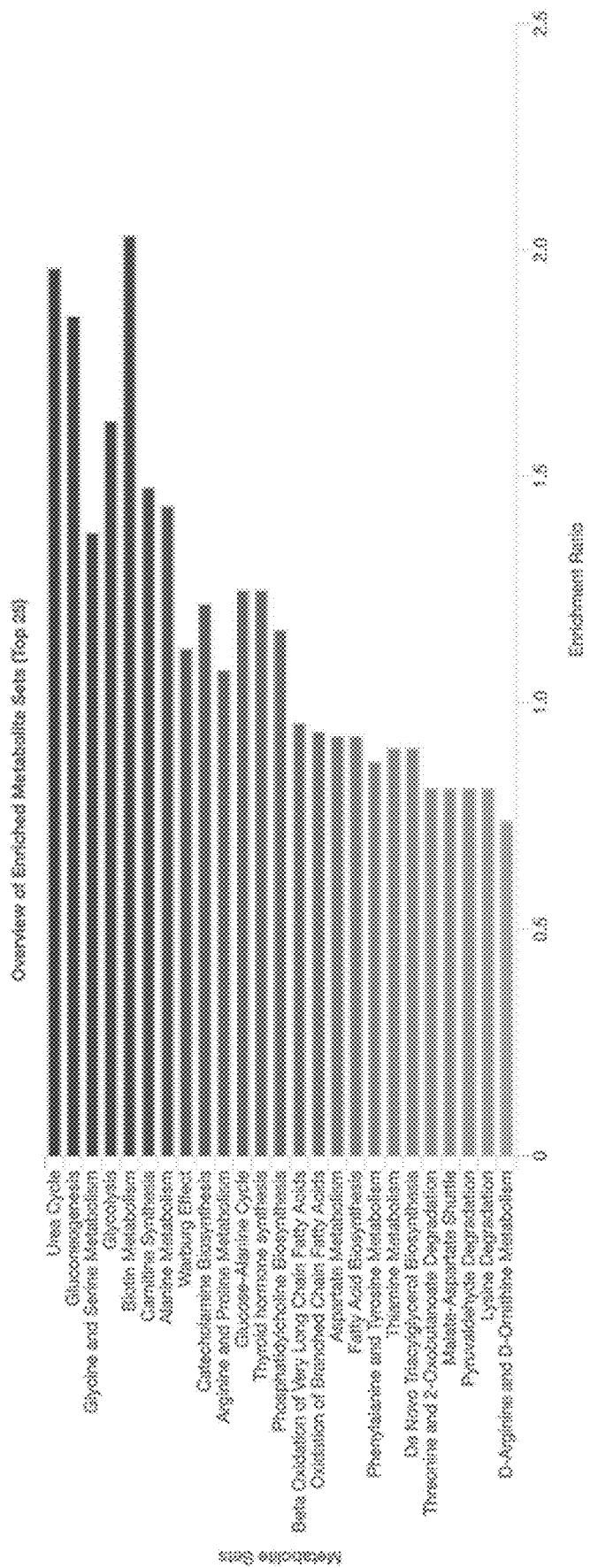

FIG. 17 shows metabolites that decreased in CT6-treated wild-type male and female mice. (A) Plot shows % change of metabolite levels relative to vehicle-treated mice for metabolites that decreased in CT6-treated wild-type male and female mice. (B) Plot shows top 25 metabolite sets and their enrichment ratios for metabolites that decreased in CT6-treated wild-type male and female mice.

Figure 18A:
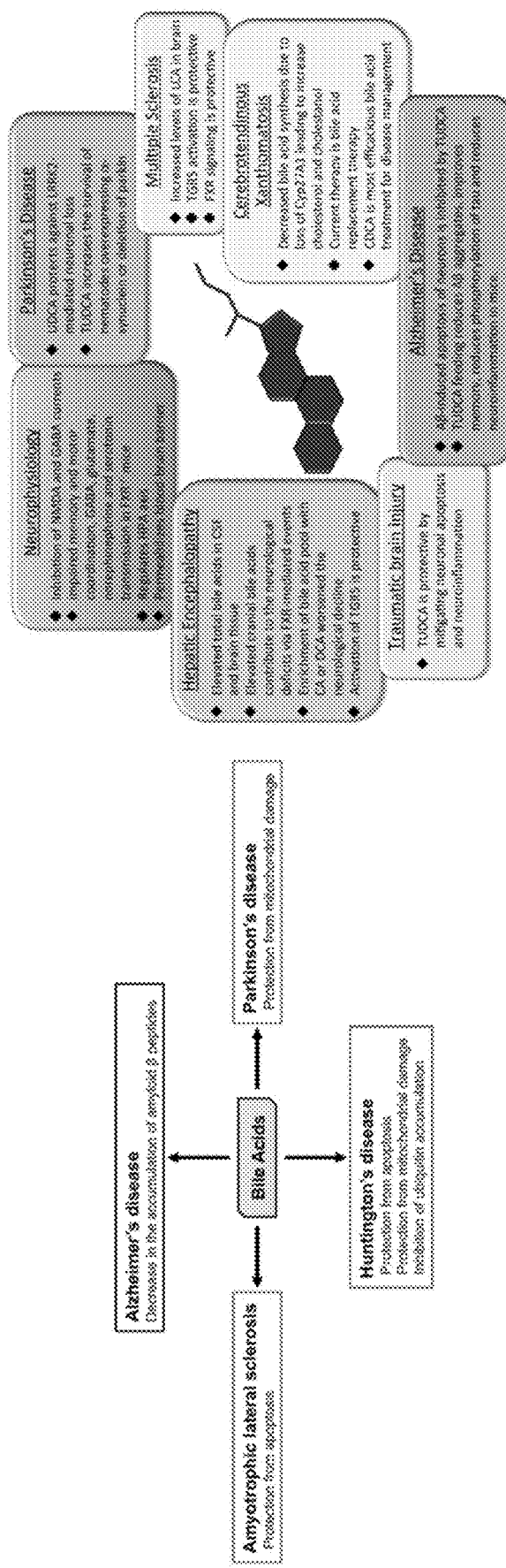

FIG. 18A shows association of bile acids in various neurodegenerative diseases including ALS, AD, PD, and HD.

FIG. 18B shows list of bile acids and their % change relative to vehicle-treated mice (i.e. bile acid level increased or decreased) in CT6-treated wild type male and female mice.

Figure 19A:
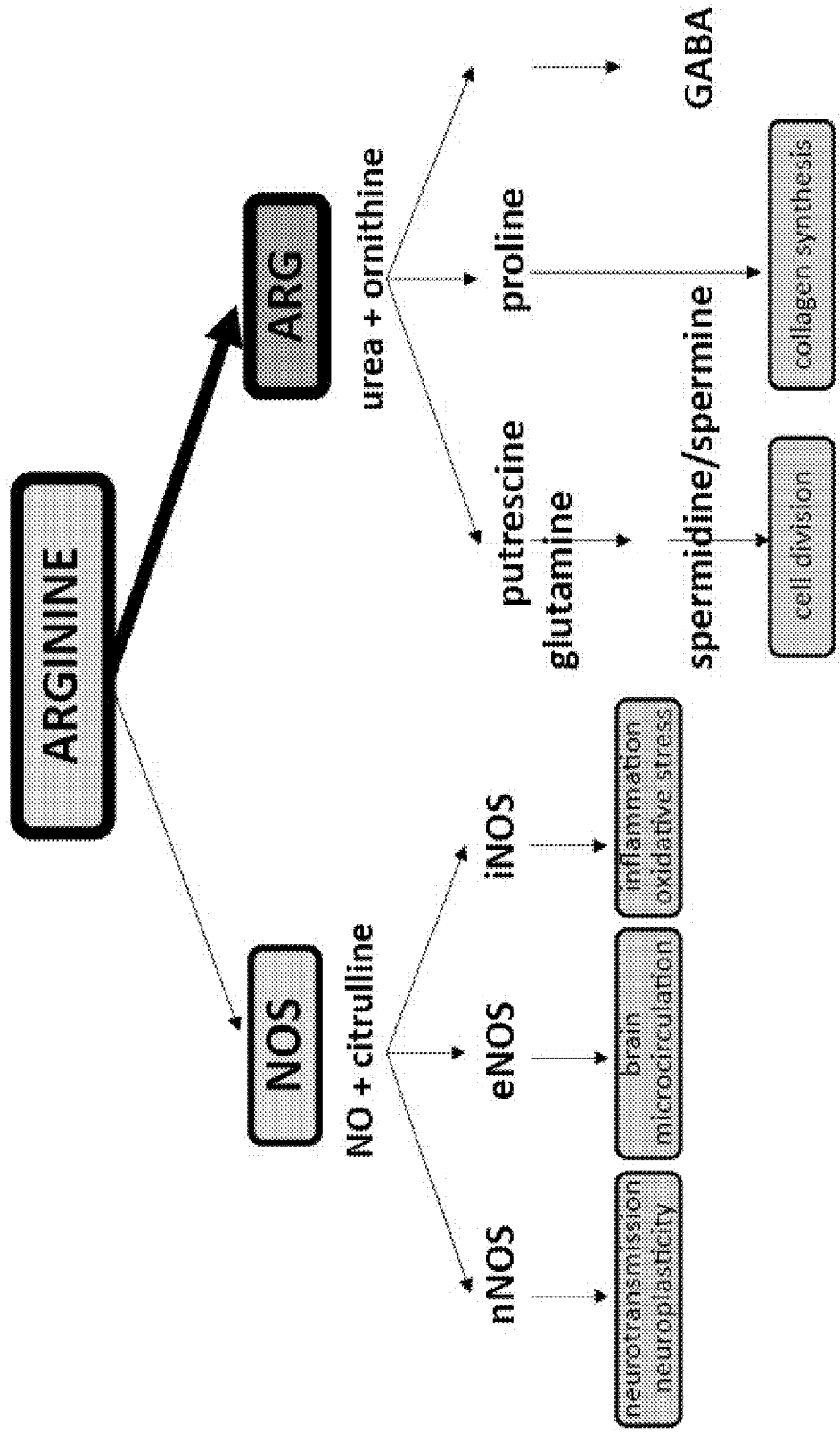

FIG. 19A shows the role of NO in various aspects of neuronal function, including but not limited to neurotransmission, neuroplasticity, brain microcirculation, inflammation, oxidative stress, etc.

Figure 19B:
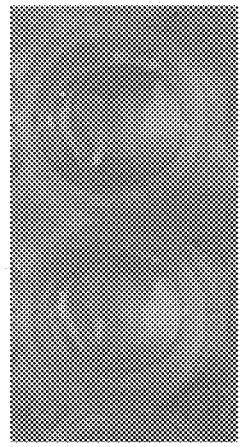
Figure 19B:
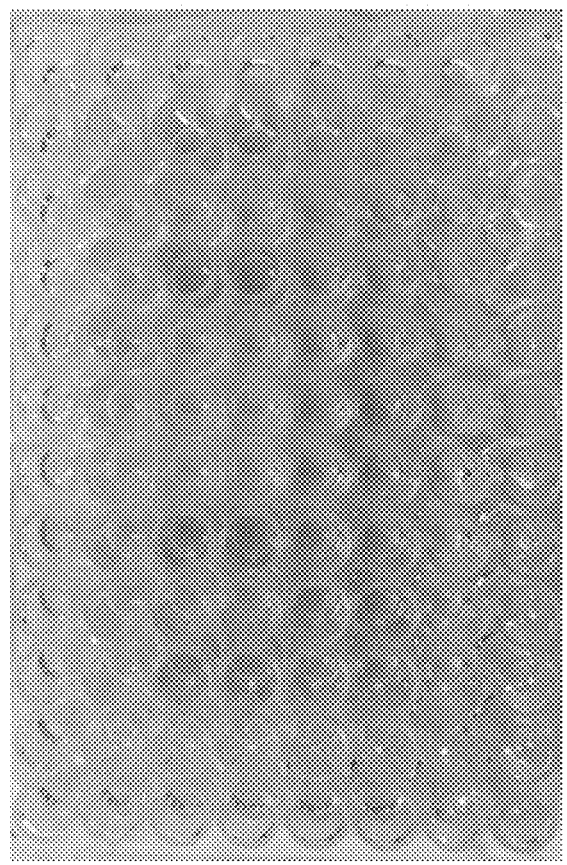

FIG. 19B shows positive and negative controls as observed in a Nitric Oxide (NO) assay, along with the assay as performed using clear 96-well plate in duplicates.

Figure 19C:
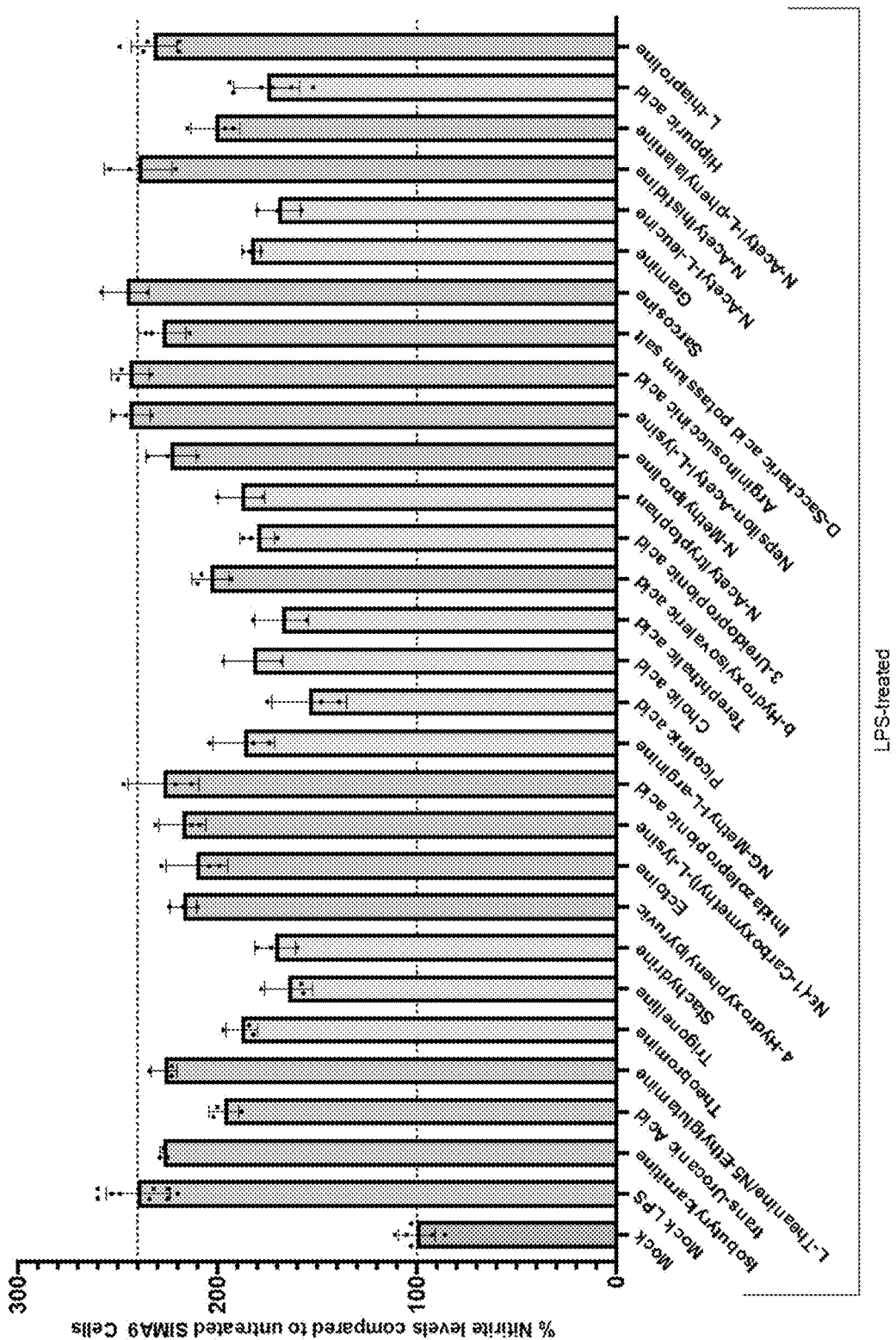

FIG. 19C shows the results of Nitric Oxide (NO) assay and plots % Nitirite levels compared to untreated SIMA9 cells for various metabolites and controls. The yellow bars represent statistically significant results.

Figure 20:
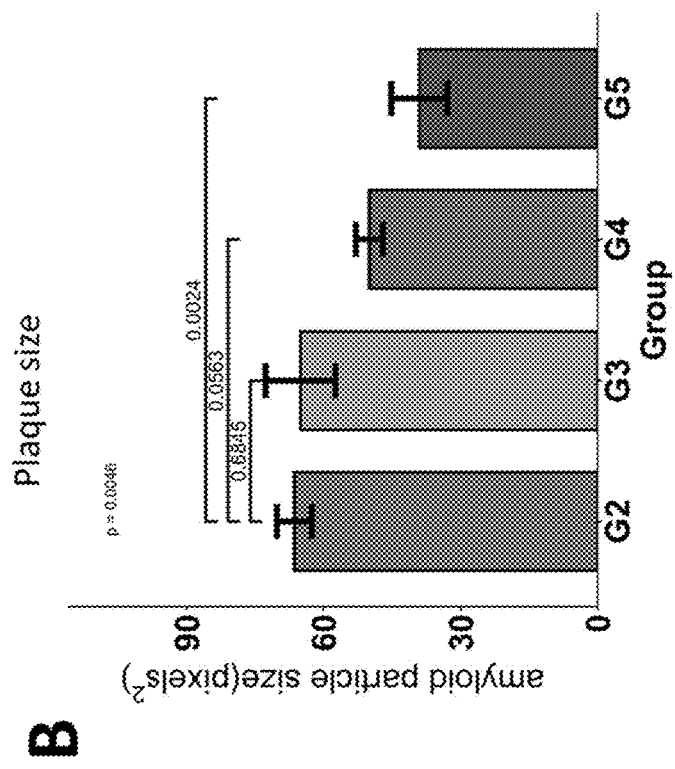
Figure 20:
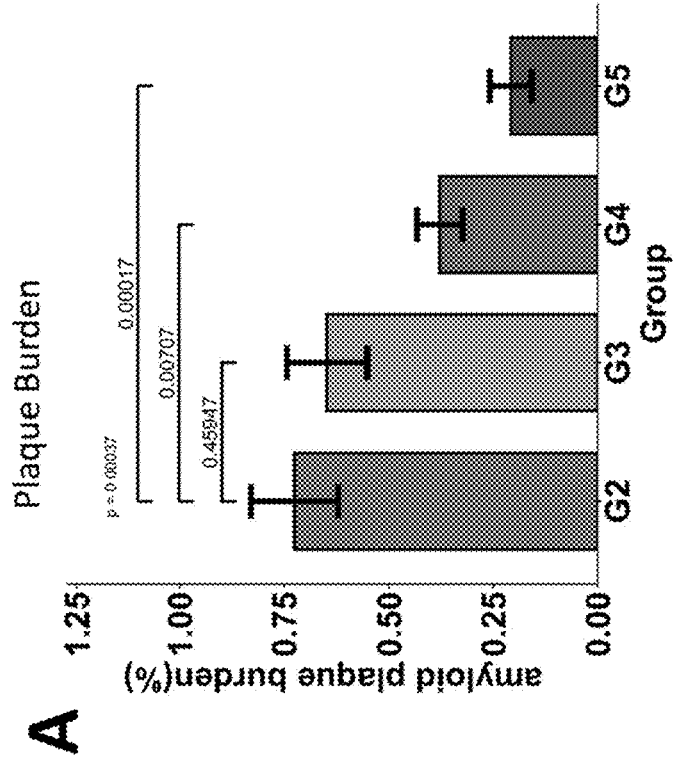

FIG. 20 shows the (A) amyloid plaque burden and (B) plaque size, in the cortex region of the brain in treated animals. The groups are G2=untreated, G3=CT10, G4=CT10m, G5=CT10x. As used herein, the terms "CT10," "CT10m," and "CT10x" refer to compositions defined in Tables 4, 5, and 6 below, respectively.

Figure 21:
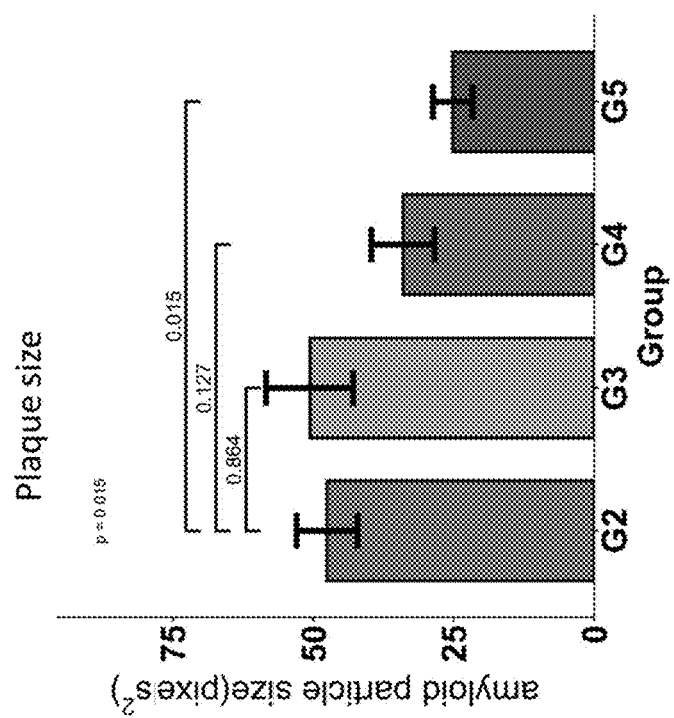
Figure 21:
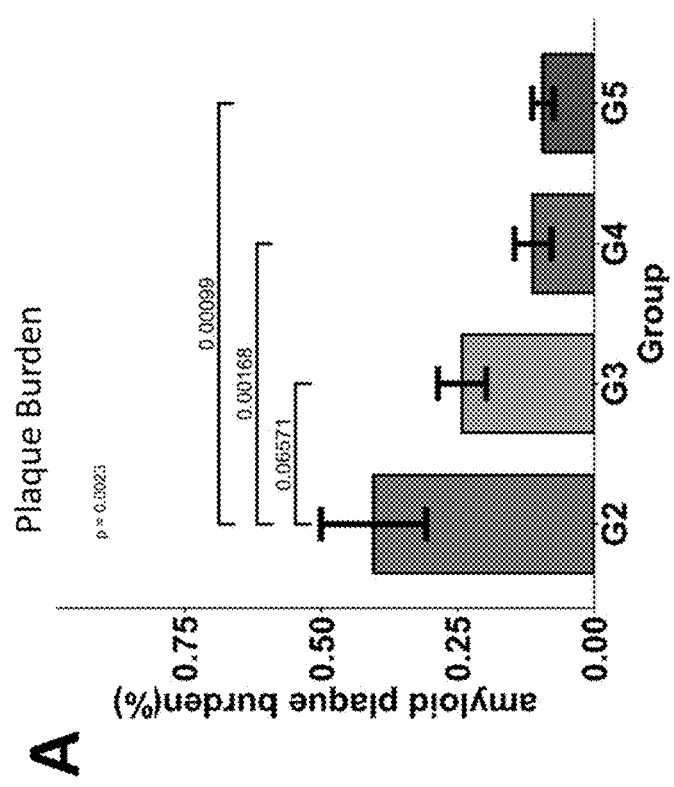

FIG. 21 shows the (A) amyloid plaque burden and (B) plaque size, in the hippocampus region of the brain in treated animals. The groups are G2=untreated, G3=CT10, G4=CT10m, G5=CT10x.

Figure 22:
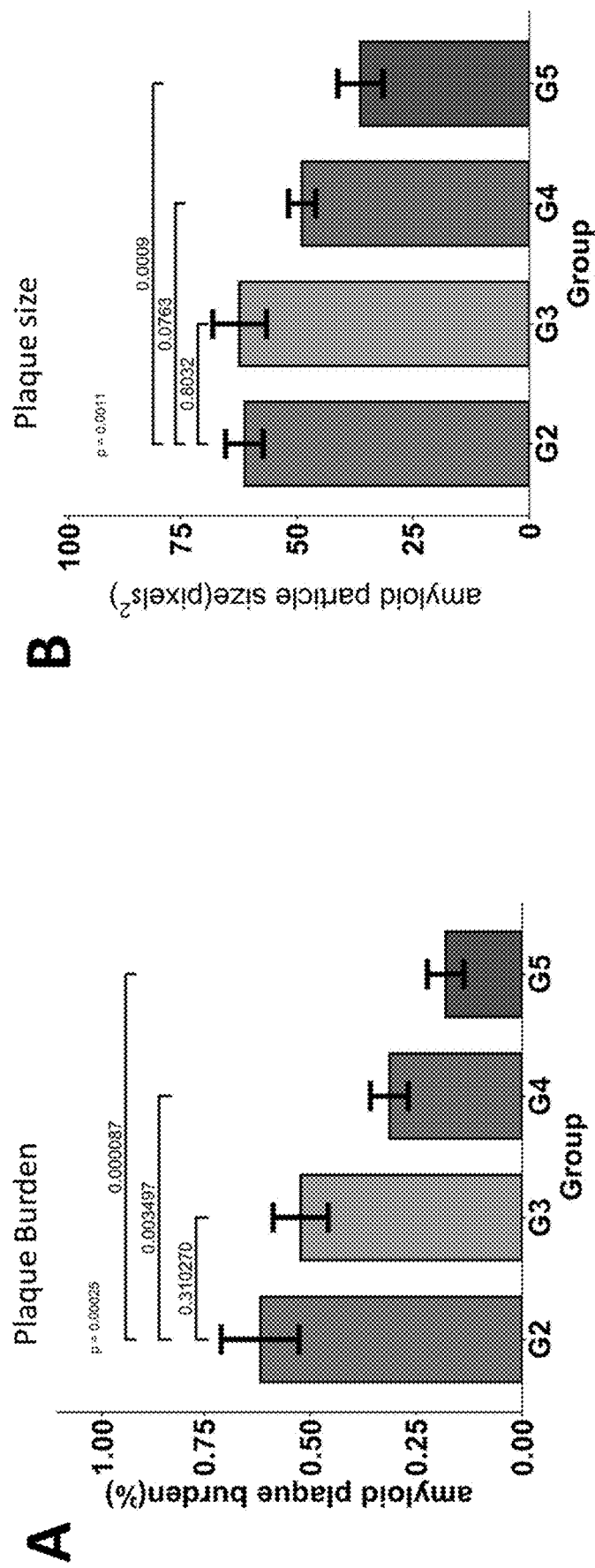

FIG. 22 shows the (A) amyloid plaque burden and (B) plaque size, in both the cortex and hippocampus region of the brain, as performed in a separate experiment, in treated animals. The groups are G2=untreated, G3=CT10, G4=CT10m, G5=CT10x.

Figure 23:
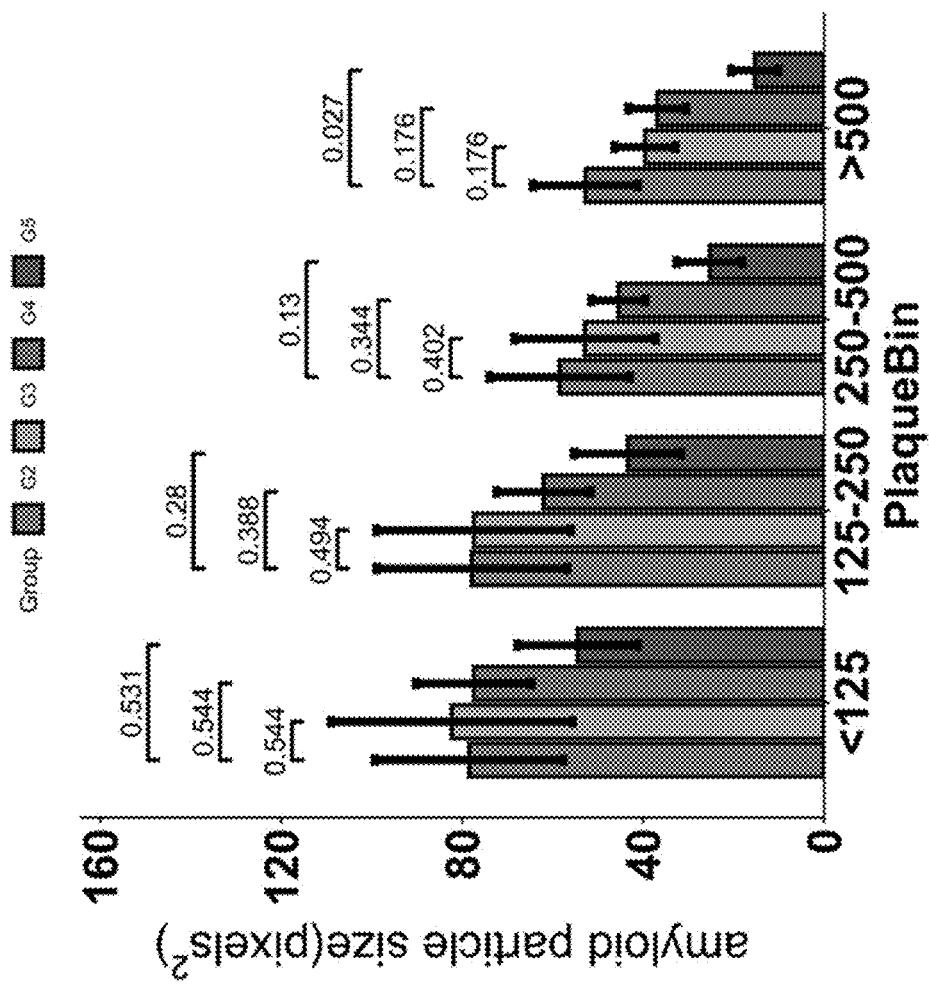

FIG. 23 shows a plot of binned amyloid particle size in the cortex region of the brain in treated animals for each of the groups G2=untreated, G3=CT10, G4=CT10m, G5=CT10x.

Figure 24:
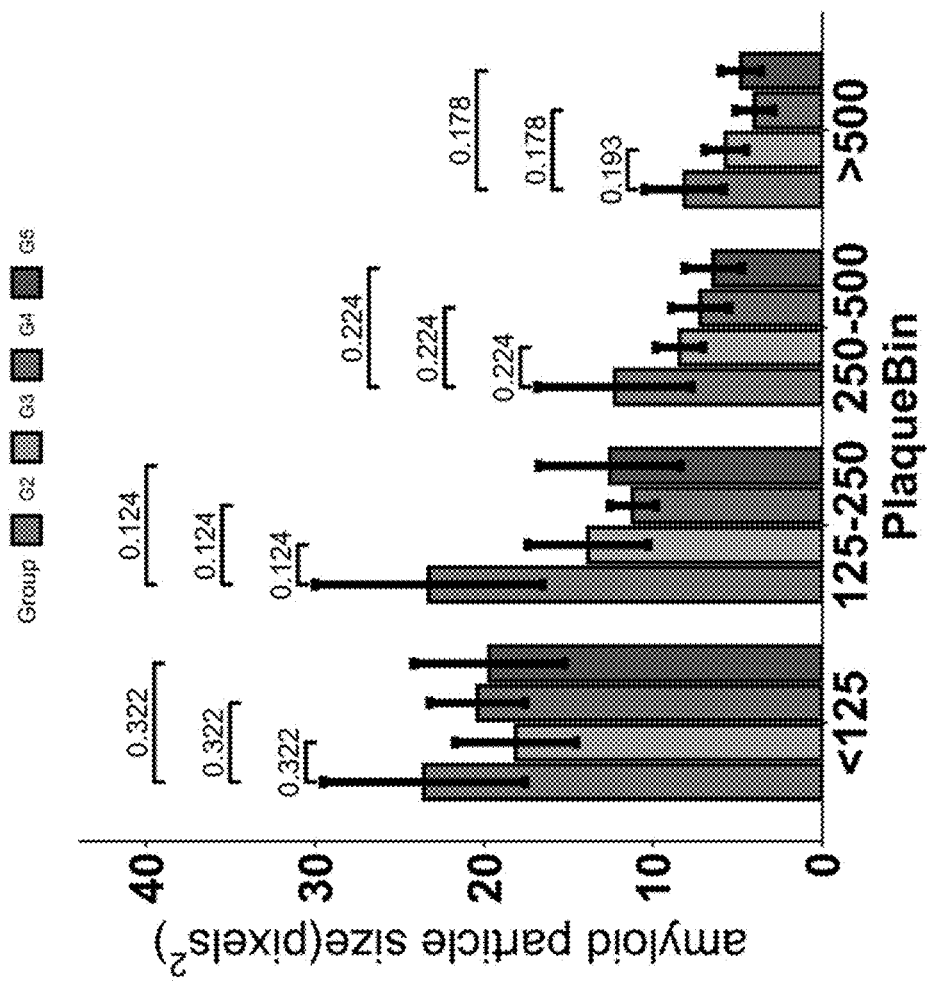

FIG. 24 shows a plot of binned amyloid particle size in the hippocampus region of the brain in treated animals for each of the groups G2=untreated, G3=CT10, G4=CT10m, G5=CT10x.

Figure 25:
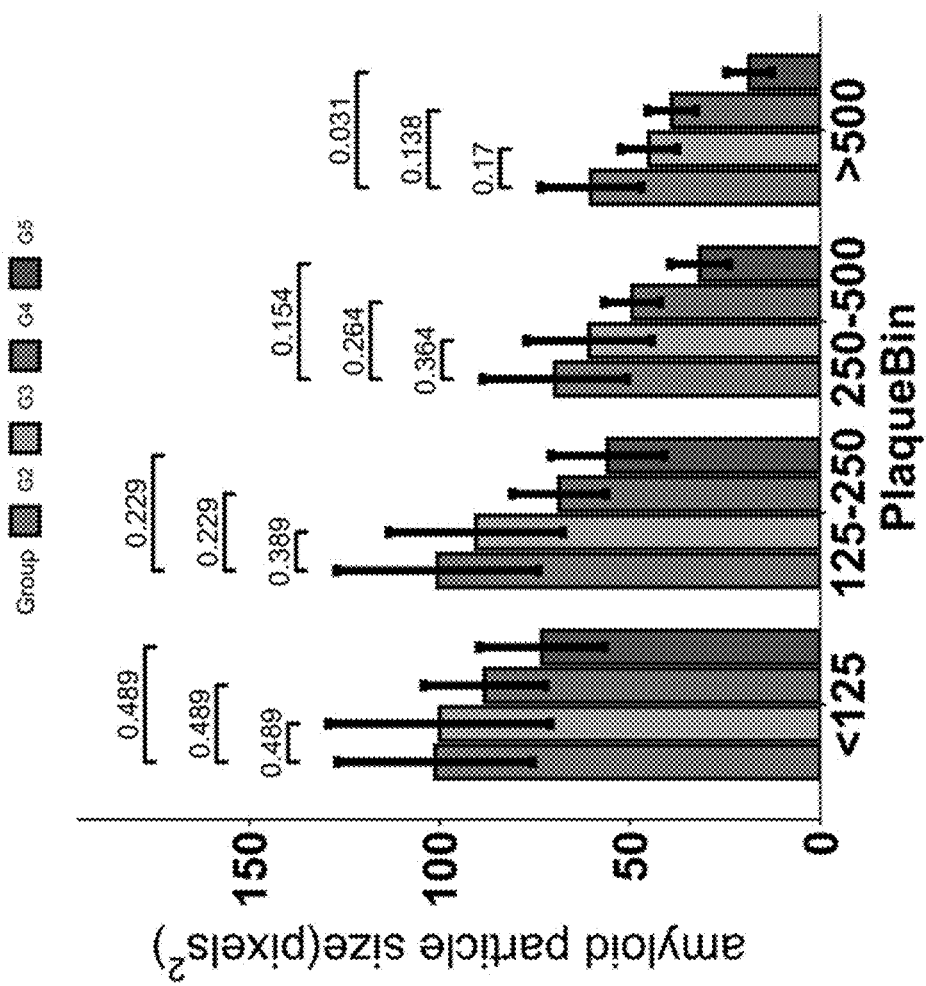

FIG. 25 shows a plot of binned amyloid particle size in the both cortex and hippocampus region of the brain in treated animals, as performed in a separate experiment, for each of the groups G2=untreated, G3=CT10, G4=CT10m, G5=CT10x.

Figure 26:
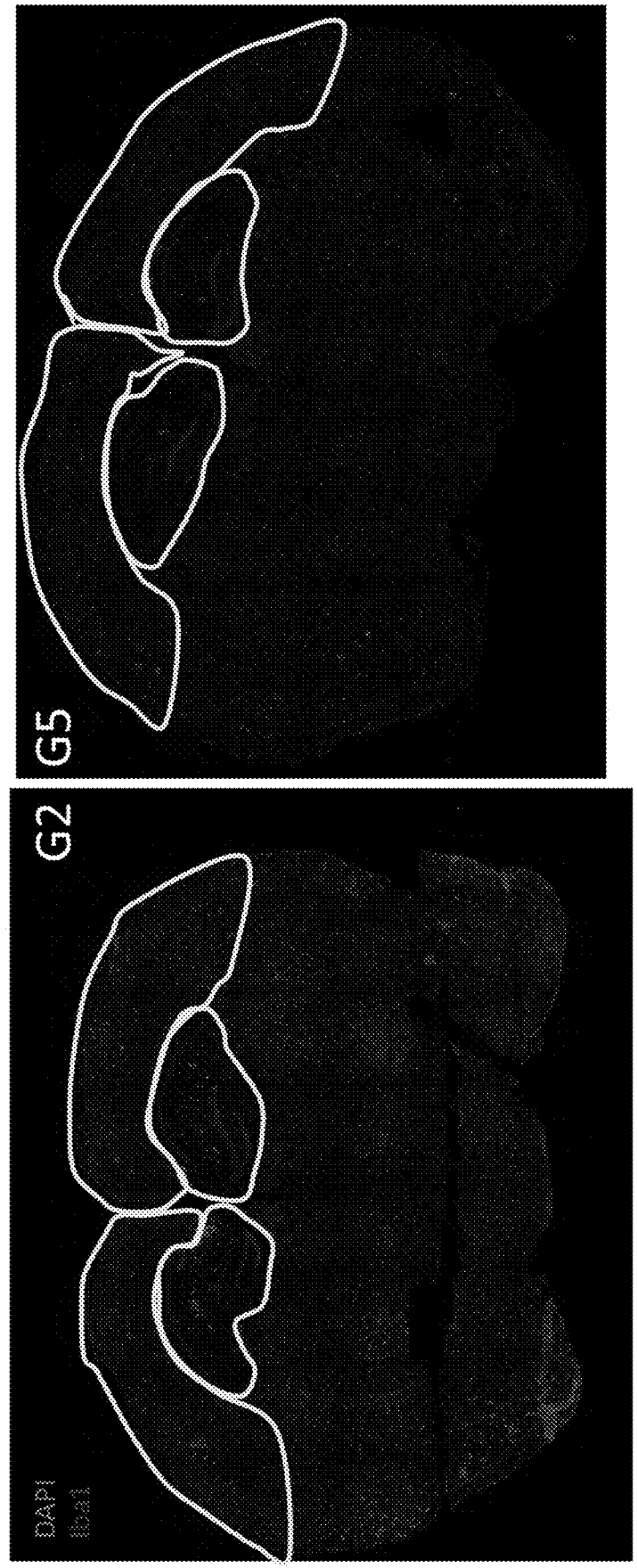

FIG. 26 shows images of the stained microglia in sections of the brain with the images adjusted to the same intensity scale.

Figure 27:
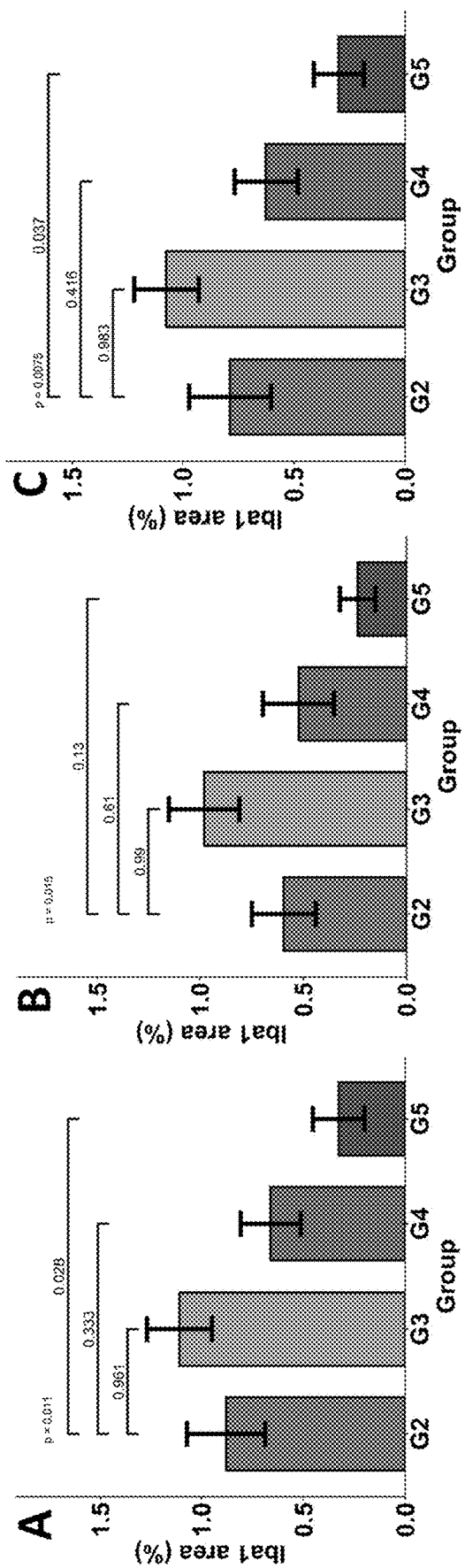

FIG. 27 shows a plot of microglia staining in the (A) cortex region of the brain, (B) hippocampus region of the brain, and (C) cortex and hippocampus region of the brain, in treated animals for each of the groups G2=untreated, G3=CT10, G4=CT10m, G5=CT10x. Microglia-stained cells and processes were measured in brain tissue sections using Iba1/AIF-1 antibody.

Figure 28:
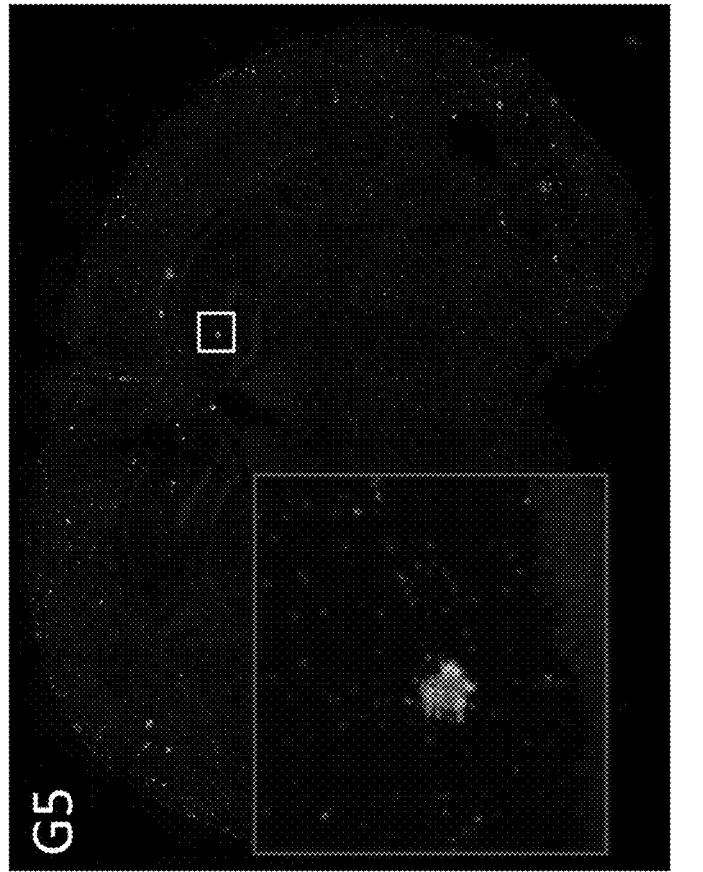
Figure 28:
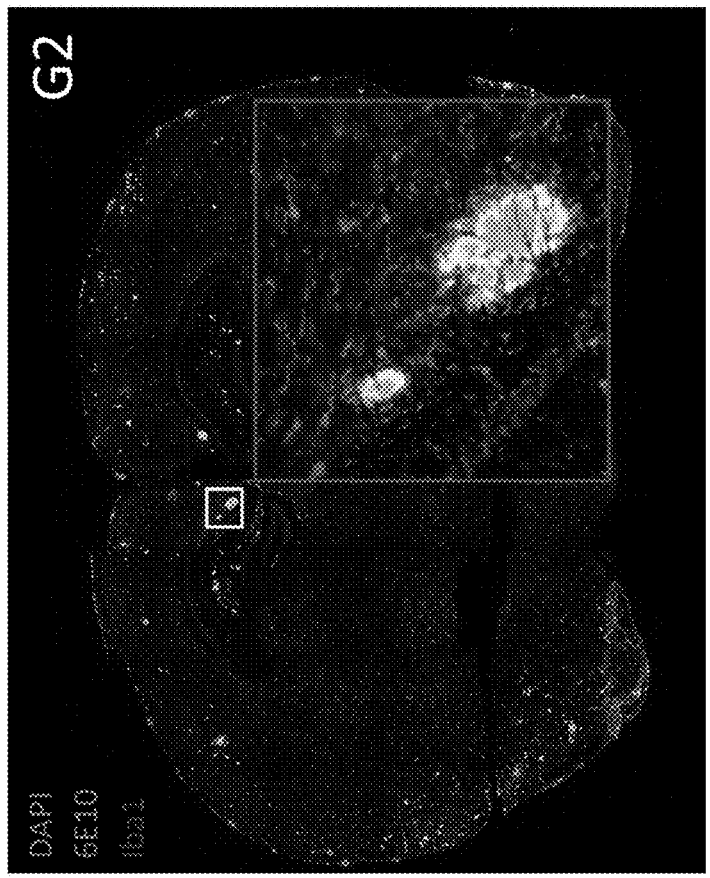

FIG. 28 images of the stained microglia in association with amyloid plaques in sections of the brain. The images were adjusted to the same intensity scale.

Figure 29:
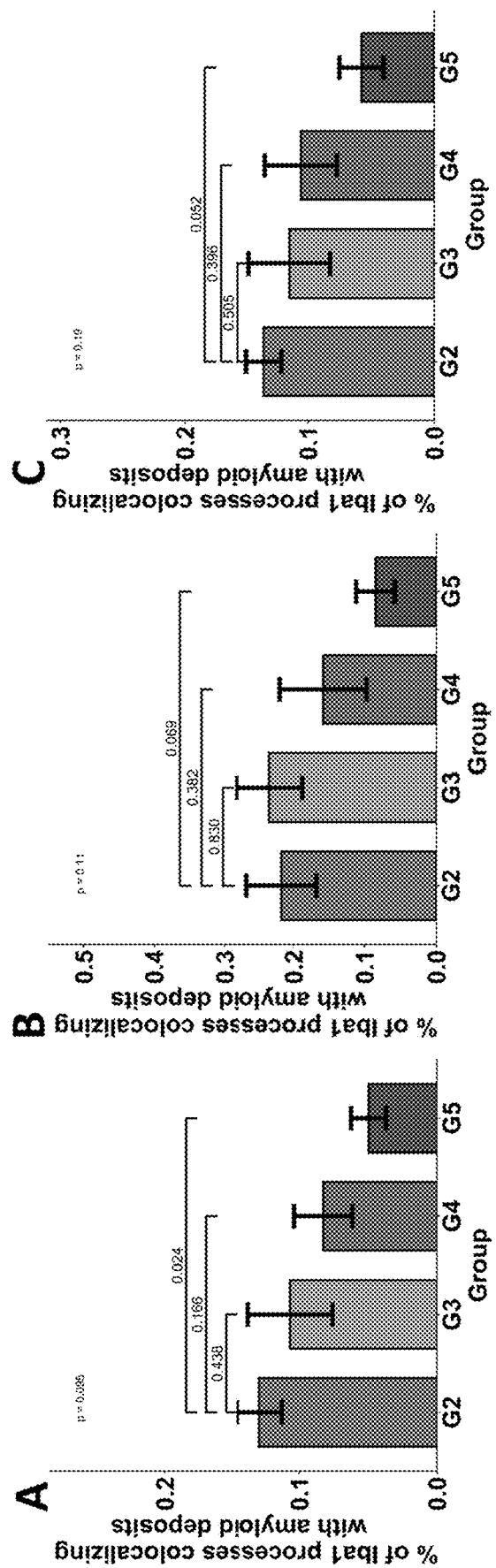

FIG. 29 shows a plot microglia association with amyloid plaques in the (A) cortex region of the brain, (B) hippocampus region of the brain, and (C) cortex and hippocampus region of the brain, in treated animals for each of the groups G2=untreated, G3=CT10, G4=CT10m, G5=CT10x.

DETAILED DESCRIPTION OF CERTAIN EMBODIMENTS

Neurodegenerative Diseases, Disorders, and Conditions

Neurodegenerative diseases, disorders, and conditions are an umbrella term for a range of diseases, disorders, and conditions which primarily affect the neurons in the human brain. These are incurable and debilitating conditions that result in progressive degeneration and/or death of nerve cells. This causes problems with movement (called ataxias), or mental functioning (called dementias). Some examples of neurodegenerative diseases, disorders, and conditions include ALS, PD, AD, and HD.

Amyotrophic Lateral Sclerosis (ALS):

ALS, also known as Lou Gehrig's disease, is the most fatal progressive neurodegenerative disease, characterized by the predominant loss of motor neurons (MNs) in primary motor cortex, the brainstem, and the spinal cord. The loss of motor neurons devastates basic, fundamental movements, such as breathing, and typically causes death to patients within 2-5 years after diagnosis. Progressive deterioration of motor function in patients severely disrupts their breathing ability, requiring some form of breathing aid for survival of the patients. Other symptoms also include muscle weakness in hands, arms, legs or the muscles of swallowing. Some patients (e.g., FTD-ALS) may also develop frontotemporal dementia.

According to the ALS Association, approximately 5,600 people in the United States of America are diagnosed with ALS each year. The incidence of ALS is two per 100,000 people, and it is estimated that as many as 30,000 Americans may have the disease at any given time.

Two forms of ALS have been described: one is sporadic ALS (SALS), which is the most common form of ALS in the United States of America and accounts for 90 to 95% of all cases diagnosed; the other is familial ALS (FALS), which occurs in a family lineage mainly with a dominant inheritance and only accounts for about 5 to 10% of all cases in the United States of America. SALS and FALS are clinically indistinguishable.

Pathological studies found that disturbance of some cellular processes occur after disease onset, including increased ER stress, generation of free radicals (i.e., reactive oxygen species (ROS)), mitochondrial dysfunction, protein aggregation, apoptosis, inflammation and glutamate excitotoxicity, specifically in the motor neurons (MNs).

The causes of ALS are complicated and heterogeneous. In general, ALS is considered to be a complex genetic disorder in which multiple genes in combination with environmental exposures combine to render a person susceptible. More than a dozen genes associated with ALS have been discovered, including, SOD-1 ($Cu^{2+}/Zn^{2+}$ superoxide dismutase), TDP-43 (TARDBP, TAR DNA binding protein 43), FUS (Fused in Sarcoma/Translocated in Sarcoma), ANG (Angiogenin), ATXN2 (Ataxin-2), valosin containing protein (VCP), OPTN (Optineurin) and an expansion of the non-coding GGGGCC hexanucleotide repeat in the chromosome 9, open reading frame 72 (C9ORF72). However, the exact mechanisms of motor neuron degeneration are still elusive.

Currently, there is no curative treatment for ALS. The only FDA approved drug is Riluzole, which antagonizes the glutamate response to reduce the pathological development of ALS. However, only about a three-month life span expansion for ALS patients in the early stages has been reported, and no therapeutic benefit for ALS patients in the late stages has been observed, indicating a lack of therapeutic options for the patients (Bensimon G et al., J Neurol. 2002, 249, 609-615). Therefore, a new treatment strategy that can effectively prevent the disease progression is required.

Parkinson's Disease (PD):

PD is a neurodegenerative movement disorder characterized by resting tremor, rigidity, bradykinesia, and postural instability. PD symptoms are classically attributed to dopamine depletion and the degeneration of dopaminergic neurons in the substantia nigra pars *compacta* (SNc). However, additional neuronal circuits are affected, and non-motor symptoms are often present, suggesting a systemic pathology. There is compelling evidence that mitochondrial dysfunction is a primary event in the disease process. It has been reported that PD-related mutations and mitochondrial dynamics have a reciprocal relationship. PD-related mutations can perturb mitochondrial dynamics, and the consequences of these mutations can be modulated by mitochondrial dynamics.

In one embodiment, effective treatment of PD is determined by a reduction in the dose of pharmacological treatments, such as L-DOPA, required to maintain adequate control of symptoms of PD. In another embodiment, efficacy of treatment is monitored using the Unified Parkinson's Disease Rating Scale (UPDRS) as known in the art.

PD is the most common motor-related disorder in middle or late life disease, affecting ~6.2 million people worldwide (Global Burden of Disease Study 2015. Lancet 388, 1545-1602 (2016)). PD is characterized by accumulation of α-synuclein inclusions in the neurons and degeneration and/or loss of dopaminergic neurons. The cardinal clinical symptoms of PD includes slow movement, resting tremor, rigidity, and postural instability (Pires, A O, et al., Therapeutics. Prog. Neurobiol. (2017); doi: 10.1016/j.pneurobio.2017.04.006). While a majority of PD cases are of unknown origin and sporadic, mutations in some genes have been associated with rare, familial forms of the disease. Several lines of evidence implicate defects in mitochondrial respiration in the etiology and pathogenesis of PD. First, MPTP, an inhibitor of complex I of the electron transport chain, can induce PD (Nicklas, W J, et al., Life Sci. 36, 2503-2508 (1985); Ramsay, R R, et al., Biochem Biophys Res Commun 135, 269-275 (1986)). Inhibition of complex I results in decreased mitochondrial ATP production, increased production of mitochondria-derived Reactive Oxygen Species (ROS), and activation of mitochondria-dependent apoptotic pathways. Second, post mortem studies of PD patients found elevated levels of oxidative stress markers/products (Yoritaka, A. et al. Proceedings of the National Academy of Sciences 93, 2696-2701 (1996); Floor, E, & Wetzel, MG, J Neurochem 70, 268-275 (2002); Zhang, J. et al., Am. J Pathol. 154, 1423-1429 (1999)) in the dopaminergic neurons. Third, a reduction of mitochondrial complex I activity by 30% was observed in brain as well as peripheral tissues of PD patients (Schapira, A H V, et al., The Lancet 333, 1269 (1989); Parker, W D, et al., Ann. Neural. 26, 719-723 (1989)). Fourth, neurotoxins such as rotenone, paraquat, and 6-hydroxydopamine (6-OHDA) induce mitochondrial dysfunction resulting in PD-associated phenotypes in animal models (Tieu, K, Cold Spring Harb Perspect Med 1, a009316-a009316 (2011)). Finally, PD-associated genes such as a-synuclein, LRRK2 (leucine-rich repeat kinase 2), parkin, PINK1, and DJ-1 affect mitochondrial dynamics, trafficking, autophagy, and quality control (Moore, D J, et al., Annu. Rev. Neurosci. 28, 57-87 (2005); Robinson, PA, Expert Review of Proteomics, 7(4), 565-578).

All cells require mitochondria for their energy demands including neurons, which are critically dependent on proper mitochondrial function. Neurons have high metabolic activity and they depend heavily on mitochondria for their bioenergetic demand. Several factors make the neurons in general, and dopaminergic neurons in particular, susceptible to degeneration; these include ROS (which result from dopamine metabolism and mitochondrial dysfunction), low endogenous antioxidant levels, and high levels of iron and calcium (which are known to promote ROS formation) (Dias, V, et al, Journal of Parkinson's Disease, 3(4), 461-491 (2013)). Further, neuronal tissues contain high levels of polyunsaturated fatty acids, which are prone to lipid peroxidation and the generation of toxic products (Liu, X, et al, Journal of Biological Chemistry, 283(50), 34887-34895 (2008)). Regardless of whether a primary or secondary cause, mitochondrial dysfunction holds promise as a potential therapy target. Aging is the greatest risk factor for PD (Collier, T J, et al, Nature Reviews. Neuroscience, 12(6), 359-366 (2011)), thus with increasing average life expectancy worldwide (GBD 2013, Lancet 385, 117 (2015)), the number of people affected by PD will rise considerably in the near future. Thus, there is a significant clinical unmet need for new therapeutic approaches that not only can be used for slowing down PD, but also as preventive measures for the aging population.

While most of the earlier studies on PD focus entirely on the brain pathologies, the gastrointestinal (GI) system is now recognized as an important source for PD pathogenesis (Mukherjee, A, et al, Journal of Gastroenterology, 22(25), 5742-5752 (2016); Pellegrini, C, et al, Neurogastroenterology & Motility, 28(12), 1781-1791 (2016); Kuo, Y M, et al, Human Molecular Genetics, 19, 1, 1633-1650 (2010)). GI symptoms, such as constipation, affects ~80% of PD-patients and idiopathic constipation is an important risk factor for PD (Noyce, A J, et al, Anals of Neurology, 72, 893-901 (2012)). In PD, constipation is associated with alpha-synuclein accumulation in the enteric nervous system (Cersosimo, M G, and Benarroch, E E, Neurobiology of Disease, 46, 559-564 (2012)), gut inflammation, and increased gut permeability (Devos, D, et al, Neurobiology of Disease, 42-48 (2013)). Further, the intestinal mucosal inflammation is thought to lead to synuclein accumulation in the enteric nerves, which can then spread in a prion-like fashion to the central nervous system via autonomic connections (Braak, H, et al, Journal of Neurotransmission, 110, 517-536 (2003); Hawkes, C H, et al, Neuropathology and Applied Neurobiology, 33, 599-614 (2007); Hawkes, C H, et al, International Symposium of Olfaction and Taste, 1170, 615-622 (2009)). Many of the GI tract changes are observed even before the onset of neuronal symptoms (Verbaan, D, et al, Neurology, 69, 333-341 (2007)); thus, PD pathogenesis might act primarily via the GI tract (Shannon, K M, et al, Mov. Disord. 27, 716-719 (2012); Kieburtz, K, and Wunderle, KB, Mov. Disord., 28, 8-13 (2013)).

Alzheimer's Disease (AD):

AD is a fatal neurodegenerative disease characterized by progressive decline in memory and cognitive functions. Early-onset familial AD associated with the mutations in APP or γ-secretase gene accounts for less than 5% of the all cases while 95% of the sporadic or late-onset AD has unknown etiology (Masters, C. L. et al., Nat Rev Dis Primers C 15056 (2015)). The pathological hallmarks of AD are accumulation of extracellular senile plaques and intracellular neurofibrillary tangles (NFTs) in the AD patient's brain. The senile plaques consist of β-amyloid peptide (Aβ) as the primary component while NFTs consist of abnormal fibrillar forms of microtubule-associated protein tau as the primary component (Nelson, P. T. et al., J. Neuropathol. Exp. Neurol. 71, 362-381 (2012)). Aβ accumulation and NFTs are thought to indicate neuronal dysfunction and impending neuronal demise (Nelson, P. T. et al., J. Neuropathol. Exp. Neurol. 71, 362-381 (2012)).

Mitochondrial dysfunction and defects in energy metabolism have been consistently observed in human AD patients (Halliwell, B, J Neurochem, 97, 1634-1658 (2006); Cheignon, C. et al., Redox Biol 14, 450-464 (2018)). Aβ and tau pathologies are strongly associated with mitochondrial dysfunction in AD. Aβ and tau directly affect mitochondrial function causing impairment of ATP production, increased reactive oxygen species (ROS) production, decreased oxygen consumption, and decreased mitochondrial complex I and IV function (Muller, W E, et al., Mol. Neurobiol. 41, 159-171 (2010)). Mitochondrial dysfunction is found to be an early event in AD. In the case of sporadic AD, progressive increase in oxidative stress with advancing age is shown to cause Aβ deposition and NFTs formation (Moreira, P I, et al., Biochim. Biophys. Acta 1802, 2-10 (2010)). This could lead to a continuous cycle of events where the Aβ and tau exacerbates mitochondrial dysfunction leading to rapidly progressive AD symptoms.

About one third of the drugs used in the clinic today were initially isolated from plants or microbes. Though chemical synthesis of compounds has taken over the pharmaceutical industry as the source for identifying novel therapeutics, bioprospecting natural sources like plants and microbes continues to play important role as therapeutic agents. Recent studies have started to explore the human microbiome as a source of drugs (Donia, M S, and Fischbach, M A, Science 349, 1254766-1254766 (2015)). The human body is home to a society of benign, symbiotic, commensal and pathogenic microbes collectively known as the microbiome. These microbes can modulate host brain function and behavior via the gut-brain axis and production of several metabolites such as GABA, glutamate and serotonin.

Dysfunction in the microbiome-derived metabolite signaling can contribute to neurological disorders including AD (Sharon, G, et al, Cell 167, 915-932 (2016); Hill, J M, Front Neurol 5, 43 (2014)). In summary, the microbiome presents an untapped rich resource for mining novel neuroprotective compounds or live biotherapeutics that will be relevant for AD.

The present disclosure provides compositions (e.g. microbiome compositions) and methods that inhibit one or more of the events or processes that take place in neurodegenerative diseases, disorders, or conditions. The present disclosure is based in part on the discovery that one or more microbial strains or compositions comprising one or more microbial strains are particularly suitable as therapeutic agents for neurodegenerative diseases, disorders, or conditions.

Huntington's Disease (HD):

HD is a monogenic fatal neurodegenerative disease characterized by progressive chorea, neuropsychiatric and cognitive dysfunction. HD is known to be caused by an autosomal dominant triplet (CAG) repeat expansion which encodes poly-glutamine in the N-terminus of the huntingtin (HTT) protein. This repeat expansion results in a toxic gain of function of HTT and ultimately leads to striatal neurodegeneration which progresses to widespread brain atrophy. Symptoms typically appear between the ages of 35-44 and life expectancy subsequent to onset is 10-25 years. Interestingly, the length of the HTT expansion correlates with both age of onset and rate of disease progression, with longer expansions linked to greater severity of disease. In a small percentage of the HD population (~6%), disease onset occurs from 2-20 years of age with appearance of an akinetic-rigid syndrome. These cases tend to progress faster than those of the later onset variety and have been classified as juvenile or Westphal variant HD. It is estimated that approximately 35,000-70,000 patients are currently suffering from HD in the US and Europe. Currently, only symptomatic relief and supportive therapies are available for treatment of HD, with a cure yet to be identified. Ultimately, individuals with HD succumb to other diseases (e.g., pneumonia, heart failure, etc.), choking, suffocation or other complications such as physical injury from falls.

The mechanisms by which CAG-expanded HTT results in neurotoxicity are not well understood. Huntingtin protein is expressed in all cells, though its concentration is highest in the brain. The normal function of HTT is unknown, but in the brains of HD patients, HTT aggregates into abnormal nuclear inclusions. It is now believed that it is this process of misfolding and aggregating along with the associated protein intermediates (i.e. the soluble species and toxic N-terminal fragments) that result in neurotoxicity.

Microbial Preparation(s) and/or Component(s)

The present disclosure provides systems and methods for assessing, characterizing, and identifying one or more microbial strains of a microbiome. For example, the present disclosure provides systems and methods for assessing, characterizing, and identifying one or more microbial strains of a microbiome that have one or more abilities. Such systems and methods can be useful for assessing, characterizing, and identifying one or more microbial strains that affect the health of humans, livestock, and/or pets. In some embodiments, one or more microbial strains affect the health of humans, livestock, and/or pets by modulating their respective metabolomes, cell viability, ATP levels, one or more other parameters or features (e.g. of an organ of a subject), or a combination thereof to prevent, treat, or reduce the risk of suffering from a disease, disorder, or condition. For example, technologies described herein may result in modulating the metabolome, improve cell viability, increase ATP levels, modulate one or more other parameters or features (e.g. microgliosis, Astrocytosis, proteasomal function, lysosomal function, inflammation, level or activity of a nucleic acid or protein, or form thereof, etc.), or a combination thereof of the subject that results in a decrease in production of toxic components and/or components that suggest or are a marker for cellular damage (e.g. neuronal cellular damage (e.g. increased blood levels of neurofilament light protein (NF-L)) in a subject (e.g. in blood of a subject).

The present disclosure also provides systems and methods for manufacturing a pharmaceutical composition that comprise assessing, characterizing, and identifying one or more microbial strains of a microbiome.

In some embodiments, assessing, characterizing, and identifying one or more microbial strains from a microbiome of a snake, lizard, fish, or bird. In some embodiments, assessing, characterizing, and identifying one or more microbial strains from a mammalian microbiome. A mammalian microbiome can be a canine, a feline, an equine, a bovine, an ovine, a caprine, or a porcine microbiome. In some embodiments, a microbiome used in a system or method described herein may prevent or treat a disease or condition.

A microbiome can be isolated from any system or tissue of an organism that supports microbial growth. For example, a microbiome can be a cutaneous microbiome, an oral microbiome, a nasal microbiome, a gastrointestinal microbiome, a brain microbiome, a pulmonary microbiome, or a urogenital microbiome. A list of exemplary microbial strains found in a gastrointestinal microbiome is included below in Table 1. A person skilled in the art would understand that a microbiome sample can be obtained by various ways known in the art. For example, a cutaneous, oral, nasal, pulmonary, or urogenital microbiome sample could be obtained using a swab or tissue scrapping. In some embodiments, a gastrointestinal microbiome could be sampled from feces. A cutaneous microbiome, an oral microbiome, a nasal microbiome, a gastrointestinal microbiome, a brain microbiome, a pulmonary microbiome, or a urogenital microbiome sample could be obtained via a biopsy.

In some embodiments, a microbiome is a microbiome of a healthy individual or an individual who does not suffer from or is not at risk of developing a particular disease or disorder. In some embodiments, a microbiome is a microbiome of an individual that suffers from or is at risk of developing a particular disease, disorder, or condition. In some embodiments, a microbiome is a microbiome of an individual who is known to suffer from a particular disease, disorder, or condition. In some embodiments, a human microbiome is a microbiome of a human with an unknown risk for one or more diseases, disorders, or conditions.

In some embodiments, a microbiome is a reference microbiome. A reference microbiome can be a microbiome of a healthy individual or an individual who does not suffer from or is not at risk of developing a particular disease, disorder, or condition. In some instances, a reference microbiome may be from the same individual as a microbiome to be assessed or characterized, but was obtained at a different time. In some instances, a reference microbiome may be from the same individual as a microbiome to be assessed or characterized, but was obtained from a different system or tissue.

In some embodiments, an individual microbial strain or a combination of microbial strains may be assessed, characterized, or identified in a different relative amount than such strain or strains are found in a microbiome. For example, the effect of modulation of a cell or organism in response to a single strain may be assessed, characterized, or identified using in vitro methods (e.g. mammalian cells) or in vivo methods using mammals (e.g. mice, humans, etc.) as described herein. In some embodiments, for example, the effect of modulation of a cell or organism to treat, prevent, or reduce the risk on a disease, disorder, or condition (e.g. a neurodegenerative disease, disorder, or condition as described herein) may be assessed, characterized, or identified using in vitro methods (e.g. mammalian cells) or in vivo methods using mammals (e.g. mice, humans, etc.) as described herein. In some embodiments, for example, the effect of modulation of a cell or organism to treat, prevent, or reduce the risk on a disease, disorder, or condition (e.g. a neurodegenerative disease, disorder, or condition as described herein) by modulating one or more metabolites of the cell or organism, one or features or parameters (e.g. cell viability, microgliosis, Astrocytosis, proteasomal function, lysosomal function, inflammation, ATP levels, level or activity of a nucleic acid or protein, or form thereof, etc.) of the cell or organism, or a combination thereof may be assessed, characterized, or identified using in vitro methods (e.g. mammalian cells) or in vivo methods using mammals (e.g. mice, humans, etc.) as described herein. As another example, the effect of modulation (e.g. of levels of one or more metabolites) of a cell or organism to treat, prevent, or reduce the risk on a disease, disorder, or condition, as described herein, in response to two microbial strains may be assessed, characterized, or identified together using methods described herein.

An extract, component, or compound of a microbial strain may also be assessed, characterized, or identified using methods described herein. In some cases, an extract, component, or compound of a microbial strain that has been determined to treat, prevent, or reduce the risk on a disease, disorder, or condition, as described herein, in an organism (e.g. mammal) may be assessed, characterized, or identified. Assessing, characterizing or identifying an extract, component, or compound of a microbial strain that treats, prevents, or reduces the risk on a disease, disorder, or condition in an organism (e.g. mammal) may provide additional information about potential biomarkers, targets, or protective agents in a microbiome.

A variety of technologies are known in the art that can be used to prepare extracts of microbial strains, and/or to isolate extracts, components, or compounds therefrom, or to process (e.g., to isolate and/or purify one or more components or compounds from). To give but a few examples, such technologies may include, for example, one or more of organic extraction, vacuum concentration, chromatography, and so on.

Assessing Biological Impact

The present disclosure provides the insight that compositions (e.g. microbiome compositions) as described herein can be used to treat, prevent, and/or reduce the risk of a disease, disorder, or condition of an organism (e.g. a mammal (e.g. a human)) by contacting the composition(s) (e.g., feeding the compositions to, administering to) with an organism. In some embodiments, an organism may suffer from or be at risk of suffering from a disease, disorder, or condition (e.g. mammalian disease, disorder, or condition). To determine whether one or more compositions treats, prevents, or reduces the risk of a disease, disorder, or condition (e.g. a neurodegenerative disease, disorder, or condition), levels of one or more metabolites can be observed, measured, or assessed in samples that have been contacted with the one or more compositions. For example, levels of the one or more metabolites can be observed, measured, or assessed in samples at different times (e.g. before administration of composition, after administration of composition, during administration of composition, etc.). To determine whether one or more compositions treats, prevents, or reduces the risk of a disease, disorder, or condition (e.g. a neurodegenerative disease, disorder, or condition), one or more features or parameters may be observed, measured, or assessed in samples that have been contacted with the one or more compositions. For example, one or more features or parameters may be observed, measured, or assessed in samples at different times (e.g. before administration of composition, after administration of composition, during administration of composition, etc.).

In some embodiments, methods described herein utilize a first sample and a second sample. In some embodiments, a first sample is a reference sample. In some embodiments, a reference sample can be a sample obtained from a subject who is contacted with (e.g., administered or fed) a composition, e.g., CT10 composition, CT6 composition, or CT6m composition. In some embodiments, a reference sample can be a sample obtained from a subject who is contacted with (e.g., administered or fed) a composition, e.g., CT10 composition, CT6 composition, or CT6m composition, at a first time point. In some embodiments, a reference sample can be a sample obtained from a subject prior to being contacted with (e.g., administered or fed) a composition, e.g., CT10 composition, CT6 composition, or CT6m composition. In some embodiments, a reference sample can be a sample obtained from a healthy individual. In some embodiments, a reference sample can be a sample obtained from an individual who is suffering from or may have a risk for a disease, disorder, or condition (e.g. neurodegenerative disease, disorder, or condition). In some embodiments, a reference sample is a control sample. In some embodiments, a reference sample is a negative control sample. In some embodiments, a reference sample is a positive control sample. In some embodiments, a reference sample may be a historic reference (e.g. value across control samples). In some embodiments, a reference sample may be from a printed publication (e.g. a text book, a journal, etc.).

In some embodiments, a second sample can be a test sample. In some embodiments, a test sample may be a sample obtained from a subject who is contacted with (e.g., administered or fed) a composition, e.g., CT10 composition, CT6 composition, or CT6m composition. In some instances, a subject (e.g. patient or population) may be suffering from or at risk of a disease, disorder, or condition (e.g. a neurodegenerative disease, disorder, or condition). In some instances, a subject (e.g. patient or population) may have an unknown risk for one or more diseases, disorders, or conditions as described herein. In some embodiments, a test can be a sample obtained from a subject who is contacted with (e.g., administered or fed) a composition, e.g., CT10 composition, CT6 composition, or CT6m composition, at a second time point.

In some embodiments, methods described herein comprise comparing one or more metabolite levels (e.g. a metabolome), or one or more parameters or features (e.g. cell viability, microgliosis, Astrocytosis, proteasomal function, lysosomal function, inflammation, ATP levels, level or activity of a nucleic acid or protein, or form thereof, etc.) obtained from a test sample with one or more metabolite levels (e.g. a metabolome), or one or more parameters or features (e.g. cell viability, microgliosis, Astrocytosis, proteasomal function, lysosomal function, inflammation, ATP levels, level or activity of a nucleic acid or protein, or form thereof, etc.) obtained from a reference sample. In some embodiments, by comparing one or more metabolite levels, parameters, or features obtained from a test sample with one or more metabolite levels, parameters, or features obtained from a reference sample, a composition described herein can be assessed, characterized or identified as being useful for treating, preventing, or reducing the risk of suffering from a disease, disorder, or condition (e.g. a neurodegenerative disease, disorder, or condition) as described herein. In some embodiments, by comparing one or more metabolite levels, parameters, or features obtained from a test sample with one or more metabolite levels, parameters, or features obtained from a reference sample, it can be determined that a composition as disclosed herein increases the severity or incidence of a disease, disorder, or condition phenotype. In some embodiments, by comparing one or more metabolite levels, parameters, or features obtained from a test sample with one or more metabolite levels, parameters, or features obtained from a reference sample, it can be determined that a composition as disclosed herein decreases the severity or incidence of a disease, disorder, or condition phenotype. In some embodiments, by comparing one or more metabolite levels, parameters, or features obtained from a test sample with one or more metabolite levels, parameters, or features obtained from a reference sample, it can be determined that a composition as disclosed herein has no effect on the severity or incidence of a disease, disorder, or condition phenotype. In some embodiments, by comparing one or more metabolite levels, parameters, or features obtained from a test sample with one or more metabolite levels, parameters, or features obtained from a reference sample, it can be determined that a composition as disclosed herein prevents a disease, disorder, or condition phenotype.

The present disclosure also provides the recognition that compositions and methods provided herein can be used to monitor progression of a disease, disorder, or condition (e.g. a neurodegenerative disease, disorder, or condition) in an individual. For example, if metabolite levels, parameters or features (e.g. cell viability, microgliosis, Astrocytosis, proteasomal function, lysosomal function, inflammation, ATP levels, level or activity of a nucleic acid or protein, or form thereof, etc.) determined to increase the severity of a disease, disorder, or condition decrease in relative amount, it may indicate that the disease, disorder, or condition is being attenuated, e.g., by treatment or immune response.

The present disclosure also provides the insight that compositions and methods provided herein can be used to tailor treatments (e.g., therapies, nutraceuticals, and/or probiotics) to an individual patient. In some embodiments, compositions and methods provided herein can provide "personalized" therapy. In some cases, metabolite levels, features or parameters (e.g. cell viability, microgliosis, Astrocytosis, proteasomal function, lysosomal function, inflammation, ATP levels, level or activity of a nucleic acid or protein, or form thereof, etc.) within an individual can be assessed, characterized, or identified to determine if they have a disease, disorder, or condition. Based on the results, the individual can be treated with one or more compositions to adjust the metabolite levels (i.e., their metabolome), features or parameters. In some instances, this will affect the disease, disorder, or condition the individual is suffering from or at risk of developing. For example, if an individual is determined to have a relatively low amount of one or more metabolite levels that have been determined to decrease the severity of a disease, disorder, or condition, administration of the one or more compositions that have been determined to decrease the severity of a disease, disorder, or condition to the individual (or an extract, component, or compound thereof) may attenuate the severity of the individual's disease or condition.

The present disclosure provides the insight that compositions and methods provided herein can be used recursively to treat, prevent, or ameliorate a disease, disorder, or condition. In some embodiments, for example, one or more compositions disclosed herein may be administered (e.g. fed, injected, etc.) to a subject after determining the effect of one or more compositions on subject's metabolite levels, or after determining the effect of one or more compositions on subject's features or parameters (e.g. cell viability, microgliosis, Astrocytosis, proteasomal function, lysosomal function, inflammation, ATP levels, level or activity of a nucleic acid or protein, or form thereof, etc.). In some embodiments, a composition may be administered once. In some embodiments, a composition may be administered more than once. In some embodiments, a composition may be administered daily, weekly, biweekly, monthly, bimonthly, etc. In each of these instances, levels of one or more metabolites, or changes in features or parameters may be monitored. In some embodiments, levels of one or more metabolites (e.g. metabolome) or changes in features or parameters may be monitored before administration of a composition. In some embodiments, levels of one or more metabolites (e.g. metabolome) or changes in features or parameters may be monitored after administration of a composition.

Pharmaceutical Compositions

Provided herein are compositions comprising individual microbial strains or combinations of microbial strains, metabolites thereof, extracts thereof, or components thereof. In some embodiments, a composition comprises individual microbial strains or combinations of microbial strains from a mammalian microbiome, metabolites thereof, extracts thereof, and/or components thereof, which have been assessed, identified, characterized or assayed using methods as described herein. In some embodiments, a composition provided herein comprises one or more, two or more, three or more, four or more, five or more, six or more, seven or more, eight or more, nine or more, or ten or more microbial strains from a mammalian microbiome, extracts thereof, metabolites thereof, and/or components thereof, which have been assessed, identified, characterized or assayed using methods as described herein.

Provided herein are also compositions comprising one or more components or metabolites. In some embodiments, components or metabolites in compositions herein are from a source that is not a microbial strain, e.g., synthetically generated. In some embodiments, components or metabolites in a composition may have been identified from a microbial strain, but are independent from a microbial strain and are not produced by a microbial strain, e.g., they can be synthetically generated.

In some embodiments, a composition provided herein comprises two or more, three or more, four or more, five or more, six or more, seven or more, eight or more, nine or more, or ten or more microbial strains listed in Table 1 below.

TABLE 1

Exemplary Microbial Strains Found in Human Gut Microbiome

*Bacteroides pectinophilus*
*Acetobacter* sp
*Acetobacterium tundrae*
*Achromobacter aegrifaciens*
*Achromobacter insuavis*
*Achromobacter piechaudii*
*Achromobacter xylosoxidans*
*Acidaminococcus fermentans*
*Acidaminococcus intestini*
*Acinetobacter baumannii*
*Acinetobacter junii*
*Actinomyces* sp.
*Agathobacter rectalis*
*Agathobaculum butyriciproducens*
*Aggregatibacter segnis*
*Akkermansia muciniphila*
*Alistipes finegoldii*
*Alistipes indistinctus*
*Alistipes onderdonkii*
*Alistipes putredinis*
*Alistipes shahii*
*Allisonella histaminiformans*
*Anaerobaculum hydrogeniformans*
*Anaerococcus hydrogenalis*
*Anaerococcus octavius*
*Anaerococcus prevotii*
*Anaerococcus tetradius*
*Anaerococcus vaginalis*
*Anaerofilum agile*
*Anaerofustis stercorihominis*
*Anaerosporobacter mobilis*
*Anaerostipes caccae*
*Anaerostipes hadrus*
*Anaerostipes rhamnosivorans*
*Anaerotruncus colihominis*
*Anaerovorax odorimutans*
*Arcobacter butzleri*
*Asaccharobacter celatus*
*Atopobium parvulum*
*Atopobium vaginae*
*Bacillus cereus*
*Bacillus coagulans*
*Bacillus licheniformis*

*Bacillus pseudomycoides*
*Bacillus sonorensis*
*Bacillus toyonensis*
*Bacillus wiedmannii*
*Bacteroides caccae*
*Bacteroides cellulosilyticus*
*Bacteroides clarus*
*Bacteroides coprocola*
*Bacteroides coprophilus*
*Bacteroides dorei*
*Bacteroides eggerthii*
*Bacteroides faecis*
*Bacteroides finegoldii*
*Bacteroides fluxus*
*Bacteroides fragilis*
*Bacteroides intestinalis*
*Bacteroides massiliensis*
*Bacteroides nordii*
*Bacteroides oleiciplenus*
*Bacteroides ovatus*
*Bacteroides plebeius*
*Bacteroides salanitronis*
Bacteroides salyersiae
*Bacteroides stercoris*
*Bacteroides thetaiotaomicron*
*Bacteroides uniformis*
*Bacteroides vulgatus*
*Bacteroides xylanisolvens*
*Bacteroides xylanolyticus*
*Barnesiella intestinihominis*
*Bartonella clarridgeiae*
*Bartonella quintana* str. *Toulouse*
*Bifidobacterium adolescentis*

*Exiguobacterium mexicanum*
*Faecalibacterium prausnitzii*
*Faecalitalea cylindroides*
*Finegoldia magna*
*Flavonifractor plautii*
*Flintibacter butyricus*
*Fusicatenibacter saccharivorans*
*Fusobacterium gonidiaformans*
*Fusobacterium mortiferum*
*Fusobacterium nucleatum*
*Fusobacterium ulcerans*
*Fusobacterium varium*
*Gardnerella vaginalis*
*Gemella haemolysans*
*Gemella sanguinis*
*Gemmiger formicilis*
*Gluconacetobacter* sp
*Gluconobacter* sp
*Gordonibacter pamelaeae*
*Granulicatella adiacens*
*Grimontia hollisae*
*Haemophilus parainfluenzae*
*Harryflintia acetispora*
*Helicobacter bilis*
*Helicobacter bizzozeronii*
*Helicobacter canadensis*
*Helicobacter cinaedi*
*Helicobacter pullorum*
*Helicobacter pylori*
*Helicobacter winghamensis*
*Holdemanella biformis*
*Holdemania filiformis*
*Holdemania massiliensis*
*Hungatella effluvii*
*Hungatella hathewayi*
*Intestinimonas butyriciproducens*
*Kineothrix alysoides*
*Kingella oralis*
*Klebsiella pneumoniae*
*Klebsiella pneumoniae* subsp. *ozaenae*
*Klebsiella pneumoniae* subsp. *pneumoniae*
*Klebsiella pneumoniae* subsp. *rhinoscleromatis*
*Klebsiella quasipneumoniae* subsp. *quasipneumoniae*
*Klebsiella singaporensis*
*Klebsiella variicola*
*Lachnobacterium bovis*
*Lachnospira multipara*
*Lachnospira pectinoschiza*
*Lactobacillus acidophilus*
*Lactobacillus amylolyticus*
*Lactobacillus amylovorus*
*Lactobacillus antri*
*Lactobacillus brevis* subsp. *Gravesensis*
*Lactobacillus buchneri*
*Lactobacillus casei*
*Lactobacillus coryniformis* subsp. *Coryniformis*
*Lactobacillus crispatus*
*Lactobacillus delbrueckii* subsp. *Bulgaricus*
*Lactobacillus delbrueckii* subsp. *indicus*
*Lactobacillus delbrueckii* subsp. *Lactis*
*Lactobacillus fermentum*
*Lactobacillus fructivorans*
*Lactobacillus gasseri*
*Lactobacillus helveticus*
*Lactobacillus hilgardii*
*Lactobacillus iners*
*Lactobacillus jensenii*
*Lactobacillus johnsonii*
*Lactobacillus mucosae*
*Lactobacillus oris*
*Lactobacillus paracasei*
*Lactobacillus paracasei* subsp. *tolerans*
*Lactobacillus pentosus*
*Lactobacillus plantarum* subsp. *plantarum*
*Lactobacillus reuteri*
*Lactobacillus rhamnosus*

TABLE 1-continued

Exemplary Microbial Strains Found in Human Gut Microbiome
TABLE 1

| | |
|---|---|
| Bifidobacterium angulatum | Lactobacillus rogosae |
| Bifidobacterium animalis | Lactobacillus ruminis |
| Bifidobacterium bifidum | Lactobacillus salivarius |
| Bifidobacterium breve | Lactobacillus ultunensis |
| Bifidobacterium catenulatum | Lactobacillus vaginalis |
| Bifidobacterium coryneforme | Lactococcus formosensis |
| Bifidobacterium dentium | Lactococcus garvieae |
| Bifidobacterium faecale | Lactococcus lactis subsp. Cremoris |
| Bifidobacterium gallicum | Lactococcus lactis subsp. lactis |
| Bifidobacterium longum | Lactonifactor longoviformis |
| Bifidobacterium longum subsp. infantis | Laribacter hongkongensis |
| Bifidobacterium longum subsp. longum | Lautropia mirabilis |
| Bifidobacterium longum subsp. suis | Leptotrichia buccalis |
| Bifidobacterium pseudocatenulatum | Leptotrichia hofstadii |
| Bifidobacterium pseudolongum | Leuconostoc lactis |
| Bifidobacterium stercoris | Leuconostoc mesenteroides subsp. Cremoris |
| Bilophila wadsworthia | Listeria grayi |
| Bittarella massiliensis | Listeria monocytogenes |
| Blautia coccoides | Longicatena caecimuris |
| Blautia faecis | Marvinbryantia formatexigens |
| Blautia glucerasea | Megamonas funiformis |
| Blautia hansenii | Megamonas rupellensis |
| Blautia hydrogenotrophica | Megasphaera elsdenii |
| Blautia luti | Megasphaera indica |
| Blautia obeum | Megasphaera micronuciformis |
| Blautia producta | Megasphaera paucivorans |
| Blautia schinkii | Methanobrevibacter smithii |
| Blautia stercoris | Methanomassiliicoccus luminyensis |
| Blautia wexlerae | Methanosphaera stadtmanae |
| Bradyrhizobium japonicum | Methylobacterium radiotolerans |
| Burkholderia ambifaria | Mitsuokella jalaludinii |
| Burkholderia cenocepacia | Mitsuokella multacida |
| Burkholderia glumae | Mobiluncus mulieris |
| Burkholderia multivorans | Mogibacterium timidum |
| Burkholderia plantarii | Mogibacterium vescum |
| Butyricicoccus faecihominis | Moraxella catarrhalis |
| Butyricicoccus pullicaecorum | Morganella morganii subsp. morganii |
| Butyricimonas faecihominis | Murdochiella asaccharolytica |
| Butyricimonas paravirosa | Mycobacterium abscessus |
| Butyricimonas virosa | Mycobacterium tuberculosis |
| Butyrivibrio crossotus | Mycoplasma hominis |
| Campylobacter coli | Neisseria cinerea |
| Campylobacter concisus | Neisseria flavescens |
| Campylobacter curvus | Neisseria macacae |
| Campylobacter gracilis | Neisseria mucosa |
| Campylobacter hominis | Neisseria sicca |
| Campylobacter jejuni subsp. Jejuni | Neisseria subflava |
| Campylobacter showae | Nitrobacter hamburgensis |
| Campylobacter upsaliensis | Nitrobacter winogradskyi |
| Candidatus Dorea massiliensis | Odoribacter laneus |
| Candidatus Stoquefichus massiliensis | Odoribacter splanchnicus |
| Capnocytophaga gingivalis | Olsenella profusa |
| Capnocytophaga sputigena | Olsenella scatoligenes |
| Cardiobacterium hominis | Olsenella uli |
| Catenibacterium mitsuokai | Oribacterium sinus |
| Catonella morbi | Oscillibacter ruminantium |
| Cedecea lapagei | Oscillibacter valericigenes |
| Citrobacter amalonaticus | Oscillospira guilliermondii |
| Citrobacter freundii | Oxalobacter formigenes |
| Citrobacter koseri | Paenibacillus jamilae |
| Citrobacter youngae | Paenibacillus kribbensis |
| Clostridium acetobutyricum | Paenibacillus riograndensis |
| Clostridium aerotolerans | Paeniclostridium sordellii |
| Clostridium aldenense | Parabacteroides distasonis |
| Clostridium aminophilum | Parabacteroides goldsteinii |
| Clostridium aminovalericum | Parabacteroides gordonii |
| Clostridium amygdalinum | Parabacteroides johnsonii |
| Clostridium asparagiforme | Parabacteroides merdae |
| Clostridium baratii | Paraprevotella clara |
| Clostridium bartlettii | Paraprevotella xylaniphila |
| Clostridium beijerinckii | Parasutterella excrementihominis |
| Clostridium bifermentans | Parasutterella secunda |
| Clostridium bolteae | Parvimonas micra |
| Clostridium butyricum | Pediococcus acidilactici |
| Clostridium celerecrescens | Pediococcus pentosaceus |
| Clostridium cf. saccharolyticum | Peptoniphilus duerdenii |
| Clostridium citroniae | Peptoniphilus grossensis |

TABLE 1-continued

Exemplary Microbial Strains Found in Human Gut Microbiome
TABLE 1

| | |
|---|---|
| Clostridium clariflavum | Peptoniphilus harei |
| Clostridium clostridioforme | Peptoniphilus indolicus |
| Clostridium cocleatum | Peptostreptococcus anaerobius |
| Clostridium colinum | Phascolarctobacterium faecium |
| Clostridium difficile | Phascolarctobacterium succinatutens |
| Clostridium glycyrrhizinilyticum | Porphyromonas asaccharolytica |
| Clostridium hathewayi | Porphyromonas endodontalis |
| Clostridium herbivorans | Porphyromonas gingivalis |
| Clostridium hiranonis | Prevotella bivia |
| Clostridium hylemonde | Prevotella buccae |
| Clostridium innocuum | Prevotella copri |
| Clostridium lactatifermentans | Prevotella disiens |
| Clostridium lavalense | Prevotella marshii |
| Clostridium leptum | Prevotella melaninogenica |
| Clostridium methoxybenzovorans | Prevotella nigrescens |
| Clostridium methylpentosum | Prevotella pallens |
| Clostridium nexile | Prevotella salivae |
| Clostridium orbiscindens | Prevotella stercorea |
| Clostridium oroticum | Prevotella tannerae |
| Clostridium perfringens | Prevotella timonensis |
| Clostridium polysaccharolyticum | Propionibacterium acnes |
| Clostridium propionicum | Propionibacterium avidum |
| Clostridium ramosum | Propionibacterium namnetense |
| Clostridium rectum | Proteus mirabilis |
| Clostridium saccharogumia | Proteus penneri |
| Clostridium saccharolyticum | Providencia alcalifaciens |
| Clostridium sardiniense | Providencia rettgeri |
| Clostridium saudii | Providencia rustigianii |
| Clostridium scindens | Providencia stuartii |
| Clostridium sordellii | Pseudoflavonifractor capillosus |
| Clostridium sphenoides | Ralstonia sp. |
| Clostridium spiroforme | Robinsoniella peoriensis |
| Clostridium sporogenes | Roseburia cecicola |
| Clostridium sticklandii | Roseburia faecis |
| Clostridium straminisolvens | Roseburia hominis |
| Clostridium symbiosum | Roseburia intestinalis |
| Clostridium tertium | Roseburia inulinivorans |
| Clostridium thermocellum | Rothia dentocariosa |
| Clostridium xylanolyticum | Ruminococcus albus |
| Clostridium xylanovorans | Ruminococcus bromii |
| Collinsella aerofaciens | Ruminococcus callidus |
| Collinsella intestinalis | Ruminococcus faecis |
| Collinsella stercoris | Ruminococcus gnavus |
| Collinsella tanakaei | Ruminococcus lactaris |
| Coprobacillus cateniformis | Ruminococcus obeum |
| Coprobacter fastidiosus | Ruminococcus torques |
| Coprococcus catus | Ruthenibacterium lactatiformans |
| Coprococcus comes | Sarcina ventriculi |
| Coprococcus eutactus | Sellimonas intestinalis |
| Corynebacterium ammoniagenes | Senegalimassilia anaerobia |
| Corynebacterium matruchotii | Shigella boydii |
| Corynebacterium pseudogenitalium | Shigella dysenteriae |
| Corynebacterium tuberculostearicum | Shigella flexneri |
| Deinococcus radiodurans | Shigella sonnei |
| Dermabacter hominis | Slackia faecicanis |
| Desulfotomaculum guttoideum | Slackia isoflavoniconvertens |
| Desulfovibrio legallis | Slackia piriformis |
| Desulfovibrio piger | Solobacterium moorei |
| Dialister invisus | Staphylococcus caprae |
| Dialister microaerophilus | Staphylococcus epidermidis |
| Dialister succinatiphilus | Staphylococcus hominis subsp. Hominis |
| Dielma fastidiosa | Staphylococcus lugdunensis |
| Dorea formicigenerans | Staphylococcus warneri |
| Dorea longicatena | Streptococcus agalactiae |
| Dysgonomonas mossii | Streptococcus anginosus |
| Edwardsiella tarda | Streptococcus anginosus subsp. whileyi |
| Eggerthella lenta | Streptococcus australis |
| Eggerthella sinensis | Streptococcus bovis |
| Eikenella corrodens | Streptococcus constellatus subsp. constellatus |
| Eisenbergiella tayi | Streptococcus equinus |
| Enhydrobacter aerosaccus | Streptococcus gallolyticus subsp. pasteuri |
| Enterobacter aerogenes | Streptococcus gallolyticus subsp. pasteurianus |
| Enterobacter asburiae | Streptococcus gordonii |
| Enterobacter cancerogenus | Streptococcus gordonii str. Challis |
| Enterobacter cloacae | Streptococcus infantarius |
| Enterobacter hormaechei | Streptococcus infantarius subsp. coli |
| Enterobacter kobei | Streptococcus infantarius subsp. Infantarius |

TABLE 1-continued

Exemplary Microbial Strains Found in Human Gut Microbiome
TABLE 1

| | |
|---|---|
| Enterobacter ludwigii | Streptococcus infantis |
| Enterobacter xiangfangensis | Streptococcus lactarius |
| Enterococcus asini | Streptococcus lutetiensis |
| Enterococcus avium | Streptococcus mutans |
| Enterococcus casseliflavus | Streptococcus parasanguinis |
| Enterococcus durans | Streptococcus pasteurianus |
| Enterococcus faecalis | Streptococcus pleomorphus |
| Enterococcus faecium | Streptococcus rubneri |
| Enterococcus gallinarum | Streptococcus salivarius |
| Enterococcus hirae | Streptococcus salivarius subsp. salivarius |
| Enterococcus mundtii | Streptococcus sanguinis |
| Enterococcus raffinosus | Streptococcus thermophilus |
| Enterococcus raffinosus | Streptococcus vestibularis |
| Erysipelotrichaceae bacterium | Subdoligranulum variabile |
| Escherichia albertii | Succinatimonas hippei |
| Escherichia coli | Sutterella parvirubra |
| Escherichia fergusonii | Sutterella stercoricanis |
| Eubacterium biforme | Sutterella wadsworthensis |
| Eubacterium callanderi | Terrisporobacter glycolicus |
| Eubacterium contortum | Turicibacter sanguinis |
| Eubacterium cylindroides | Ureaplasma parvum |
| Eubacterium desmolans | Vagococcus penaei |
| Eubacterium dolichum | Varibaculum cambriense |
| Eubacterium eligens | Veillonella sp. |
| Eubacterium hadrum | Veillonella dispar |
| Eubacterium hallii | Veillonella parvula |
| Eubacterium infirmum | Veillonella rogosae |
| Eubacterium limosum | Veillonella tobetsuensis |
| Eubacterium oxidoreducens | Vibrio cholerae |
| Eubacterium ramulus | Vibrio furnissii |
| Eubacterium rectale | Vibrio mimicus |
| Eubacterium ruminantium | Victivallis vadensis |
| Eubacterium saburreum | Weissella cibaria |
| Eubacterium siraeum | Weissella confusa |
| Eubacterium sulci | Weissella paramesenteroides |
| Eubacterium tortuosum | Xenorhabdus nematophila |
| Eubacterium ventriosum | Yersinia enterocolitica subsp. Palearctica |
| Eubacterium xylanophilum | Yersinia pseudotuberculosis |
| Eubacterium yurii subsp. Margaretiae | |

In some embodiments, a composition provided herein comprises Gluconacetobacter hansenii, Terrisporobacter glycolicus, Coprococcus sp., Lactobacillus plantarum, Clostridium butyricum, Paenibacillus sp., Veillonella sp., Bifidobacterium sp., Bacillus subtilis, Acidaminococcus sp., or a combination thereof. In some embodiments, a composition comprises at least two of, at least three of, at least four of, at least five of, at least six of, at least seven of, at least eight of, at least nine of, or all of Gluconacetobacter hansenii, Terrisporobacter glycolicus, Coprococcus sp., Lactobacillus plantarum, Clostridium butyricum, Paenibacillus sp., Veillonella sp., Bifidobacterium sp., Bacillus subtilis, and Acidaminococcus sp. In some embodiments, for example, a composition comprises all of Gluconacetobacter hansenii, Terrisporobacter glycolicus, Coprococcus sp., Lactobacillus plantarum, Clostridium butyricum, Paenibacillus sp., Veillonella sp., Bifidobacterium sp., Bacillus subtilis, and Acidaminococcus sp., and may be referred to by different names, including but not limited to, CT10 composition, CT10 cocktail, and so forth.

In some embodiments, a composition provided herein comprises Gluconacetobacter hanseni, Terrisporobacter glycolicus, Coprococcus sp., Lactobacillus plantarum, Veillonella sp., Bifidobacterium sp., or a combination thereof. In some embodiments, a composition comprises at least two of, at least three of, at least four of, at least five of, or all of Gluconacetobacter hanseni, Terrisporobacter glycolicus, Coprococcus sp., Lactobacillus plantarum, Veillonella sp., and Bifidobacterium sp. In some embodiments, for example, a composition comprises all of Gluconacetobacter hanseni, Terrisporobacter glycolicus, Coprococcus sp., Lactobacillus plantarum, Veillonella sp., and Bifidobacterium sp. and may be referred to by different names, including but not limited to, CT6 composition, CT6 cocktail, and so forth. In some embodiments, a composition provided herein comprises Gluconacetobacter hanseni, Terrisporobacter glycolicus, Coprococcus catus, Lactobacillus plantarum, Veillonella atypica, Bifidobacterium breve, or a combination thereof. In some embodiments, a composition comprises at least two of, at least three of, at least four of, at least five of, or all of Gluconacetobacter hanseni, Terrisporobacter glycolicus, Coprococcus catus, Lactobacillus plantarum, Veillonella atypica, and Bifidobacterium breve. In some embodiments, for example, a composition comprises all of Gluconacetobacter hanseni, Terrisporobacter glycolicus, Coprococcus catus, Lactobacillus plantarum, Veillonella atypica, and Bifidobacterium breve and may be referred to by different names, including but not limited to, CT6 composition, CT6 cocktail, and so forth.

In some embodiments, a composition provided herein comprises one or more, two or more, three or more, four or more, five or more, six or more, seven or more, eight or more, nine or more, or ten or more metabolites. Metabolites which may be assessed, identified, characterized, or assayed and/or comprised in compositions as disclosed herein, include those listed for example in the Appendices submitted herewith (e.g. Appendix 1-1, 1-2, 1-3, 2, 3, 4, or 5).

In some embodiments, a metabolite may be Butyrylcarnitine, Theobromine, p-Hydroxyphenylpyruvic acid, Propionic acid, Picolinic acid, 2-Hydroxy-4methylvaleric acid, N6-Acetylysine, Urocanic acid, N5-Ethylglutamine, Trigonelline, Stachydrine, Ectoine, 5-Hydroxylysine, Arginine (arg), Cholic acid, 2-(4-Hydroxyphenyl)propionic acid, N-Acetyltryptophan, Hydroxyproline, Argininosuccinic acid, Glutamic acid (Glu), Sarcosine, 5-Methoxyindoleacetic acid, Indole-3-lactic acid, Isovalerylalanine, N-Acetylleucine, 1-Methylhistidine, N-Acetylephenylalanine, Proline (Pro), or any combination thereof.

In some embodiments, a metabolite may be 4-Hydroxyphenylpyruvic, Ectoine, Gramine, N-Acetyl-L-phenylalanine, Nepsilon-Acetyl-L-lysine, Stachydrine, Trigonelline, 3-Ureidopropionic acid, Theobromine, Hippuric acid, Imidazolepropionic acid, NG-Methyl-L-arginine, trans-Urocanic Acid, N-Acetyl-L-leucine, Sarcosine, Isobutyrylcarnitine, b-Hydroxyisovaleric acid, L-Theanine/N5-Ethylglutamine, 5-Hydroxylysine, Phenaceturic acid, betaine, hydroxyproline, Picolinic acid, 2-Aminoadipic acid, Glycerophosphocholine, carnitine, Glycerol 3-phosphate, Argininosuccinic acid, creatine, Terephthalic acid, Homocitrulline, Mucic acid, Homocysteinesulfinic acid, Trimethyllysine, Spermidine, Glyoxylic acid, XA0013 C6H604S, 3-Indoxylsulfuric acid, Nicotinamide, N-Formylglycine, Ureidoglycolate, N-Methylproline, Glucaric acid, Butyrylcarnitine, Methionine sulfoxide, Carboxymethyllysine, Glycolic acid, Phenaceturic acid, Diethanolamine, Phosphorylcholine, Guanidinosuccinic acid, N-Acetylhistidine, Glyceric acid, S-Methylmethionine, Cysteine glutathione disulfide, Kynurenine, N-Acetylphenylalanine, Threonic acid, Malic acid, 7,8-Dihydrobiopterin, Homovanillic acid, Taurocholic acid, 5-Methoxyindoleacetic acid, butyrate, b-Hydroxyisovaleric acid, 2-Oxoglutaric acid, N-Acetyltryptophan, Thiaproline, Hypotaurine, Cholic acid, Acetoacetic acid, Ethanolamine, Guanidoacetic acid, S-Sulfocysteine, Myristic acid C14:0 XA0027, or any combination thereof.

In some embodiments, an individual microbial strain or combinations of microbial strains from a mammalian microbiome that have been killed (e.g., heat killed). Alternatively, in some embodiments, an individual microbial strain or combinations of microbial strains from a mammalian microbiome may include cells that are viable or alive.

In some embodiments, one or more microbial strains comprise a viable or living individual microbial strain or combinations of microbial strains, e.g., from a mammalian microbiome.

In some embodiments, one or more microbial strains comprise a viable or living individual microbial strain or combinations of microbial strains, e.g., from a mammalian microbiome, as described herein comprises and/or is formulated through use of one or more cell cultures and/or supernatants or pellets thereof, and/or a powder formed therefrom.

In some embodiments, compositions for use in accordance with the present disclosure are pharmaceutical compositions, e.g., for administration (e.g., topical, oral, subcutaneous, intravenous, intramuscular, intracerebral, intrathecal, rectal (e.g. rectal intubation), opthalmical, intravitreal, or suprachoroidal administration) to a mammal (e.g., a human). Pharmaceutical compositions typically include an active agent (e.g., individual microbial strains or combinations of microbial strains from a mammalian microbiome, extracts thereof, and/or components thereof), and a pharmaceutically acceptable carrier. Certain exemplary pharmaceutically acceptable carriers include, for instance saline, solvents, dispersion media, coatings, antibacterial and antifungal agents, isotonic and absorption delaying agents, and the like, compatible with pharmaceutical administration.

In some embodiments, a pharmaceutical composition for use in accordance with the present disclosure may include and/or may be administered in conjunction with, one or more supplementary active compounds; in certain embodiments, such supplementary active agents can include ginger, curcumin, probiotics (e.g, probiotic strains of one or more of the following genera: *Lactobacillus, Bifidobacterium, Saccharomyces, Enterococcus, Streptococcus, Pediococcus, Leuconostoc, Bacillus*, and/or *Escherichia coli* (see Fijan, Inti Environ Res Public Health. 2014 May; 11(5): 4745-4767, which is incorporated herein by reference in its entirety); prebiotics (non-digestible food ingredients that help support growth of probiotic bacteria, e.g., fructans such as fructooligosaccharides (FOS) and inulins, galactans such as galactooligosaccharides (GOS), dietary fibers such as resistant starch, pectin, beta-glucans, and xylooligosaccharides (Hutkins et al., Curr Opin Biotechnol. 2016 February; 37: 1-7, which is incorporated herein by reference in its entirety) and combinations thereof.

In some embodiments, a prebiotic comprises a fructooligosaccharide, an inulin, an isomaltooligosaccharide, a lactilol, a lactosucrose, a lactulose, a soy oligosaccharide, a transgalactooligosaccharide, a xylooligosaccharide, seaweed, or a combination thereof. In some embodiments, a prebiotic comprises seaweed. In some embodiments, a prebiotic comprises a pome extract, berry extract and walnut extract.

In some embodiments, a probiotic composition can be formulated for oral administration. In some embodiments, a probiotic composition can be a food, a beverage, a feed composition, or a nutritional supplement. In some embodiments, an ellagitannin composition, an enzymatic composition, or both can be a liquid, syrup, tablet, troche, gummy, capsule, powder, gel, or film. In some embodiments, a probiotic composition is an enteric-coated formulation.

In some embodiments, a probiotic comprises a prebiotic. In some embodiments, a prebiotic comprises a fructooligosaccharide, an inulin, an isomaltooligosaccharide, a lactilol, a lactosucrose, a lactulose, a soy oligosaccharide, a transgalactooligosaccharide, a xylooligosaccharide, seaweed, a pome extract, berry extract and walnut extract. or a combination thereof.

Pharmaceutical compositions are typically formulated to be compatible with its intended route of administration. Examples of routes of administration include topical, oral, subcutaneous, intravenous, intramuscular, intracerebral, intrathecal, rectal, (e.g. rectal intubation), opthalmical, intravitreal, or suprachoroidal administration. Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY), which is incorporated in its entirety by reference herein. Oral compositions generally include an inert diluent or an edible carrier (e.g. pharmaceutically acceptable diluent, pharmaceutically acceptable carrier). To give but a few examples, in some embodiments, an oral formulation may be or comprise a syrup, a liquid, a tablet, a troche, a gummy, a capsule, e.g., gelatin capsules, a powder, a gel, a film, etc. Similarly, ocular compositions (e.g. for ophthalmic, intravitreal, or suprachoroidal administration) may include an inert diluent or carrier (e.g. pharmaceutically acceptable diluent, pharmaceutically acceptable carrier), various additives such as viscosity enhancers, permeations enhancers, cyclodextrins, etc. Examples of viscosity enhancers include hydroxy methyl cellulose, hydroxy ethyl cellulose, sodium carboxy methyl cellulose, hydroxypropyl methyl cellulose and polyalcohol. Example of permeation enhancers include chelating agents, preservatives, surface active agents, bile salts, Benzalkonium chloride, polyoxyethylene glycol ethers (lauryl, stearyl and oleyl), ethylenediaminetetra acetic acid sodium salt, sodium taurocholate, saponins and cremophor EL, etc. For example, in some embodiments ocular formulations may be or comprise suspensions, emulsions (e.g. water-in-oil or oil-in water), nanocarriers, (e.g. nanoparticles, nanosuspensions, liposomes, nanomicelles, dendrimers, etc.) ointments, gels, eye drops, etc. Cerebral compositions (e.g. for intracerebral or intrathecal administration) may include an inert diluent or carrier, and/or additives. In some embodiments, cerebral compositions are free of preservatives. In some embodiments, cerebral compositions are sterile.

In some embodiments, pharmaceutically compatible binding agents, and/or adjuvant materials can be included as part of a pharmaceutical composition. In some particular embodiments, a pharmaceutical composition can contain, e.g., any one or more of the following inactive ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. In some embodiments, the compositions can be taken as-is or sprinkled onto or mixed into a food or liquid (such as water). In some embodiments, a composition that may be administered to mammals as described herein may be or comprise an ingestible item (e.g., a food or drink) that comprises (e.g., is supplemented) with an individual microbial strain or combinations of microbial strains from a mammalian microbiome, extracts thereof, and/or components thereof.

In some embodiments, a food can be or comprise one or more of bars, candies, baked goods, cereals, salty snacks, pastas, chocolates, and other solid foods, as well as liquid or semi-solid foods including yogurt, soups and stews, and beverages such as smoothies, shakes, juices, and other carbonated or non-carbonated beverages. In some embodiments, foods are prepared by a subject by mixing in individual microbial strains or combinations of microbial strains from a mammalian microbiome, extracts thereof, and/or components thereof.

Compositions can be included in a kit, container, pack, or dispenser, together with instructions for administration or for use in a method described herein.

Those skilled in the art, reading the present disclosure, will appreciate that, in some embodiments, a composition (e.g., a pharmaceutical composition) as described herein may be or comprise one or more cells, tissues, or organisms (e.g., plant or microbe cells, tissues, or organisms) that produce (e.g., have produced, and/or are producing) a relevant compound.

Those skilled in the art will appreciate that, in some embodiments, technologies for preparing compositions and/or preparations, and/or for preparing (and particularly for preparing pharmaceutical compositions) may include one or more steps of assessing or characterizing a compound, preparation, or composition, e.g., as part of quality control. In some embodiments, if an assayed material does not meet pre-determined specifications for the relevant assessment, it is discarded. In some embodiments, if such assayed material does meet the pre-determined specifications, then it continues to be processed as described herein.

In some embodiments, a pharmaceutical composition provided herein can promote the colonization of an individual microbial strain or combinations of microbial strains from a mammalian microbiome, particularly microbial strain(s) that have been identified, characterized, or assessed as decreasing the severity or incidence of a mammalian disease, disorder, or condition, in a mammal suffering from or at risk of the mammalian disease, disorder, or condition. In some embodiments, a pharmaceutical composition provided herein can attenuate the colonization of an individual microbial strain or combinations of microbial strains from a mammalian microbiome, particularly microbial strain(s) that have been identified, characterized, or assessed as increasing the severity or incidence of a mammalian disease, disorder, or condition, in a mammal suffering from or at risk of the mammalian disease, disorder, or condition (e.g. a neurodegenarative disease, disorder, or condition). In some embodiments, a pharmaceutical composition provided herein can promote the colonization of an individual microbial strain or combinations of microbial strains from a mammalian microbiome, particularly microbial strain(s) that have been identified, characterized, or assessed as not affecting the severity or incidence of the mammalian disease, disorder, or condition but have been identified, characterized, or assessed as being capable of outcompeting one or more microbial strains that have been identified, characterized, or assessed as increasing the severity or incidence of a mammalian disease, disorder or condition, in a mammal suffering from or at risk of the mammalian disease, disorder, or condition.

In some embodiments, each of the one or more microbial strains in a composition comprises $10^1$ colony forming units (CFUs) to $10^{20}$ CFU. In some embodiments, each of the one or more microbial strains in a composition comprises $10^1$ colony forming units (CFUs) to $10^{15}$ CFU. In some embodiments, each of the one or more microbial strains in a composition comprises $10^6$ CFU to $10^{15}$ CFUs. In some embodiments, each of the one or more microbial strains in a composition comprises about $10^1$ CFU to $10^{15}$ CFU, or about $10^2$ CFU to $10^{14}$ CFU, or about $10^3$ CFU to $10^{13}$ CFU, or about $10^4$ CFU to $10^{13}$ CFU, or about $10^5$ CFU to $10^{12}$ CFU, or about $10^6$ CFU to $10^{11}$ CFU, or about $10^7$ CFU to $10^{10}$ CFU, or about $10^8$ CFU to $10^9$ CFU, or about $10^5$ CFU to $10^{10}$ CFU, or about $10^8$ CFU to $10^{12}$ CFU. In some embodiments, each of the one or more microbial strains in a composition comprises at least about $10^1$, $5\times10^1$, $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, $10^{10}$, $5\times10^{10}$, $10^{11}$, $5\times10^{11}$, $10^{12}$, or more CFUs. In some embodiments, each of the one or more microbial strains in a composition comprises at most about $10^{15}$, $5\times10^{14}$, $10^{14}$, $5\times10^{13}$, $10^{13}$, $5\times10^{12}$, $10^{12}$, $5\times10^{11}$, $10^{11}$, $5\times10^{10}$, $10^{10}$, $5\times10^9$, $10^9$, $5\times10^8$, $10^8$, or less CFUs. In some embodiments, each of the one or more microbial strains in a composition comprises the same number of CFUs. In some embodiments, some of the one or more microbial strains in a composition comprises a different number of CFUs.

In some embodiments, a composition comprises a total of $10^1$ CFU to $10^{20}$ CFUs. In some embodiments, a composition comprises a total of $10^6$ CFU to $10^{15}$ of CFUs. In some embodiments, a composition can include about $10^1$ CFU to $10^{20}$ CFU, or about $10^5$ CFU to $10^{15}$ CFU, or about $10^5$ CFU to $10^{12}$ CFU, about $10^5$ CFU to $10^{10}$ CFU, or about $10^8$ CFU to $10^{12}$ CFU of one or more microbial strains. In some embodiments, a composition can include about $10^1$ CFU to $10^{15}$ CFU, or about $10^2$ CFU to $10^{14}$ CFU, or about $10^3$ CFU to $10^{13}$ CFU, or about $10^4$ CFU to $10^{13}$ CFU, or about $10^5$ CFU to $10^{12}$ CFU, or about $10^6$ CFU to $10^{11}$ CFU, or about $10^2$ CFU to $10^{10}$ CFU, or about $10^8$ CFU to $10^9$ CFU, or about $10^5$ CFU to $10^{10}$ CFU, or about $10^8$ CFU to $10^{12}$ CFU of one or more microbial strains. In some embodiments, a composition can include at least $10^1$, $5\times10^1$, $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $10^9$, $5\times10^9$, $10^{10}$, $5\times10^{10}$, $10^{11}$, $5\times10^{11}$, $10^{12}$, or more CFUs of one or more microbial strains. In some embodiments, a composition can include at most $10^{15}$, $5\times10^{14}$, $10^{14}$, $5\times10^{13}$, $10^{13}$, $5\times10^{12}$, $10^{12}$, $5\times10^{11}$, $10^{11}$, $5\times10^{10}$, $10^{10}$, $5\times10^9$, $10^9$, $5\times10^8$, $10^8$, or less CFUs of one or more microbial strains.

In some embodiments, a pharmaceutical composition is tailored to a specific mammal (e.g., a specific human, e.g., a patient) based on that mammal's (e.g., human's) microbiome. In some embodiments, a pharmaceutical composition is specific for a microbiome of an individual mammal (e.g., human). In some embodiments, a pharmaceutical composition is specific for microbiomes of a population of mammals (e.g., humans). Populations of mammals can include, but are not limited to: families, mammals in the same regional location (e.g., neighborhood, city, state, or country), mammals with the same disease or condition, mammals of a particular age or age range, mammals that consume a particular diet (e.g., food, food source, or caloric intake).

Methods of Treatment

The present disclosure recognizes that compositions described herein can be useful in the treatment of subjects. Methods provided by the present disclosure include methods for the treatment of certain diseases, disorders and conditions. In some embodiments, relevant diseases, disorders and conditions may be or include a neurodegenerative disease, disorder, or condition. In some embodiments, a neurodegenerative disease, disorder, or condition may be ALS, AD, PD, or HD.

Generally, methods of treatment provided by the present disclosure involve administering a therapeutically effective amount of a composition as described herein alone or in combination with other compositions and/or treatments to a subject who is in need of, or who has been determined to be in need of, such treatment.

In some embodiments, methods of treatment provided herein are prophylactic or preventative, e.g., may be administered to subjects prior to display of significant symptoms and/or to exposure to a particular expected inducement that is associated with neurodegenerative diseases, disorders, or conditions described herein. In some embodiments, methods of treatment provided herein are therapeutic, e.g., may be administered to subjects after development of significant symptoms associated with neurodegenerative diseases, disorders, or conditions.

In some embodiments, provided methods of treatment are administered to a subject that is a mammal, e.g., a mammal that experiences a disease, disorder, or condition as described herein; in some embodiments, a subject is a human or non-human veterinary subject, e.g., an ape, cat dog, monkey, or pig.

In many embodiments, treatment involves ameliorating at least one symptom of a disease, disorder, or condition associated with neurodegenerative diseases, disorders, or conditions. In some embodiments, a method of treatment can be prophylactic.

In some embodiments, the methods can include administration of a therapeutically effective amount of compositions disclosed herein before, during (e.g., concurrently with), or after administration of a treatment that is expected to be associated with neurodegenerative diseases, disorders, or conditions.

In some embodiments, subjects who receive treatment as described herein may be receiving and/or may have received other treatment (e.g., pharmacological treatment/therapy, surgical, etc.), for example that may be intended to treat one or more symptoms or features of a disease disorder or condition as described herein (e.g. neurodegenerative diseases, disorders, or conditions), so that provided compositions are administered in combination with such other therapy (i.e. treatment) to treat the relevant disease, disorder, or condition.

In some embodiments, the compositions described herein can be administered in a form containing one or more pharmaceutically acceptable carriers. Suitable carriers have been described previously and vary with the desired form and mode of administration of a composition. For example, pharmaceutically acceptable carriers can include diluents or excipients such as fillers, binders, wetting agents, disintegrators, surface-active agents, glidants, and lubricants. Typically, a carrier may be a solid (including powder), liquid, or any combination thereof. Each carrier is preferably "acceptable" in the sense of being compatible with other ingredients in the composition and not injurious to a subject. A carrier can be biologically acceptable and inert (e.g., it permits the composition to maintain viability of the biological material until delivered to the appropriate site).

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

Oral compositions can include an inert diluent or an edible carrier. For purposes of oral therapeutic administration, an active compound can be incorporated with excipients and used in the form of tablets, lozenges, pastilles, troches, or capsules, e.g., gelatin capsules. Oral compositions can also be prepared by combining a composition of the present disclosure with a food. In some embodiments, microbes (e.g. one or more microbial strains) can be formulated in a food item. Some non-limiting examples of food items to be used with the methods and compositions described herein include: popsicles, cheeses, creams, chocolates, milk, meat, drinks, pickled vegetables, kefir, miso, sauerkraut, etc. In other embodiments, food items can be juices, refreshing beverages, tea beverages, drink preparations, jelly beverages, and functional beverages; alcoholic beverages such as beers; carbohydrate-containing foods such as rice food products, noodles, breads, and pastas; paste products such as fish, hams, sausages, paste products of seafood; retort pouch products such as curries, food dressed with a thick starchy sauce, and Chinese soups; soups; dairy products such as milk, dairy beverages, ice creams, and yogurts; fermented products such as fermented soybean pastes, fermented beverages, and pickles; bean products; various confectionery products including biscuits, cookies, and the like, candies, chewing gums, gummies, cold desserts including jellies, cream caramels, and frozen desserts; instant foods such as instant soups and instant soy-bean soups; and the like. It is preferred that food preparations not require cooking after admixture with microbial strain(s) to avoid killing any microbes. In one embodiment a food used for administration is chilled, for example, iced flavored water. In certain embodiments, the food item is not a potentially allergenic food item (e.g., not soy, wheat, peanut, tree nuts, dairy, eggs, shellfish or fish). Pharmaceutically compatible binding agents, and/or adjuvant materials can be included as part of the composition.

Ocular formulations (e.g. for ophthalmic, intravitreal, or suprachoroidal administration) can include an inert diluent or a carrier. For purposes of ocular therapeutic administration, an active compound can be incorporated with excipients and used in the form of suspensions, emulsions (e.g. water-in-oil or oil-in water), nanocarriers, (e.g. nanoparticles, nanosuspensions, liposomes, nanomicelles, dendrimers, etc.) ointments, gels, eye drops, etc. In some embodiments, administration of such formulations is topical (e.g. eye drops). In some embodiments, administration of such formulations is via injection (e.g. intravitreal, suprachoroidal, etc.).

Cerebral formulations (e.g. for intracerebral or intrathecal administration) can include an inert diluent or a carrier. For purposes of cerebral therapeutic administration, an active compound can be incorporated with excipients and used in the form of suspensions, emulsions (e.g. water-in-oil or oil-in water), nanocarriers, (e.g. nanoparticles, nanosuspensions, liposomes, nanomicelles, dendrimers, etc.) ointments, gels, etc. In some embodiments, administration of such formulations is topical (e.g. ointments). In some embodiments, administration of such formulations is via injection (e.g. intracerebral, intrathecal, etc.).

In some such embodiments, a composition described herein is administered to a subject according to a dosing regimen that achieves population of the subject's microbiome with administered cells. In some embodiments, a composition is administered to a subject in a single dose. In some embodiments, a composition is administered to a subject in a plurality of doses. In some embodiments, a dose of a composition is administered to a subject twice a day, daily, weekly, or monthly.

In some embodiments, each of the one or more microbial strains in a dose comprises $10^1$ to $10^{15}$ colony forming units (CFUs). In some embodiments, each of the one or more microbial strains in a dose comprises $10^6$ to $10^{15}$ CFUs. In some embodiments, each of the one or more microbial strains in a dose comprises the same number of CFUs. In some embodiments, some of the one or more microbial strains in a dose comprises a different number of CFUs.

In some embodiments, a dose of one or more microbial strains comprises a total of $10^6$ to $10^{15}$ CFUs. In some embodiments, a dose of one or more microbial strains comprises a total of $10^7$ to $10^{15}$ CFUs. In some embodiments, a dose of one or more microbial strains comprises 5-200 billion CFUs. In some embodiments, a dose of one or more microbial strains comprises 5-50 billion CFUs. In some embodiments, a dose of one or more microbial strains comprises 5-20 billion CFUs. In some embodiments, a dose of one or more microbial strains comprises 50-100 billion CFUs. In some embodiments, a dose of one or more microbial strains comprises 100-200 billion CFUs.

In some embodiments, efficacy can be assessed by measuring the degree of oxidative stress of cells in a biological sample prior to and following administration of a composition as described herein. The degree of oxidative stress of cells can be assessed by, for example, measuring the expression of oxidative stress biomarkers, such as reactive oxygen species (ROS) levels, or lipid, protein, and nucleic acid damage levels, or by determining the ratio of oxidized to reduced forms of one or more biomarkers. High levels of oxidative stress can be cytotoxic, so the degree of oxidative stress can be measured by assessing the concentration of intracellular proteins present in the systemic circulation from inflamed or lysed cells (e.g. nerve cells).

EXEMPLIFICATION

In-depth details of the purpose, mouse model used, studies performed, and the results of Examples 1-5 are listed in Appendix 5 filed herewith.

Example 1: Evaluation of Efficacy of Microbiome Compositions in ALS Male Mouse Model In-depth details of the purpose, mouse model used, studies performed, and the results of this Example is listed in Appendix 5 filed herewith.

This Example provides an evaluation of the efficacy of microbiome compositions, specifically CT6 and CT6m compositions, in in vivo male mouse model for ALS.

Mouse Model: Superoxide dismutase (SOD), also known as superoxide dismutase 1 or SOD1, is an enzyme that in humans is encoded by the SOD1 gene, and is implicated in apoptosis and familial ALS. The SOD1-G93A (or G93A-SOD1, or SOD1$^{G93A}$) transgene was designed with a mutant human SOD1 gene (harboring a single amino acid substitution of glycine to alanine at codon 93) driven by its endogenous human SOD1 promoter. This transgene was injected into fertilized B6SJLF1 mouse eggs and founder animals were obtained. Transgenic mice on a mixed B6SJL genetic background were sent to The Jackson Laboratory.

ALS-SOD1 mice, with the aforementioned genetic background, that were between 49-63 days were used for all experiments. This mouse model is the most popular transgenic mice with a 4-fold increase in SOD activity and exhibits a phenotype akin to ALS in humans. Wild type mice were used as a control in all experiments.

Study: Male mice were divided into four groups of 13-15 animals per group, and were provided mock (DPBS) or microbiome composition (CT6 or CT6m; composition details listed in Tables 2 and 3 below) by daily oral gavage. The groups were: (i) G1: Wild type mice treated with DPBS; (ii) G2: SOD1 transgenic mice treated with DPBS; (iii) G3: SOD1 transgenic mice treated with CT6 composition; and (iv) G4: SOD1 transgenic mice treated with CT6m composition. The animals were sacrificed when they reached a NeuroScore (NS) of 4 (see Appendix 5 for details), following which survival analysis, histological and biochemical analyses were performed.

TABLE 2

| | CT6 Composition | |
|---|---|---|
| # | MBT | Concentration in CFU/ml |
| 1 | Bifidobacterium breve | $1 \times 10^9$ |
| 2 | Gluconacetobacter hansenii | $1 \times 10^9$ |
| 3 | Terrisporobacter glycolicus | $1 \times 10^9$ |
| 4 | Veillonella atypica | $1 \times 10^9$ |
| 5 | Lactobacillus plantarum | $1 \times 10^9$ |
| 6 | Coprococcus catus | $1 \times 10^9$ |

TABLE 3

CT6m Composition

| # | MBT | Concentration in CFU/ml |
|---|---|---|
| 1 | *Bifidobacterium breve* | $1 \times 10^9$ |
| 2 | *Gluconacetobacter hansenii* | $3 \times 10^9$ |
| 3 | *Terrisporobacter glycolicus* | $1 \times 10^9$ |
| 4 | *Veillonella atypica* | $3 \times 10^9$ |
| 5 | *Lactobacillus plantarum* | $1 \times 10^9$ |
| 6 | *Coprococcus catus* | $1 \times 10^9$ |

Results:

Microgliosis in Spinal Cord: Tissue samples from the lumbar spinal cord of the mice in each group were examined for microgliosis, a key marker for neuroinflammation by anti-IBA1 staining and fluorescence imaging. As shown in FIG. 1AA, FIG. 1AB, and FIG. 1B, mice in group 2 i.e. SOD1 mice that were mock-treated showed higher levels of microgliosis as compared to wild-type mice in group 1. Furthermore, treatment with CT6 and CT6m microbiome cocktails (i.e. mice in groups 3 and 4) showed a reduction in microgliosis as evidenced by the reduced fluorescent intensity of lumbar spinal cord tissue of mice in groups 3 and 4. In fact, treatment with CT6 and CT6m cocktails resulted in restored microglia levels to near normal (compared to wild type mice of group 1) from the 1.5× increase seen in ALS-SOD1 control group 2.

Astrocytosis in the Spinal Cord: Tissue samples from the lumbar spinal cord of the mice in each group were examined for astrocytosis, another key marker for neuroinflammation by anti-GFAP staining and fluorescence imaging. As shown in FIG. 2AA, FIG. 2AB, and FIG. 2B, mice in group 2, i.e., SOD1 mice that were mock-treated showed very high levels of astrocytosis as compared to wild-type mice in group 1. Furthermore, treatment with CT6 and CT6m microbiome cocktails (i.e. mice in groups 3 and 4) showed a reduction in astrocytosis as evidenced by the reduced fluorescent intensity of lumbar spinal cord tissue of mice in groups 3 and 4. In fact, treatment with CT6 and CT6m cocktails resulted in restored Astrocyte levels to near normal (compared to wild type mice of group 1) from the 3× increase seen in ALS-SOD1 control group 2.

ATP Production in Apical Spinal Cord: Spinal cord lysate from the apical spinal cord of the mice in each group were examined for ATP levels. Spinal cord protein lysates were prepared using PhosphoSafe™ extraction reagent (EMD Millipore, catalogue 71296) and mechanically homogenized using bead-filled Lysing Matrix D tubes (MP Biomedicals, Illkirch, France). ATP production is a key marker for neurodegeneration, as individuals with neurodegenerative diseases, disorders, or conditions such as ALS, PD and AD, are known to have damaged mitochondria which leads to decreased ATP production. As shown in FIG. 3, treatment with CT6 and CT6m microbiome cocktails (i.e. mice in groups 3 and 4) showed increased production of ATP by approximately 2× compared to wild type mice of group 1 and ALS-SOD1 mice of group 2.

Plasma Neurofilament light protein (NF-L) levels: Blood plasma from mice in each group were examined for Neurofilament light-chain (NF-L) protein levels. Death of motor neurons in the spinal cord is a hallmark feature of SOD1$^{G93A}$ model. NF-L is the product of axonal and neuronal damage that makes its way into the blood stream. NF-L is a well validated biomarker for assessing neurodegenerative disease progression, and higher levels of plasma NF-L levels are associated with death of neurons and increased severity of disease (Loeffler et al., Front Neurosci 14, 579, 2020). ALS, PD, and AD patients show increased blood levels of NF-L. Plasma NF-L levels of the mice in each of the four groups were determined as per the protocol in the NF-L ELISA kit (Abbexa; abx154439). As shown in FIG. 4, compared to the wild-type mice of group 1, the plasma levels of NF-L were significantly higher in SOD1$^{G93A}$ mice of group 2 (approximately 1.8× the plasma levels of wild-type mice) indicating significantly higher death of motor neurons. However, CT6 or CT6m treated mice of groups 3 and 4 showed significantly lower blood levels of NF-L compared to mock-treated SOD1$^{G93A}$ mice suggesting less motor neuron death. As seen from FIG. 4, NF-L levels in microbiome composition-treated mice (i.e. of groups 3 and 4) were reduced on average from 1.8× (of mock-treated mice in group 2) to 1.35× the plasma levels of wild-type mice.

NMJ Innervation of Tibialis Anterior Muscle: Neuromuscular (NMJ) integrity is a key marked for neuromuscular activity. It is the site for the transmission of action potential from nerve to the muscle. It was observed that CT6 or CT6m administration improved NMJ integrity in SOD1$^{G93A}$ mice in the tibialis anterior muscle. A significant decrease in the overlap between presynaptic (vesicular acetylcholine transporter; VAChT) and postsynaptic (a-bungarotoxin; a-BTX, which binds to the nicotinic acetylcholine transporter) was observed in mock-treated SOD1$^{G93A}$ mice of group 2 compared to that of wild-type mice of group 1 suggesting decreased innervation. By contrast, in CT6 or CT6m treated animals of groups 3 and 4, a significant increase in the overlap between VAChT and a-BTX was observed suggesting increased NMJ innervation. This result suggests that CT6 or CT6m administration preserves NMJ innervation (see FIG. 5).

Each dot in the FIG. 5 represents NMJ from at least 4 animals. Fluorescence intensity of each VAChT and a-BTX were measured and the ratio between them used to calculate the % overlap. The middle line in the box and whisker plot represents the mean value. ****$p<0.0001$. As shown in FIG. 5, treatment with CT6 and CT6m resulted in a 2× increased in innervated NMJ level compared to that of untreated SOD1$^{G93A}$ mice of group 2.

Proteasomal Function in Spinal Cord: Neurons depend on the ubiquitin-proteasome system (UPS) and autophagy-associated lysosomal degradation for protein degradation and removal. The UPS is the main intracellular proteolytic system responsible for the maintenance of protein turnover and for the selective removal of damaged proteins (Glickman and Ciechanover, Physiol Rev 82, 373-428, 2002). Notably, ubiquitin-rich protein inclusions are frequently observed in ALS patients (Migheli et al., Neurosci Lett 114, 5-10, 1990), while proteasomal activity is significantly reduced and/or impaired in the spinal cords the SOD1$^{G93A}$ mouse model of ALS (Kabashi et al., J Neurochem 105, 2353-2366, 2008). While inhibition of proteasomal activity increases SOD1 aggregates, restoring proteasomal function reduces the level of protein aggregates (Puttaparthi et al., J Neurochem 87, 851-860, 2003). Thus, improving or restoring proteasomal function as a mechanism to reduce the accumulation of misfolded proteins is an alluring therapeutic approach. Upregulation of regulatory subunits of proteasome such as PSMD11 has been shown to increase the assembly and functional activity of proteasome and results in clearance of polyubiquitinated substrates (Vilchez et al., Nature 489, 263-268, 2012).

To determine whether CT6 or CT6m treatment affect proteasomal function, PSMD11 protein levels in the spinal cord of SOD1-G93A mice were quantified by western blot.

Spinal cord protein lysates were prepared using PhosphoSafe™ extraction reagent (EMD Millipore, catalogue 71296) and mechanically homogenized using bead-filled Lysing Matrix D tubes (MP Biomedicals, Illkirch, France). Protein concentration was determined by the Bradford method using the BioRad Protein assay reagent. 30 mg of total protein was mixed with SDS sample buffer and boiled for 10 min. The samples were electrophoresed on custom-made SDS-Polyacrylamide Bis-tris gels (4-12%) using the MOPS or MES running buffer followed by transfer onto PVDF membrane (Invitrogen) using iBlot2 (Invitrogen). The membrane was blocked using Odyssey blocking buffer for 1 hour and incubated with PSMD11 specific antibody (Catalog #NBP1-30252, Novus Biologicals) at 1:1000 dilution overnight under shaking conditions at 4° C. The following day, the membrane was thoroughly washed in TBST (TBS+ Tween 20) and incubated in HRP conjugated secondary antibody (Catalog #7076; Cell signaling) at 1:2000 dilution at room temperature for 1 hour. Densitometric quantification of the immunoblots was performed by GeneTools from Syngene after visualizing with GBox Mini (SYNGENE). Target bands were normalized using their respective b-actin loading controls. Each dot in the plot of FIG. 6A represents pooled spinal cord lysates from two animals. PSMD11 protein level is significantly decreased in the spinal cord lysates of SOD1$^{G93A}$ mice compared to the wild-type mice. However, CT6 or CT6m treated mice had significantly increased PSMD11 protein levels compared to mock-treated SOD1$^{G93A}$ mice. PSMD11 protein levels in the spinal cord lysates of CT6 or CT6m treated SOD1$^{G93A}$ mice were at least 1.5× to 2× to that of the levels in wild-type mice. Statistical analyses were performed in GraphPad Prism. Data sets were analyzed by one-way ANOVA followed by Dunnett's test. Data represented as Mean±SEM. A level of p<0.05 was considered statistically significant. Compared to the group 2 (i.e. G2), group 3 (i.e. G3) and group 4 (i.e. G4) had significantly elevated levels of PSMD11 (*p=0.0002 and **p<0.0001).

To confirm that the increase in PSMD11 protein levels corresponds to a concomitant increase in the proteasomal function as well, a proteasome substrate cleavage assay was performed. Suc-Leu-Leu-Val-Tyr-AMC (S-LLVY-AMC) is a fluorescent substrate that becomes fluorescent upon cleavage by the 20S proteasome. Spinal cord protein lysates were prepared cord were obtained by immersing the tissue in PhosphoSafe buffer (EMD Millipore) in Lysing Matrix D-containing tubes (MP Biomedicals, Illkirch, France). Protein concentration was determined by the Bradford method using the BioRad Protein assay reagent. 90 mg of total protein was added to assay buffer (T-PER containing 5 mM of Suc-LLVY-AMC and 1 mM ATP). Enzyme reaction was initiated at 37° C./5% $CO_2$. Fluorescence was measured after 2 hours using a microplate reader (Promega discoverer, Promega corp). Excitation was set at 360 nm and Emission was set 450 nm. Assay buffer with 5 mM of Suc-LLVY-AMC was used as blank. Proteasomal activity was as calculated (Fluorescence value of sample−Fluorescence value of blank). The average of fluorescence values from group 1 (i.e. G1) was calculated and the % change in the fluorescence compared to that of the G1 group average were plotted. Statistical analyses were performed in GraphPad Prism. Data sets were analyzed by one-way ANOVA followed by Dunnett's test. Data represented as Mean±SEM. A level of p<0.05 was considered statistically significant. As shown in FIG. 6B, compared to the G1 group, the G2 group had significantly lower proteasomal activity (*p=0.0377). By contrast, groups G3 and G4 had significantly elevated levels of proteasomal activity compared the G2 group (**p<0.01). These result suggest that CT6 and CT6m treatments improve the proteasomal activity. As seen from FIGS. 6A and 6B treatment with CT6 and CT6m restored the proteasomal functional activity in the spinal cord to that of levels in wild-type mice.

Lysosomal Function in Spinal Cord: As noted above, neurons depend on the ubiquitin-proteasome system (UPS) and autophagy-associated lysosomal degradation for protein degradation and removal. While the UPS targets ubiquitin conjugated proteins for removal the lysosomal pathway targets long-lived proteins and damaged organelles. Dysregulation of protein degradation is implicated in the pathogenesis of ALS (Root et al., Neurobiology of Disease 154, 105360, 2021) (Rubinsztein, Nature 443, 780-786, 2006). ALS is characterized by the presence of cytoplasmic inclusions or protein aggregates in the affected motor neurons indicating an impairment of protein degradation. Lysosomal degradation of cytoplasmic aggregates or inclusions is vital for neuronal growth and survival. Also, disruption of lysosomal function is sufficient to cause neurodegeneration. Lysosome-associated membrane protein type 2 (LAMP2A) is a key protein required for proper functioning of the lysosome and it is the receptor for chaperone-mediated autophagy by which substrate proteins interact with and are subsequently transported into the lysosomal lumen for degradation.

To determine whether CT6 or CT6m treatment affect lysosomal function, LAMP2A protein levels in the spinal cord of SOD1-G93A mice were quantified by western blot. Protein lysates were prepared using PhosphoSafe™ extraction reagent (EMD Millipore, catalogue 71296) and mechanically homogenized using bead-filled Lysing Matrix D tubes (MP Biomedicals, Illkirch, France). Protein concentration was determined by the Bradford method using the BioRad Protein assay reagent. 30 mg of total protein was mixed with SDS sample buffer and boiled for min. The samples were electrophoresed on custom-made SDS-Polyacrylamide Bis-tris gels (4-12%) using the MOPS or MES running buffer followed by transfer onto PVDF membrane (Invitrogen) using iBlot2 (Invitrogen). The membrane was blocked using Odyssey blocking buffer for 1 hour and incubated with LAMP2A specific antibody (Catalog #A0593; Abclonal) at 1:2000 dilution overnight under shaking conditions at 4° C. The following day, the membrane was thoroughly washed in TBST (TBS+Tween 20) and incubated in HRP conjugated secondary antibody (Catalog #7074; Cell signaling) at 1:2000 dilution at room temperature for 1 hour. Densitometric quantification of the immunoblots was performed by GeneTools from Syngene after visualizing with GBox Mini (SYNGENE). Target bands were normalized using their respective b-actin loading controls. Each dot in the plot of FIG. 7 represents pooled spinal cord lysates from two animals. LAMP2A protein level is significantly decreased in the spinal cord lysates of SOD1$^{G93A}$ mice compared to the wild-type mice. However, CT6 or CT6m treated mice had significantly increased LAMP2A protein levels compared to mock-treated SOD1$^{G93A}$ mice. LAMP2A protein levels in the spinal cord lysates of CT6 or CT6m treated SOD1$^{G93A}$ mice were restored to that of the levels in wild-type mice. Statistical analyses were performed in GraphPad Prism. Data sets were analyzed by one-way ANOVA followed by Dunnett's test. Data represented as Mean±SEM. A level of p<0.05 was considered statistically significant. As shown in FIG. 7, compared to the G2 group, G3 and G4 had significantly elevated levels of LAMP2A (***p=0.0002 and

****p<0.0001). This result suggests that CT6 and CT6m treatments increase lysosomal activity and treatment with CT6 and CT6m restored the lysosomal activity in the spinal cord to that of levels in wild-type mice.

Example 2: Evaluation of Efficacy of Microbiome Compositions in ALS Female Mouse Model In-depth details of, e.g., the mouse model used, studies performed, and the results of this Example is listed in Appendix 5 filed herewith.

The study as described in Example 1 is repeated in female SOD1-G93A transgenic mice. Results of this study are analyzed as described in Example 1.

Example 3: Physical Performance Tests to Evaluate Efficacy of Microbiome Compositions on ALS Mouse Model In-depth details of the purpose, mouse model used, studies performed, and the results of this Example is listed in Appendix 5 filed herewith.

This Example provides an evaluation of the efficacy of microbiome compositions, specifically CT6 and CT6m compositions, in in vivo mouse model for ALS using physical performance tests.

Mouse Model: The mouse model described in Example 1 was used in this study.

Study: Physical performance tests are important for assessing the effect of physical activity interventions in people with neurodegenerative diseases, disorders, or conditions (e.g. ALS, PD, AD, HD, dementia etc.).

Male and female mice were each divided into four groups of 13-15 animals per group, and were provided mock (DPBS) or microbiome composition (CT6 or CT6m; composition details listed in Tables 2 and 3 above) by daily oral gavage for a known number of consecutive days. The groups were: (i) G1: Wild type mice treated with DPBS; (ii) G2: SOD1 transgenic mice treated with DPBS; (iii) G3: SOD1 transgenic mice treated with CT6 composition; and (iv) G4: SOD1 transgenic mice treated with CT6m composition. After treatment, each group was subjected to physical performance tests including Beam Walk Tests, P100 Rotatod Tests, and Grip Strength Tests.

Results:

Beam Walk: The 'beam walk test' or 'balance beam test' is used to analyze rodent gait in a testing environment that challenges their ability to maintain balance given that the animals have to cross an elevated beam with a narrow diameter. This test is used for the assessment of motor coordination, particularly of the hind-limb. The animals are placed in one corner of the narrow beam and allowed to walk across the narrow beam from one end to the other three times. The number of foot slips encountered, and time taken to cross the beam in each trial are recorded.

The beam walk test was carried out in male mice that were 66-80 days old. The mice were treated for 17 consecutive days following which mice in each of the four study groups were subjected to the beam walk test. The results of this test are shown in FIG. 8A. Results showed that wild-type mice of G1 passed the test about 51.1% of the time. In contrast SOD1 mice that were mock-treated (i.e. G2 mice) passed the test only about 41% of the time. Treatment with CT6 and CT6m compositions (i.e. G3 and G4) resulted in higher pass rates of about 59% and 46% respectively, significantly higher than the G2 mock-treated SOD1 mice.

Similarly, the beam walk test was carried out in female mice that were 71-80 days old. The mice were treated for 22 consecutive days following which mice in each of the four study groups were subjected to the beam walk test. The results of this test are shown in FIG. 8B. Results showed that wild-type mice of G1 passed the test about 64.1% of the time. The SOD1 mice that were mock-treated (i.e. G2 mice) also passed the test about 61.5% of the time. However, treatment with CT6 and CT6m compositions (i.e. G3 and G4) resulted in significantly higher pass rates of about 84.8% and 80.9% respectively, significantly higher than both G1 wild-type and G2 mock-treated SOD1 mice.

Thus, microbiome compositions disclosed herein help improve motor coordination, which is a major concern in patients with neurodegenerative diseases, disorders, or conditions.

P100 Rotarod: The 'rotarod test' is frequently used in early stages of drug development to screen out drugs that might later cause subtle impairments. The rotarod test is a performance-based test on a long cylindrical rotating rod with forced motor activity being applied by rodents. In this test, a rodent is placed on a long cylindrical rod which rotates along its long axis. The speed of the rod can be held constant or accelerated. However, if the speed is constant, some animals with poor coordination will fall off at the start, whereas for those that do stay on, the test soon starts to measure endurance rather than coordination per se. In the accelerating version of the test, when rodents fall off from the rod onto the plate placed below, the animal latency to fall (in seconds) is recorded. The length of time the animal stays on this rotating rod is a measure of their balance, coordination, physical condition, and motor planning.

The rotarod test was carried out in male mice that were 66-80 days old. The mice were treated for 17 consecutive days following which mice in each of the four study groups were subjected to the rotarod test. The speed of the rod was held constant. The results of this test are shown in FIG. 9A. Results showed that wild-type mice of G1 stayed on the rod for close to 130-150 seconds, compared to SOD1 mice that were mock-treated (i.e. G2 mice) that stayed on the rod for only about 75-80 seconds. Treatment with CT6 and CT6m compositions (i.e. G3 and G4) resulted in higher times on the rod for about 110 seconds and 90 seconds respectively, higher than the G2 mock-treated SOD1 mice.

Similarly, the rotarod test was carried out in female mice that were 71-80 days old. The mice were treated for 22 consecutive days following which mice in each of the four study groups were subjected to the rotarod test. The results of this test are shown in FIG. 9B. Results showed that wild-type mice of G1 stayed on the rod for close to 160-165 seconds, compared to SOD1 mice that were mock-treated (i.e. G2 mice) that stayed on the rod for only about 100-10$^5$ seconds. Treatment with CT6 and CT6m compositions (i.e. G3 and G4) resulted in higher times on the rod for about 140 seconds and 135 seconds respectively, higher than the G2 mock-treated SOD1 mice.

Thus, microbiome compositions disclosed herein help improve balance, coordination, physical condition, and motor planning, all of which are major concerns in patients with neurodegenerative diseases, disorders, or conditions.

Grip Strength: 'Grip bar strength test' or 'grip strength test' is the most commonly used in vivo test for assessing impaired limb strength caused by pathology progression. It is a simple and rapid non-invasive method used to assess the muscle force of forelimbs/hindlimbs in vivo. The animal is lowered toward a platform and is allowed to grasp a horizontal metal bar or grid with its forelimb/hindlimbs and then pulled backward by the experimenter until it releases its grip. The bar or grid is attached to a transducer and the force produced during the animal pulling is measured. Forelimb and hindlimb assessments can be measured simultaneously using dual sensor models or in separate trials using single stand model. The values are expressed in pounds, kilograms, grams, or newtons.

The grip strength test was carried out in male mice that were 76-90 days old. The mice were treated for 27 consecutive days following which mice in each of the four study groups were subjected to the grip strength test. The results of this test are shown in FIG. 10A. Results showed that wild-type mice of G1 showed a grip strength of about 210 grams, compared to SOD1 mice that were mock-treated (i.e. G2 mice) that owed a grip strength of about 150 grams. Treatment with CT6 and CT6m compositions (i.e. G3 and G4) resulted in higher grip strengths of about 180 grams and 185 grams respectively, higher than the G2 mock-treated SOD1 mice.

Similarly, the grip strength test was carried out in female mice that were 76-90 days old. The mice were treated for 27 consecutive days following which mice in each of the four study groups were subjected to the grip strength test. The results of this test are shown in FIG. 10B. Results showed that wild-type mice of G1 showed a grip strength of about 200 grams, compared to SOD1 mice that were mock-treated (i.e. G2 mice) that showed a grip strength of about 100 grams. Treatment with CT6 and CT6m compositions (i.e. G3 and G4) resulted in no statistically significant increase in grip strength than the G2 mock-treated SOD1 mice. The fact that an increase in grip strength was not observed is not dispositive as whether CT6 and CT6m compositions can or would be expected to improve, e.g., limb strength or other symptoms associated with neurodegenerative diseases, disorders, or conditions, at least because the SOD1 mice used in this analysis model aggressive and fast moving neurodegenerative conditions. As such, an impact of CT6 and CT6m compositions on, e.g., limb strength or other symptoms associated with neurodegenerative diseases, disorders, or conditions, may be more significant and/or detectable in less aggressive models or in human subjects (e.g., human subjects having mild or moderate neurodegenerative diseases, disorders, or conditions).

Thus, microbiome compositions disclosed herein may help improve impaired limb strength, which is a concern in patients with neurodegenerative diseases, disorders, or conditions.

Example 4: Effect of Microbiome Therapies (MBTs) on Metabolome of Wild-Type Mice This Example provides an evaluation of the effect of microbiome therapies (MBTs) on metabolome of wild-type male and female mice.

Mouse Model: Wild-type male and female mice were used in this study.

Study: 10 male and 10 female mice were each divided into two groups. One group was provided mock (DPBS) and the other was provided CT6 microbiome composition (composition details listed in Table 2) by daily oral gavage for 21 days. That is, the groups were: (i) G1: Wild type mice treated with DPBS; and (ii) Wild type mice treated mice treated with CT6 composition. After treatment for 21 days, terminal bleeds were sent for metabolomics analysis.

Results: Metabolomics analysis identified 660 metabolites, out of which 436 metabolites were increased by >1% in the CT6-treated animals compared to mock-treated animals (see FIG. 11). FIG. 12 shows results of the metabolomics analysis of CT6-treated wild-type male mice plasma and plots the % change of metabolite levels relative to vehicle-treated mice. Similarly, FIG. 13 shows results of the metabolomics analysis of CT6-treated wild-type female mice plasma and plots the % change of metabolite levels relative to vehicle-treated mice. FIG. 14 and FIG. 15 also provides enrichment ratios of the top 25 metabolites that were enriched in male and female wild-type mice treated with CT6 composition, respectively. Furthermore, FIG. 16A and FIG. 16B show results of the metabolomics analysis of CT6-treated wild-type male and female mice plasma and plot the % change of metabolite levels relative to vehicle-treated mice for metabolites that increased in male and female mice. FIG. 16B also provides enrichment ratios of 25 metabolites that increased in both male and female wild-type mice treated with CT6 composition. Analogously, FIG. 17A and FIG. 17B show results of the metabolomics analysis of CT6-treated wild-type male and female mice plasma and plot the % change of metabolite levels relative to vehicle-treated mice for metabolites that decreased in male and female mice. FIG. 17B also provides enrichment ratios of 25 metabolites that decreased in both male and female wild-type mice treated with CT6 composition. Additionally, Appendix 4 lists the % metabolite changes in CT6-treated male and female mice compared to mock-treated male and female mice, respectively.

As seen from FIGS. 11-17, multiple classes of metabolites are modulated when treated with microbiome compositions disclosed herein (e.g. CT6). One such class that is modulated is bile acids. As shown in FIG. 18A, bile acids are known to be associated with various neurodegenerative diseases, disorders, or conditions, including ALS, PD, AD, and HD. Bile acids are also key components of neuronal pathways that are known to be disrupted in patients with neurodegenerative diseases, disorders, or conditions (Ackerman, H. D. and Gerhard, G. S., Frontiers in Aging Neuroscience, 8, 263 (2016)). FIG. 18B shows a list of bile acids that were modulated in male and female mice upon treatment with CT6 compositions, along with the % change of the bile acid metabolite relative to vehicle-treated mice in CT6-treated wild type male and female mice. Accordingly, treatment with microbiome compositions as disclosed herein that modulate levels of bile acids in a subject can provide new methods of treatment for various neurodegenerative diseases, disorders, or conditions.

Example 5: Nitric Oxide Assay for Finding Metabolites that Modulate Neuroinflammation This Example provides an assay to determine metabolites that modulate neuroinflammation.

Study: The SIM-A9 microglial cell line was purchased from ATCC and cultured in DMEM:F12 media supplemented with 10% heat-inactivated FBS, 5% heat-inactivated horse serum, and 1% L-glutamine. Cells were maintained at 37° C. and 5% $CO_2$ in incubators. All experiments were carried out using only passage 3-7 cells. For 6-well plates, cells were seeded at a density of $1 \times 10^5$ cells/mL with a total volume of 3 ml (300,000 cells total). 10 micromole of each metabolite was added to 2 wells. For the control wells, PBS with solvent control were added. After 6 hours of incubation at 37° C. and 5% $CO_2$, one of the two wells for each metabolite were treated with 1 µg/ml of Lipopolysaccharide (LPS) in water. In the other well, water with no LPS was added. Control wells were also treated with either water containing LPS or no LPS. After 16 hours of LPS treatment, approximately 800 μL of conditioned media was collected from each well using a 1 mL syringed and filtered using a 0.22-micron PES syringe filter.

For the Nitric Oxide (NO) assay, 50 μl of the conditioned media were placed onto clear 96-well plate in duplicates. The NO Assay was initiated by adding 50 μl of NO Assay Solution (A-103 Nitric Oxide Assay Kit; BMR Services) to each well (see FIG. 19B). The plate was incubated at room temperature shielded from light for 15 min. Culture media used for growing SIMA9 cells was used for background measurement. The absorbance was measured at 560 nm using a microplate reader (Promega discoverer, Promega corp). In order to correct for background absorbance, the sample or control absorbance values were subtracted from the culture media background values. 1 μM of Nitrite dissolved in SIM-A9 cell culture media was used as positive control. SIM-A9 cell culture media without Nitrite was used as negative control for the assay. The average of absorbance of the duplicate wells for each condition was calculated. The NO levels were calculated as:

% NO levels=[(sample NO absorbance value/control NO absorbance value)*100]

Results: FIG. 19A shows the role NO plays in various aspects of neuronal function, including but not limited to neurotransmission, neuroplasticity, brain microcirculation, inflammation, oxidative stress, etc. FIG. 19C plots the results of the NO assay. Specifically, it shows % Nitrite levels compared to untreated SIMA9 cells for various metabolites and controls. The white bars represent statistically significant results and metabolites corresponding with these yellow bars are involved in modulation of neuroinflammation.

Example 6: Evaluation of Efficacy of Microbiome Compositions in Treating Amyloid Plaque Deposits in Tg2576 Mouse Model This Example provides an evaluation of the efficacy of microbiome compositions, specifically CT10, CT10m, and CT10x compositions, in in vivo mouse model for treating amyloid plaque deposits.

Mouse Model: Tg2576 mice that were 9 months old were used for these experiments. This mouse model is one of the most popular transgenic mice models that overexpresses a mutant form of Amyloid Precursor Protein (APP) (isoform 695) with the Swedish mutation (KM670/671NL), resulting in increased levels of Amyloid beta (Aβ) and ultimately amyloid plaques. Wild type mice were used as a control in all experiments.

Study: Tg2576 mice were divided into five groups of 15 animals per group, and were provided mock (DPBS) or microbiome composition (CT10, CT10m, or CT10x; composition details listed in Tables 4, 5, and 6 below) by daily oral gavage for 6 months. The groups were: (i) G1: Wild type mice treated with DPBS; (ii) G2: Tg2576 transgenic mice treated with DPBS; (iii) G3: Tg2576 transgenic mice treated with CT10 composition; (iv) G4: Tg2576 transgenic mice treated with CT10m composition; and (v) G5: Tg2576 transgenic mice treated with CT10x composition. The animals were sacrificed at the end of the study, following which histological analyses were performed.

TABLE 4

CT10 Composition

| # | Microbiome Therapy (MBT) | Concentration in CFU/ml |
|---|---|---|
| 1 | Bifidobacterium breve | $1 \times 10^9$ |
| 2 | Gluconacetobacter hansenii | $1 \times 10^9$ |
| 3 | Terrisporobacter glycolicus | $1 \times 10^9$ |
| 4 | Veillonella atypica | $1 \times 10^9$ |
| 5 | Lactobacillus plantarum | $1 \times 10^9$ |
| 6 | Coprococcus catus | $1 \times 10^9$ |
| 7 | Clostridium butyricum | $1 \times 10^9$ |
| 8 | Paenibacillus barengoltzii | $1 \times 10^9$ |
| 9 | Bacillus subtilis | $1 \times 10^9$ |
| 10 | Acidaminococcus sp. | $1 \times 10^9$ |

TABLE 5

CT10m Composition

| # | Microbiome Therapy (MBT) | Concentration in CFU/ml |
|---|---|---|
| 1 | Bifidobacterium breve | $2 \times 10^9$ |
| 2 | Gluconacetobacter hansenii | $2 \times 10^9$ |
| 3 | Terrisporobacter glycolicus | $2 \times 10^9$ |
| 4 | Veillonella atypica | $2 \times 10^9$ |
| 5 | Lactobacillus plantarum | $2 \times 10^9$ |
| 6 | Coprococcus catus | $2 \times 10^9$ |
| 7 | Clostridium butyricum | $2 \times 10^9$ |
| 8 | Paenibacillus barengoltzii | $2 \times 10^9$ |
| 9 | Bacillus subtilis | $2 \times 10^9$ |
| 10 | Acidaminococcus sp. | $2 \times 10^9$ |

TABLE 6

CT10x Composition

| # | Microbiome Therapy (MBT) | Concentration in CFU/ml |
|---|---|---|
| 1 | Bifidobacterium breve | $1 \times 10^9$ |
| 2 | Gluconacetobacter hansenii | $3 \times 10^9$ |
| 3 | Terrisporobacter glycolicus | $1 \times 10^9$ |
| 4 | Veillonella atypica | $3 \times 10^9$ |
| 5 | Lactobacillus plantarum | $3 \times 10^9$ |
| 6 | Coprococcus catus | $1 \times 10^9$ |
| 7 | Clostridium butyricum | $1 \times 10^9$ |
| 8 | Paenibacillus barengoltzii | $1 \times 10^9$ |
| 9 | Bacillus subtilis | $1 \times 10^9$ |
| 10 | Acidaminococcus sp. | $1 \times 10^9$ |

Methods:

Sectioning:

Paraffin embedded brains were sectioned on a microtome and sections were mounted onto supercharged microscope slides. All animals from all groups were sectioned in the same day (staining set). Sections were dried overnight and immunostained.

Immunostaining:

Separate antibody stainings were performed for each of (i) Amyloid plaque staining; (ii) Microglia staining; and (iii) Amyloid plaque microglia overlap. Brain sections were dewaxed and serially rehydrated. Antigen unmasking (retrieval) was performed in citrate solution with steaming. Non-specific antibody binding was blocked in a blocking solution of 5% normal horse serum and 0.5% Triton X100 in 1×PBS. Primary and secondary antibody solution were prepared in blocking solution. Sections were incubated overnight at 4° C. in a primary antibody solution comprised of (i) Amyloid plaque staining: anti-6E10; (ii) Microglia staining: anti-IbaA1/AIF-1; or (iii) Amyloid plaque microglia overlap: anti-6E10+anti-IbaA1/AIF-1. Sections were washed in 1×PBS and incubated for 1 hour at room temperature in secondary antibody solution comprised of (i) Amyloid plaque staining: IgG H&L conjugated to Alexa Fluor 647; (ii) Microglia staining: IgG H&L conjugated to Alexa Fluor 488; or (iii) Amyloid plaque microglia overlap: IgG H&L conjugated to Alexa Fluor 647, IgG H&L conjugated to Alexa Fluor 488. Sections were mounted with glass coverslips using Vectashield® PLUS Antifade Mounting Medium with DAPI. Slides were sealed and stored at 4° C. until imaged.

Image Acquisition:

Stained slides were imaged on a Zeiss Axiovision microscope using a 10× objective. Images were acquired using Micromanager software. An imaging grid was defined to acquire the entire section using multiple images with 10% overlap between individual images. Identical imaging settings were used for all sections within each staining set.

Processing:

Image processing was performed using the FIJI image processing package which is a distribution of ImageJ2. Images were saved and processed in TIFF format. A single image of each section was reconstructed from individual gridded image panels using the Grid/Collection Stitching plugin. Each single section image was scaled to 25% the original resolution using the scale function and bilinear interpolation. Scaled images were visually inspected to determine the sectioning depth through the hippocampus and cortex by setting the minimum and maximum values (min/max set) to the same values for all images in a staining set. The min/max set adjustment was performed independently for each immunostained secondary antibody and DAPI separately. The hippocampus and dorsal portion of the cortex (isocortex) were outlined as regions of interest (ROIs) for analysis. Scaled images were converted to 8 bit and were processed using the subtract background command with a 100 pixel rolling ball radius followed by 2 pixel size median filtering.

Quantification of Amyloid Burden and Plaque Size:

Quantification was performed using the FIJI image processing package which is a distribution of ImageJ2. Amyloid plaques were identified by thresholding the 6E10 processed images with the Auto threshold command using maximum entropy. The Analyze particles command calculated the size of each plaque and the percent area of each ROI covered by plaques. Plaque size and percent area data were saved as comma separated values files. Analyses and data visualization were performed in the R Statistical Computing Software.

Statistics:

Individual animal plaque burden and plaque size were calculated as the mean of multiple stained slides when more than one slide was used. Treatment group plaque burden and plaque size were calculated as the mean of individual animal values and the SEM was also calculated. Individual animal microglial recruitment was calculated as the mean of multiple stained slides when more than one slide was used. Treatment group microglial recruitment was calculated as the mean of individual animal values and the SEM was also calculated. Individual animal microglial association within amyloid plaques was calculated as the mean of all plaques for one individual from one stained slide. Treatment group microglial association within amyloid plaques was calculated as the mean of individual animal values and the SEM was also calculated. Differences in group values were assessed using a one-way ANOVA followed by a one-sided Dunnett's test for decreases in value compared to transgenic vehicle control (Group 2). Because treatment group effects on plaque size were previously evaluated using ANOVA and Dunnet's tests, the evaluation of binned plaque size was evaluated using student's t-tests with multiple hypothesis correction using the Benjimini-Hochberg method. Differences were considered statistically significant when $p<0.05$.

Results:

Amyloid Plaques in Cortex:

Amyloid plaque burden and plaque size in the cortex in treated animals were measured. Amyloid plaques were measured in the cortex of brain tissue sections using 6E10 antibody. Plaque burden was measured as the percent of cortex area with amyloid plaques (FIG. 20A). Plaque size was measured as the size in pixel area of amyloid plaques (FIG. 20B). Colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). $p<0.05$ was considered statistically significant. As observed from FIGS. 20A and 20B, amyloid plaque burden and size were reduced in the cortex when mice were treated with microbiome compositions, specifically with CT10, CT10m, and CT10x compositions.

Furthermore, amyloid plaques measured post-treatment in the cortex region of the brain were divided into bins by their plaque area. The colored bars show the mean for each group (n=6 or 7 animals) and error bars show the standard error of the mean. Values for each animal were determined by calculating the mean from 1 or 2 tissue sections from independent staining experiments. Group comparisons were conducted using student's t-test and p-values corrected for multiple hypothesis testing. $p<0.05$ was considered statistically significant. FIG. 23 shows that amyloid plaques categorized in different size bins in the cortex were reduced in animals treated with microbiome compositions.

Amyloid Plaques in Hippocampus:

Amyloid plaque burden and plaque size in the hippocampus in treated animals were measured. Amyloid plaques were measured in the hippocampus of brain tissue sections using 6E10 antibody. Plaque burden was measured as the percent of hippocampus area with amyloid plaques (FIG. 21A). Plaque size was measured as the size in pixel area of amyloid plaques (FIG. 21B). Colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). $p<0.05$ was considered statistically significant. As observed from FIGS. 21A and 21B, amyloid plaque burden and size were reduced in the hippocampus when mice were treated with microbiome compositions, specifically with CT10, CT10m, and CT10x compositions.

Furthermore, amyloid plaques measured post-treatment in the hippocampus region of the brain were divided into bins by their plaque area. The colored bars show the mean for each group (n=6 or 7 animals) and error bars show the standard error of the mean. Values for each animal were determined by calculating the mean from 1 or 2 tissue sections from independent staining experiments. Group comparisons were conducted using student's t-test and p-values corrected for multiple hypothesis testing. $p<0.05$ was considered statistically significant. FIG. 24 shows that amyloid plaques categorized in different size bins in the hippocampus were reduced in animals treated with microbiome compositions.

Amyloid Plaques in Cortex and Hippocampus:

Amyloid plaque burden and plaque size in both the cortex and hippocampus in treated animals were measured. Amyloid plaques were measured in the both the cortex and hippocampus of brain tissue sections using 6E10 antibody. Plaque burden was measured as the percent of cortex area with amyloid plaques (FIG. 22A). Plaque size was measured as the size in pixel area of amyloid plaques (FIG. 22B). Colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). p<0.05 was considered statistically significant. As observed from FIGS. 22A and 22B, amyloid plaque burden and size were reduced in both the cortex and hippocampus when mice were treated with microbiome compositions, specifically with CT10, CT10m, and CT10x compositions.

Furthermore, amyloid plaques measured post-treatment in both the cortex and hippocampus region of the brain were divided into bins by their plaque area. The colored bars show the mean for each group (n=6 or 7 animals) and error bars show the standard error of the mean. Values for each animal were determined by calculating the mean from 1 or 2 tissue sections from independent staining experiments. Group comparisons were conducted using student's t-test and p-values corrected for multiple hypothesis testing. p<0.05 was considered statistically significant. FIG. 25 shows that amyloid plaques categorized in different size bins in the cortex and hippocampus were reduced in animals treated with microbiome compositions.

Example 7: Evaluation of Efficacy of Microbiome Compositions in Microglia Recruitment and Microglial Association within Amyloid Plaques in Tg2576 Mouse Model This Example provides an evaluation of the efficacy of microbiome compositions, specifically CT10, CT10m, and CT10x compositions, in in vivo mouse model for microglia recruitment and microglial association within amyloid plaques.

Mouse Model: The mouse model described in Example 6 was used in this study.

Study: The study described in Example 6 was performed in this experiment.

Methods: The methods described in Example 6 specific to microglia recruitment and microglial association within amyloid plaques were performed in this experiment.

Quantification of Microglia Recruitment and Association with Amyloid Plaques:

Quantification was performed using the FIJI image processing package which is a distribution of ImageJ2. Microglia were identified by thresholding the processed Iba1 stained images with the Auto threshold command using maximum entropy. The Analyze particles command calculated the percent area of each ROI covered by Iba1 stained cells. For microglia associated with amyloid plaques, the processed Iba1 image was masked using the processed amyloid plaque image and the percent area of each plaque covered by Iba1 cells within each ROI was calculated. Percent area data were saved as comma separated values files. Analyses and data visualization were performed in the R Statistical Computing Software.

Results:

Microglia in Cortex:

Microglia staining was performed in the cortex in treated animals as described above in Example 6. Microglia stained cells and processes were measured in the cortex of brain tissue sections using Iba1/AIF-1 antibody. FIG. 26 shows images of the stained microglia in sections of the brain with the images adjusted to the same intensity scale. Iba1 area was measured as the percent of cortex area with Iba1 positive stained area (FIG. 27A). In the figure, colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). p<0.05 was considered statistically significant. As observed from FIG. 27A, microglia were reduced in the cortex when mice were treated with microbiome compositions, specifically with CT10x compositions. It is hypothesized that the effect observed with CT10x compositions is the highest, as these compositions comprise higher amounts of the microbial strains as compared to CT10 and CT10m compositions.

Additionally, microglia within amyloid plaques in the cortex in treated animals were measured. Microglia were measured in the cortex of brain tissue sections using 6E10 (amyloid) Iba1/AIF-1 (microglia) antibody. Iba1 area was measured as the percent of cortex area with Iba1 positive stained area (FIG. 29A). In FIG. 29A, the colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). p<0.05 was considered statistically significant. As observed from FIG. 29A, microglia within amyloid plaques in the cortex region of the brain were significantly reduced when mice were treated with microbiome compositions, specifically with CT10, CT10m, and CT10x compositions.

Microglia in Hippocampus:

Microglia staining was performed in the hippocampus in treated animals as described above in Example 6. Microglia stained cells and processes were measured in the cortex of brain tissue sections using Iba1/AIF-1 antibody. Iba1 area was measured as the percent of cortex area with Iba1 positive stained area (FIG. 27B). In the figure, colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). p<0.05 was considered statistically significant. As observed from FIG. 27B, microglia were reduced in the hippocampus when mice were treated with microbiome compositions, specifically with CT10x compositions. It is hypothesized that the effect observed with CT10x compositions is the highest, as these compositions comprise higher amounts of the microbial strains as compared to CT10 and CT10m compositions.

Additionally, microglia within amyloid plaques in the hippocampus in treated animals were measured. Microglia were measured in the hippocampus of brain tissue sections using 6E10 (amyloid) Iba1/AIF-1 (microglia) antibody. Iba1 area was measured as the percent of cortex area with Iba1 positive stained area (FIG. 29B). In FIG. 29B, the colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). p<0.05 was considered statistically significant. As observed from FIG. 29B, microglia within amyloid plaques in the hippocampus region of the brain were reduced when mice were treated with microbiome compositions, specifically with CT10m, and CT10x compositions. It is hypothesized that the effect observed with CT10m and CT10x compositions are the highest, as these compositions comprise higher amounts of the microbial strains as compared to the CT10 composition.

Microglia in Cortex and Hippocampus:

Microglia staining was performed in the both the cortex and hippocampus in treated animals as described above in Example 6. Microglia stained cells and processes were measured in the cortex of brain tissue sections using Iba1/AIF-1 antibody. Iba1 area was measured as the percent of cortex area with Iba1 positive stained area (FIG. 27C). In the figure, colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). p<0.05 was considered statistically significant. As observed from FIG. 27C, microglia were reduced in the cortex and hippocampus when mice were treated with microbiome compositions, specifically with CT10m and CT10x compositions. It is hypothesized that the effect observed with CT10m and CT10x compositions are the highest, as these compositions comprise higher amounts of the microbial strains as compared to the CT10 composition.

Additionally, microglia within amyloid plaques in the cortex and hippocampus in treated animals were measured. Microglia were measured in the cortex and hippocampus of brain tissue sections using 6E10 (amyloid) Iba1/AIF-1 (microglia) antibody. Iba1 area was measured as the percent of cortex area with Iba1 positive stained area (FIG. 29C). In FIG. 29C, the colored bars show the mean for each group (n=6 or 7 animals) and error bars show the standard error of the mean. Values for each animal were determined by calculating the mean from 1 or 2 tissue sections from independent staining experiments. Group comparisons were conducted using an ANOVA (p values in top left of plots) followed by a one-sided Dunnett's test using G2 as the control comparator group (brackets and numbers above bars). p<0.05 was considered statistically significant. As observed from FIG. 29C, microglia within amyloid plaques in the cortex and hippocampus region of the brain were significantly reduced when mice were treated with microbiome compositions, specifically with CT10, CT10m, and CT10x compositions.

Other Embodiments

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

It is to be understood that while embodiments of the invention have been described in conjunction with the detailed description thereof, the foregoing description is intended to illustrate and not limit the scope of the invention, which is defined by the scope of the appended claims. Other aspects, advantages, and modifications are within the scope of the following claims.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating or preventing amyotrophic lateral sclerosis, the method comprising:
   administering to a subject in need thereof a composition comprising *Gluconacetobacter hansenii*, *Terrisporobacter glycolicus*, *Coprococcus catus*, *Lactobacillus plantarum*, *Veillonella atypica*, and *Bifidobacterium breve*.

2. The method of claim 1, wherein the subject is a mammal.

3. The method of claim 1, wherein the subject is a human.

4. The method of claim 1, wherein the composition comprises seven or more microbial strains.

5. The method of claim 1, wherein the composition comprises ten or more microbial strains.

6. The method of claim 1, wherein the composition is administered topically, orally, subcutaneously, intravenously, intramuscularly, intracerebrally, intrathecally, rectally, opthalmically, intravitreally, or suprachoroidally.

7. The method of claim 6, wherein the composition is administered orally.

8. The method of claim 6, wherein the composition is administered intracerebrally.

9. The method of claim 1, wherein the composition is formulated as a syrup, a liquid, a tablet, a troche, a gummy, a capsule, a powder, a gel, a film, an injection, or an eye drop.

10. The method of claim 1, wherein each microbial strain is present in the composition at a concentration from $10^1$ to $10^{15}$ CFU.

11. The method of claim 1, wherein each microbial strain is present in the composition at a concentration of at least $10^6$ CFU.

12. The method of claim 1, wherein *Gluconacetobacter hansenii, Terrisporobacter glycolicus, Coprococcus catus, Lactobacillus plantarum, Veillonella atypica*, and *Bifidobacterium breve* are administered to modulate the microbiome of the subject.

13. The method of claim 1, wherein *Gluconacetobacter hansenii, Terrisporobacter glycolicus, Coprococcus catus, Lactobacillus plantarum, Veillonella atypica*, and *Bifidobacterium breve* are administered to maintain the microbiome of the subject.

* * * * *